(12) United States Patent
Ogawa et al.

(10) Patent No.: US 12,329,028 B2
(45) Date of Patent: Jun. 10, 2025

(54) ORGANIC ELECTROLUMINESCENT ELEMENT

(71) Applicant: NIPPON STEEL Chemical & Material Co., Ltd., Tokyo (JP)

(72) Inventors: Junya Ogawa, Tokyo (JP); Yuji Ikenaga, Tokyo (JP); Kazunari Yoshida, Tokyo (JP); Ikumi Kitahara, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 882 days.

(21) Appl. No.: 17/604,087

(22) PCT Filed: Apr. 17, 2020

(86) PCT No.: PCT/JP2020/016869
§ 371 (c)(1),
(2) Date: Oct. 15, 2021

(87) PCT Pub. No.: WO2020/218187
PCT Pub. Date: Oct. 29, 2020

(65) Prior Publication Data
US 2022/0216427 A1 Jul. 7, 2022

(30) Foreign Application Priority Data

Apr. 25, 2019 (JP) .................. 2019-083852

(51) Int. Cl.
*H01L 51/00* (2006.01)
*H10K 71/16* (2023.01)
(Continued)

(52) U.S. Cl.
CPC ....... *H10K 85/6572* (2023.02); *H10K 71/164* (2023.02); *H10K 85/342* (2023.02);
(Continued)

(58) Field of Classification Search
None
See application file for complete search history.

(56) References Cited

U.S. PATENT DOCUMENTS

| | | |
|---|---|---|
| 2010/0187977 A1 | 7/2010 | Kai et al. |
| 2014/0197386 A1 | 7/2014 | Kim et al. |
| | (Continued) | |

FOREIGN PATENT DOCUMENTS

| | | | |
|---|---|---|---|
| GB | 2471606 A | * | 1/2011 |
| JP | 2003-133075 A | | 5/2003 |
| | (Continued) | | |

OTHER PUBLICATIONS

International Preliminary Report on Patentability for International Application No. PCT/JP2020/016869 dated Mar. 29, 2021, with an English translation.

*Primary Examiner* — Tae H Yoon
(74) *Attorney, Agent, or Firm* — Birch, Stewart, Kolasch & Birch, LLP

(57) ABSTRACT

Provided is an organic EL device including: a light emitting layer between an anode and a cathode facing each other, in which the light emitting layer contains a first host, a second host, and a luminescent dopant, an indolocarbazole compound represented by General Formula (1) is contained as the first host, and a biscarbazole compound or a dibenzofuran compound having a dibenzofuran or dibenzothiophene ring is contained as the second host. This organic EL device has a low drive voltage, high efficiency, and high drive stability.

13 Claims, 1 Drawing Sheet

(51) Int. Cl.
  *H10K 85/30*  (2023.01)
  *H10K 85/60*  (2023.01)
  *H10K 50/11*  (2023.01)
  *H10K 50/12*  (2023.01)
  *H10K 50/13*  (2023.01)
  *H10K 101/00*  (2023.01)
  *H10K 101/10*  (2023.01)

(52) U.S. Cl.
  CPC ......... *H10K 85/622* (2023.02); *H10K 85/654* (2023.02); *H10K 85/6574* (2023.02); *H10K 85/6576* (2023.02); *H10K 50/11* (2023.02); *H10K 50/12* (2023.02); *H10K 50/13* (2023.02); *H10K 2101/10* (2023.02); *H10K 2101/90* (2023.02)

(56) References Cited

U.S. PATENT DOCUMENTS

| | | |
|---|---|---|
| 2014/0306207 A1 | 10/2014 | Nishimura et al. |
| 2014/0374728 A1 | 12/2014 | Adamovich et al. |
| 2015/0001488 A1 | 1/2015 | Min et al. |
| 2015/0236262 A1 | 8/2015 | Cho et al. |
| 2017/0263868 A1 | 9/2017 | Tada et al. |
| 2018/0138420 A1 | 5/2018 | Tada et al. |
| 2018/0138425 A1 | 5/2018 | Ma et al. |
| 2018/0254426 A1 | 9/2018 | Ikenaga et al. |
| 2020/0006672 A1 | 1/2020 | Sagara et al. |

FOREIGN PATENT DOCUMENTS

| | | |
|---|---|---|
| WO | WO 2008/058748 A1 | 5/2008 |
| WO | WO 2011/136755 A1 | 11/2011 |
| WO | WO 2013/082075 A1 | 5/2013 |
| WO | WO 2016/042997 A1 | 3/2016 |
| WO | WO 2016/158363 A1 | 10/2016 |
| WO | WO 2016/194604 A1 | 12/2016 |
| WO | WO 2018/123783 A1 | 7/2018 |
| WO | WO 2018/173593 A1 | 9/2018 |

* cited by examiner

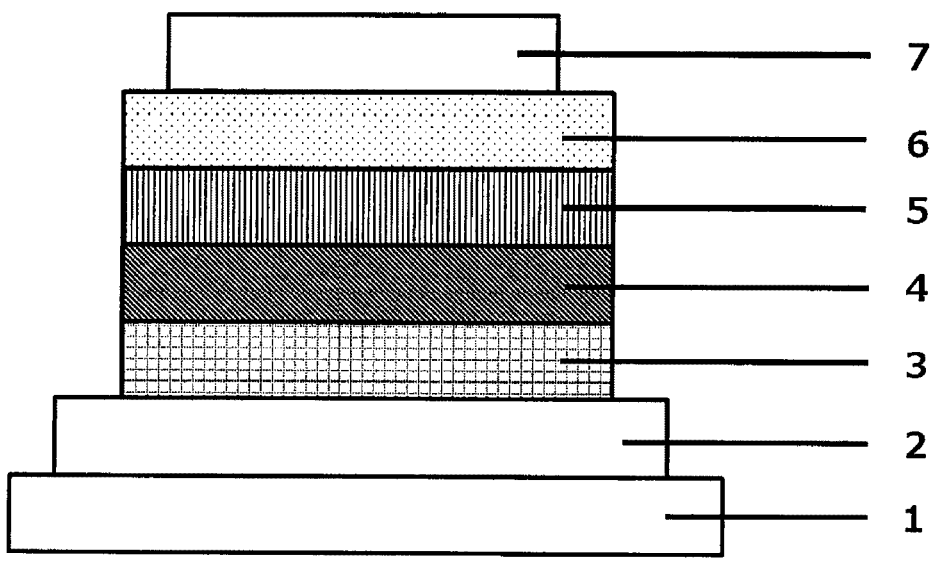

ORGANIC ELECTROLUMINESCENT ELEMENT

CROSS-REFERENCE TO RELATED APPLICATIONS

This application is the National Phase of PCT International Application No. PCT/JP2020/016869 filed Apr. 17, 2020, which claims priority under 35 U.S.C. § 119(a) to Patent Application No. 2019-083852, filed in Japan on Apr. 25, 2019, all of which are hereby expressly incorporated by reference into the present application.

TECHNICAL FIELD

The present invention relates to an organic electroluminescent element (also referred to as an organic EL device). Specifically, the present invention relates to an organic EL device using a material for an organic electroluminescent device comprises an indolocarbazole compound.

BACKGROUND ART

When a voltage is applied to an organic EL device, holes from an anode and electrons from a cathode are injected into a light emitting layer. Then, the injected holes and electrons are recombined in the light emitting layer to generate excitons. At this time, singlet excitons and triple excitons are generated at a ratio of 1:3 according to the statistical law of electron spin. It is said that the internal quantum efficiency of a fluorescent organic EL device in which light emission due to singlet excitons is used is limited to 25%. On the other hand, it is known that the internal quantum efficiency of a phosphorescent organic EL device in which light emission due to triple excitons is used can increase to up to 100% in a case where intersystem crossing from singlet excitons is efficiently performed.

However, extending the lifespan of a phosphorescent organic EL device has become a technical issue.

High-efficiency organic EL devices using delayed fluorescence have recently been developed. For example, PTL 1 discloses an organic EL device using a triplet-triplet fusion (TTF) mechanism which is one of delayed fluorescence mechanisms. In the TTF mechanism, a phenomenon that singlet excitons are generated due to collision of two triple excitons is used, and therefore it is theoretically thought that the internal quantum efficiency can be increased to 40%. However, since the efficiency thereof is lower than that of the phosphorescent organic EL device, further improvement in efficiency is required.

In PTL 2, an organic EL device in which a thermally activated delayed fluorescence (TADF) mechanism is used is disclosed. In the TADF mechanism, a phenomenon that reverse intersystem crossing from triple excitons to singlet exciton is caused in materials having a small energy difference between a singlet level and a triple level is used, and therefore, it is theoretically thought that the internal quantum efficiency can be increased to 100%. However, further improvement in lifespan characteristics is required similarly to the phosphorescent device.

CITATION LIST

Patent Literature

[PTL 1] WO2010/134350A
[PTL 2] WO2011/070963A
[PTL 3] WO2008/056746A
[PTL 4] JP2003-133075A
[PTL 5] WO2013/062075A
[PTL 6] US2014/0374728A
[PTL 7] US2014/0197386A
[PTL 8] US2015/0001488A
[PTL 9] US2015/0236262A
[PTL 10] WO2016/194604A
[PTL 11] WO2011/136755A

Use of indolocarbazole compounds as a host material is disclosed in PTL 3. Use of biscarbazole compounds as a host material is disclosed in PTL 4.

Use of biscarbazole compounds as a host mixture is disclosed in PTL 5 and 6. Use of indolocarbazole compounds and biscarbazole compounds as a host mixture is disclosed in PTL 7, 8, 9, and 10.

Use of a host material obtained by preliminarily mixing a plurality of hosts containing indolocarbazole compounds is disclosed in PTL 11.

However, none of them can be said to be sufficient, and further improvement is desired.

SUMMARY OF INVENTION

In order to apply organic EL devices to light sources and display devices such as flat panel displays, it is necessary to improve the luminous efficiency of devices and at the same time to secure sufficient stability during driving. An object of the present invention is to provide an organic EL device having a low drive voltage, high efficiency, and high drive stability.

The present inventors have conducted extensive studies, and as a result, they have found that a specific indolocarbazole compound may be used as a first host to obtain an organic EL device exhibiting excellent characteristics, thus leading to realization of the present invention.

The present invention is an organic EL device including: one or more light emitting layers between an anode and a cathode facing each other, in which at least one light emitting layer contains a first host selected from compounds represented by General Formula (1) below and a second host selected from compounds represented by General Formula (2) or (3) below.

[C1]

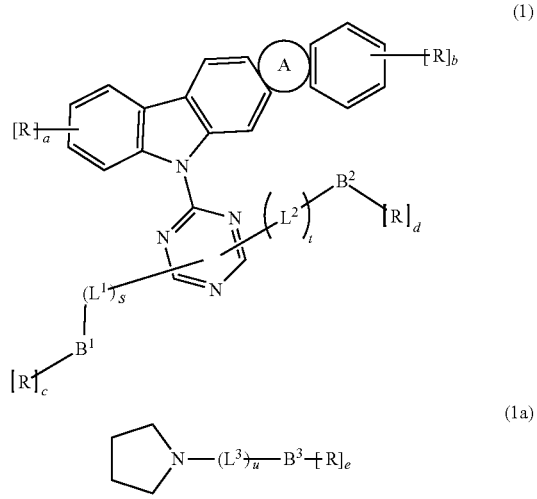

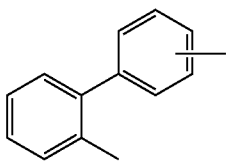
(1b)

Here, a ring A is a heterocyclic ring represented by Formula (1a) and condensed with an adjacent ring at an arbitrary position.

R's are independently hydrogen, an aliphatic hydrocarbon group having 1 to 10 carbon atoms, an aromatic hydrocarbon group having 6 to 10 carbon atoms, or an aromatic heterocyclic group having 3 to 12 carbon atoms, and $L^1$ to $L^3$ are independently a direct bond, an aromatic hydrocarbon group having 6 to 10 carbon atoms, or an aromatic heterocyclic group having 3 to 12 carbon atoms.

$B^1$ to $B^3$ independently represent a direct bond or a biphenyldiyl group represented by Formula (1b), and at least one of $B^1$ to $B^3$ is the biphenyldiyl group.

a, b, c, d, and e each independently represent an integer of 0 to 3, and s, t, and u each independently represent an integer of 1 and 2.

[C2]

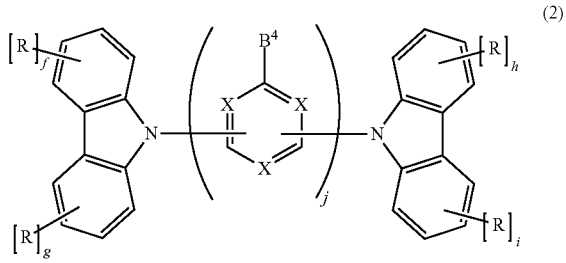
(2)

Here, R's independently represent hydrogen, an alkyl group having 1 to 20 carbon atoms, an acyl group having 2 to 20 carbon atoms, an alkoxy group having 2 to 20 carbon atoms, an aromatic hydrocarbon group having 6 to 24 carbon atoms, or an aromatic heterocyclic group having 3 to 16 carbon atoms, but are not a carbazole ring group.

$B^4$'s are independently hydrogen, an aromatic hydrocarbon group having 6 to 24 carbon atoms, or an aromatic heterocyclic group having 3 to 16 carbon atoms, and the aromatic hydrocarbon group or the aromatic heterocyclic group may have a substituent.

j represents an integer of 1 to 6, X's independently represent N, C—R', or C—, and each R' independently represents hydrogen, an alkyl group having 1 to 20 carbon atoms, an alkoxy group having 1 to 20 carbon atoms, and a diarylamino group having 12 to 44 carbon atoms. f, g, h, and i independently represent an integer of 1 to 3.

[C3]

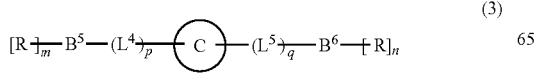
(3)

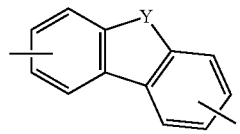
(3a)

Here, a ring C is a heterocyclic group represented by Formula (3a), $L^4$ and $L^5$ are independently a direct bond, an aromatic hydrocarbon group having 6 to 10 carbon atoms, or an aromatic heterocyclic group having 3 to 16 carbon atoms, $B^5$ and $B^6$ are a direct bond or an aromatic hydrocarbon group having 6 to 22 carbon atoms, R's are independently hydrogen, an aromatic hydrocarbon group having 6 to 10 carbon atoms, an aromatic heterocyclic group having 3 to 16 carbon atoms, an alkyl group having 1 to 10 carbon atoms, or a cycloalkyl group having 3 to 11 carbon atoms, and Y represents O or S.

m and n are numbers of substitutions and represent integers of 1 to 3. p and q are numbers of repetitions and are each independently integers of 1 to 4.

Preferred aspects of General Formulae (1) to (3) will be shown below.

In General Formula (1), $B^3$ is a biphenyldiyl group represented by Formula (1b), or a, b, and c are 0.

In General Formula (2), j is an integer of 1 to 3, or X's are N or C—H.

Formula (3a) is Formula (4) or (5) below.

In General Formula (3), $L^4$ and $B^5$ are a direct bond, $B^6$ is an aromatic hydrocarbon group represented by Formula (6) below, or $L^5$ is an aromatic heterocyclic group represented by Formula (7) below.

[C4]

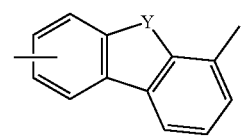
(4)

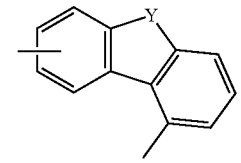
(5)

(Here, Y is O or S.)

[C5]

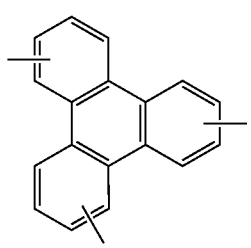
(6)

-continued

[C6]

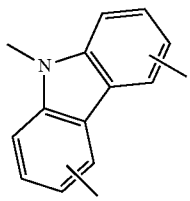

(7)

General Formula (1) is any of Formulae (8) to (11) below.

[C7]

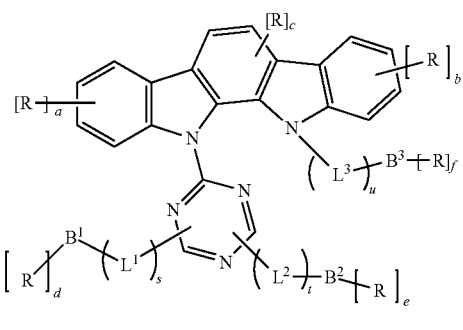

(8)

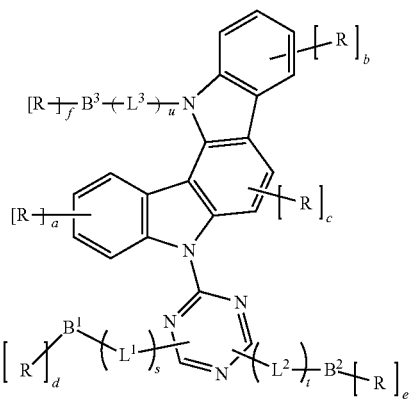

(9)

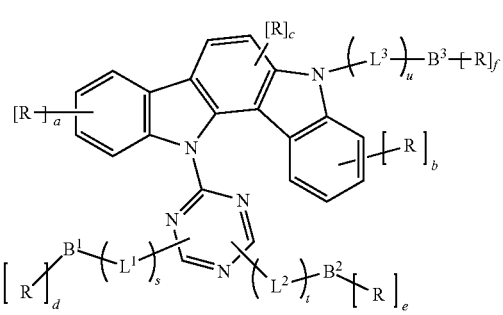

(10)

-continued

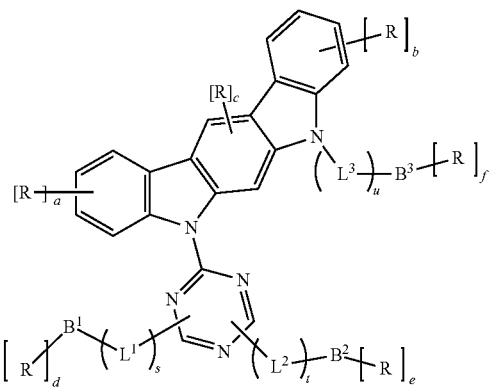

(11)

(Here, $B^1$ to $B^3$, $L^1$ to $L^3$, R, a to f, and s to u have the same meaning as those in General Formula (1).)

In the above-described organic electroluminescent device, a proportion of the first host is suitably greater than 20 wt % and less than 55 wt % based on the total amount of the first host and the second host.

It is preferable that the above-described organic electroluminescent device contain a luminescent dopant material together with the hosts in the light emitting layer.

The luminescent dopant material is preferably an organic metal complex containing at least one metal selected from the group consisting of ruthenium, rhodium, palladium, silver, rhenium, osmium, iridium, platinum, and gold, or a thermally activated delayed fluorescent dopant material.

In the above-described organic electroluminescent device, a hole-blocking layer may be provided adjacent to the light emitting layer, and the compound represented by General Formula (1) may be contained in the hole-blocking layer.

In addition, the present invention is a method for producing an organic electroluminescent device, the method including: a step of mixing a first host with a second host to prepare a premixture and then vapor-depositing the host material containing the hosts to form a light emitting layer when producing the above-described organic electroluminescent device.

In this case, a difference in 50% weight reduction temperature between the first host and the second host is preferably within 20° C.

In order to improve the characteristics of the device, it is necessary that durability of materials used in an organic layer with respect to charges be high. In a light emitting layer, it is particularly important to suppress leakage of excitons and charges to neighboring layers. In order to suppress this leakage of charges and excitons, it is effective to delocalize of a light emitting region in the light emitting layer. To do so, it is necessary to control the amount of both charges (electrons and holes) injected into the light emitting layer or the amount of both charges transported in the light emitting layer such that it is within a preferred range.

Here, an indolocarbazole compound which is used in the present invention and to which a specific aromatic heterocyclic ring is bonded has an ortho-linked biphenyldiyl group represented by Formula (1b). The injection and transport capability of materials for both charges used in an organic layer greatly depends on energy levels of molecular orbitals of materials and the extent of intermolecular interactions. Although indolocarbazole compounds to which specific aromatic heterocyclic rings are bonded have a particularly high electron injection and transport capability, close proximity of the indolocarbazole molecules can be inhibited due to steric hindrance effects of biphenyldiyl groups. Moreover, changing bonding sites or types of substituents of biphenyldiyl groups allows a high level of control of intermolecular interactions of molecular orbitals which greatly contribute to electron injection and transport with respect to the light emitting layer.

On the other hand, the carbazole compounds represented by General Formulae (2) and (3), and dibenzofuran and dibenzothiophene compounds have a particularly high hole injection and transport capability, therefore allowing a high level of control of hole injection and transport properties by changing a bonding site of a carbazole ring or the number and types of substituents on this skeleton. By mixing the above-described indolocarbazole compound with a biscarbazole compound for use, the amount of both charges injected into an organic layer can be adjusted to within a preferred range, and better device characteristics can be expected. In particular, since a delayed fluorescent EL device or a phosphorescent EL device has a sufficiently high lowest excited triplet energy to confine an excitation energy generated in a light emitting layer, there is no leakage of energy from the light emitting layer, and a low voltage, a high efficiency, and long lifespan can be achieved.

BRIEF DESCRIPTION OF DRAWINGS

FIG. 1 is a schematic cross-sectional view illustrating an example of an organic EL device.

DESCRIPTION OF EMBODIMENTS

An organic electroluminescent device of the present invention includes one or more light emitting layers between an anode and a cathode facing each other, and at least one light emitting layer contains a first host and a second host. The light emitting layer preferably includes a vapor deposition layer containing a first host, a second host, and a luminescent dopant material. This vapor deposition layer can be produced through vacuum deposition. This organic EL device of the present invention has an organic layer including a plurality of layers between an anode and a cathode facing each other. At least one of the plurality of layers is a light emitting layer, and there may be a plurality of light emitting layers.

The first host is a compound represented by General Formula (1), and a second host is a compound represented by General Formula (2) or (3).

General Formula (1) above will be described.

A ring A is a heterocyclic ring represented by Formula (1a) and condensed with an adjacent ring at an arbitrary position.

R's independently represent hydrogen, an aliphatic hydrocarbon group having 1 to 10 carbon atoms, an aromatic hydrocarbon group having 6 to 10 carbon atoms, or an aromatic heterocyclic group having 3 to 12 carbon atoms. An aliphatic hydrocarbon group having 1 to 8 carbon atoms, a phenyl group, or an aromatic heterocyclic group having 3 to 9 carbon atoms is preferable. An aliphatic hydrocarbon group having 1 to 6 carbon atoms, a phenyl group, or an aromatic heterocyclic group having 3 to 6 carbon atoms is more preferable.

Specific examples of the above-described aliphatic hydrocarbon group having 1 to 10 carbon atoms include methyl, ethyl, propyl, butyl, pentyl, hexyl, heptyl, octyl, nonyl, and decyl groups. An alkyl group having 1 to 4 carbon atoms is preferable.

Specific examples of the above-described aromatic hydrocarbon group having 6 to 10 carbon atoms or aromatic heterocyclic group having 3 to 12 carbon atoms include aromatic groups formed by removing one H from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, benzothiadiazole, dibenzofuran, dibenzothiophene, dibenzoselenophene, or carbazole. Preferred examples thereof include aromatic groups formed from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, or benzothiadiazole. More preferred examples thereof include aromatic groups formed from benzene, pyridine, pyrimidine, triazine, thiophene, isothiazole, triazole, pyridazine, pyrrole, pyrazole, imidazole, triazole, thiadiazole, pyrazine, furan, isoxazole, oxazole, or oxadiazole.

$L^1$, $L^2$, and $L^3$ are independently a direct bond, an aromatic hydrocarbon group having 6 to 10 carbon atoms, or an aromatic heterocyclic group having 3 to 12 carbon atoms. Preferred examples of aromatic hydrocarbon groups or aromatic heterocyclic groups are the same as those in the case where R's are these groups except that these groups are divalent groups.

$B^1$, $B^2$, and $B^3$ independently represent a direct bond or a group represented by Formula (1b), and at least one of $B^1$ to $B^3$ is a group represented by Formula (1b). $B^3$ is preferably the group represented by Formula (1b).

a, b, c, d, and e represent numbers of substitutions and each independently represent an integer of 0 to 3, and an integer of 0 or 1 is preferable. a, b, and c are preferably 0.

s, t, u represent numbers of repetitions and each independently represent an integer of 1 and 2, and 1 is preferable.

Preferred aspects of compounds represented by General Formula (1) are compounds represented by any of General Formulae (8) to (11) above. In General Formulae (8) to (11), symbols shared by those in General Formula (1) have the same meaning.

Specific examples of compounds represented by General Formula (1) will be shown below, but the present invention is not limited to these exemplified compounds.

[C8]
1-1
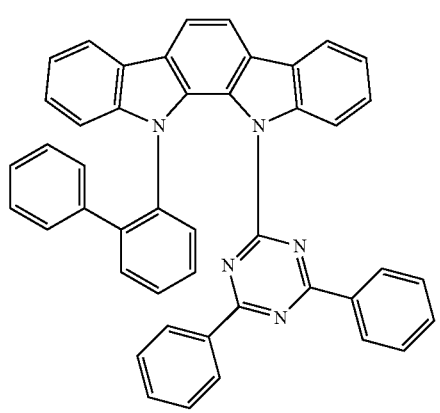
1-4
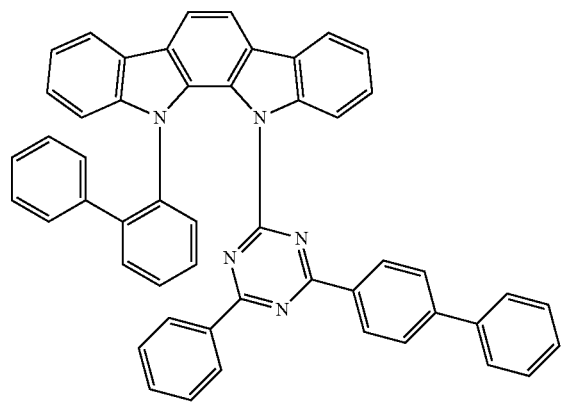
1-2
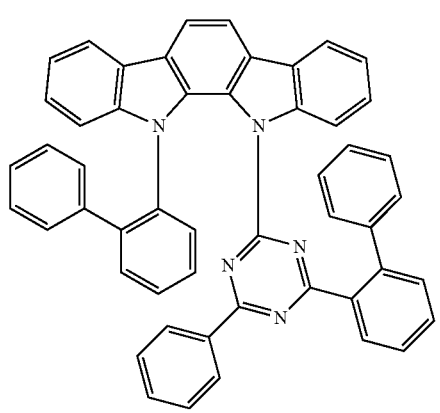
1-5
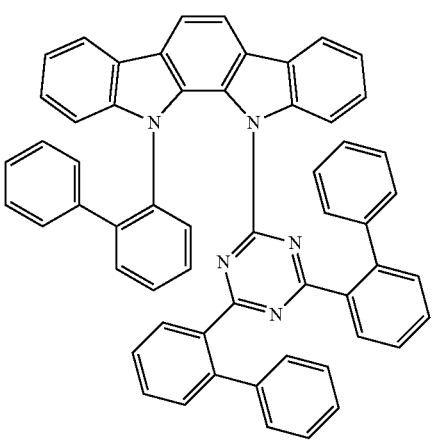
1-3
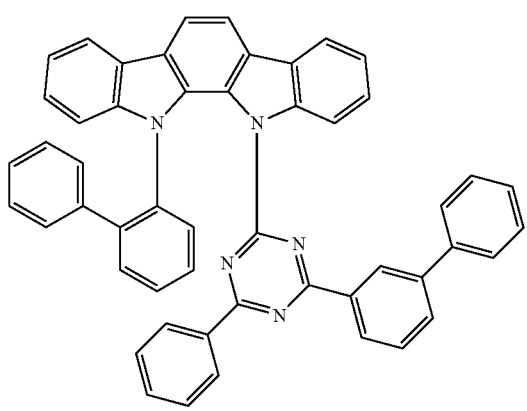
1-6
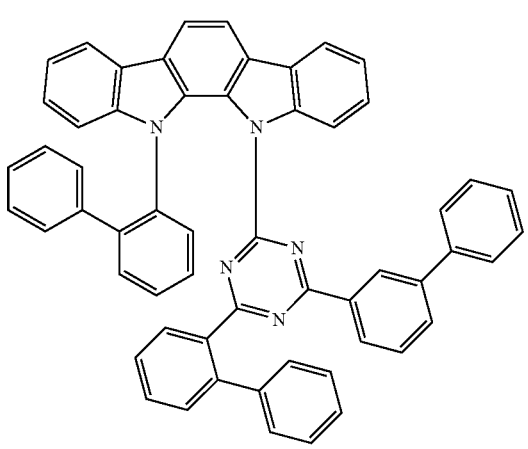

1-7
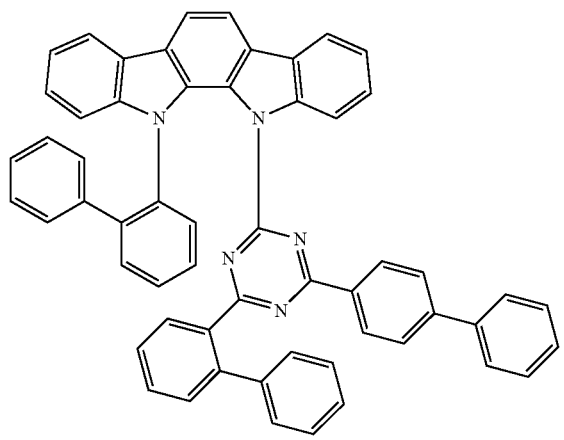
1-8
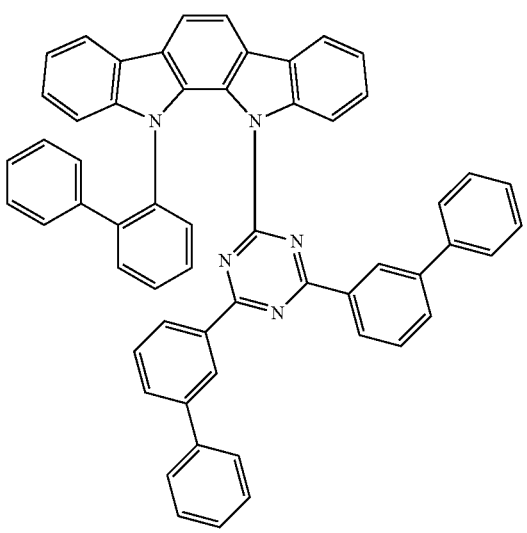
1-9
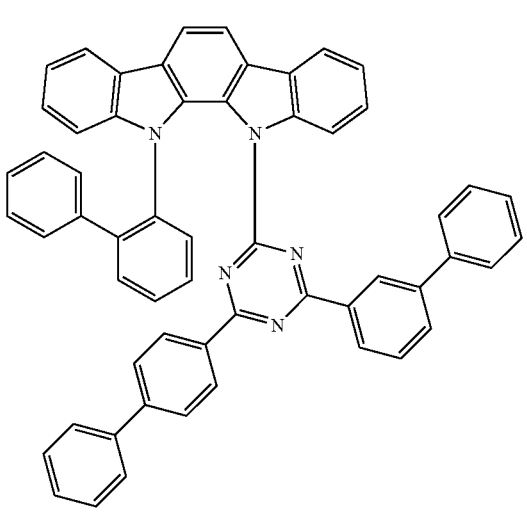
1-10
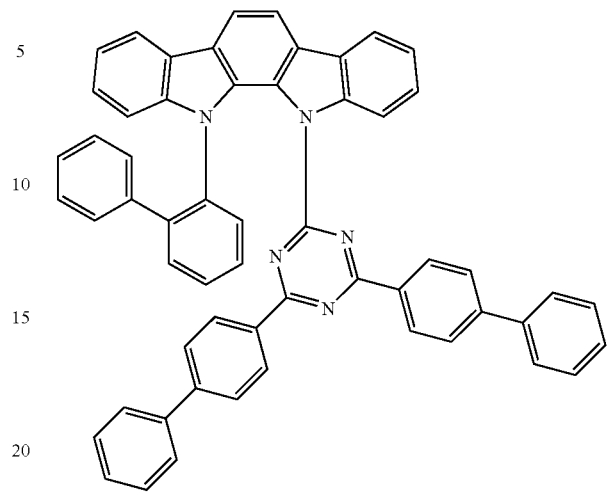
1-11
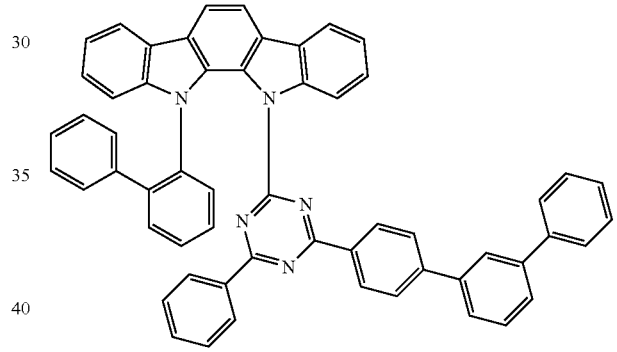
1-12
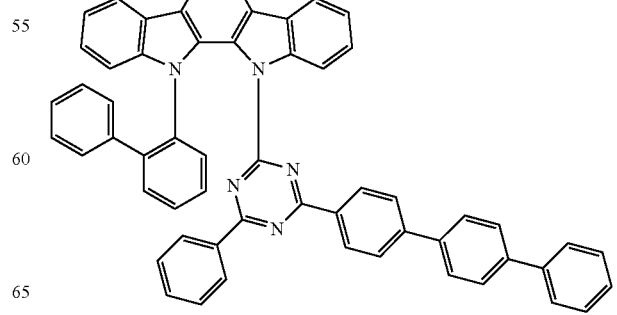

1-13
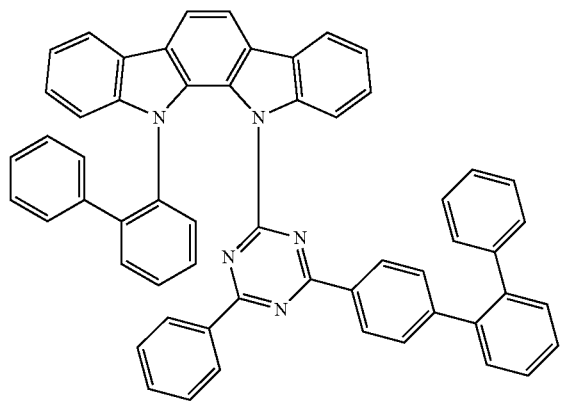
1-14
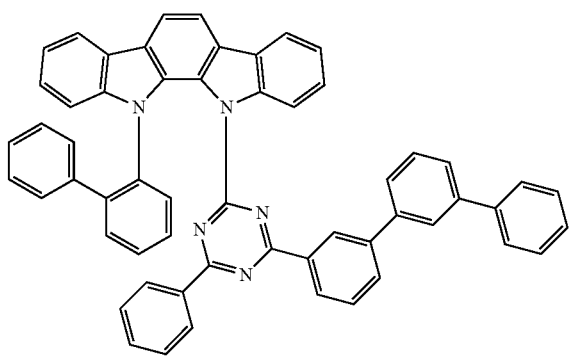
1-15
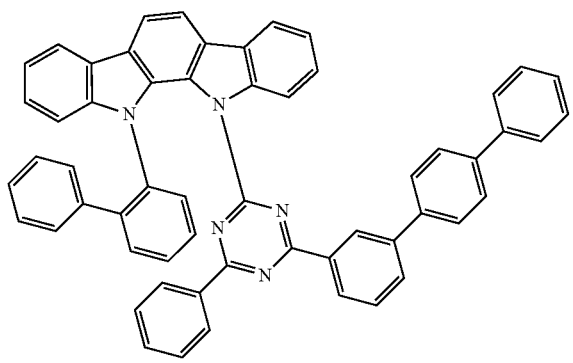
1-16
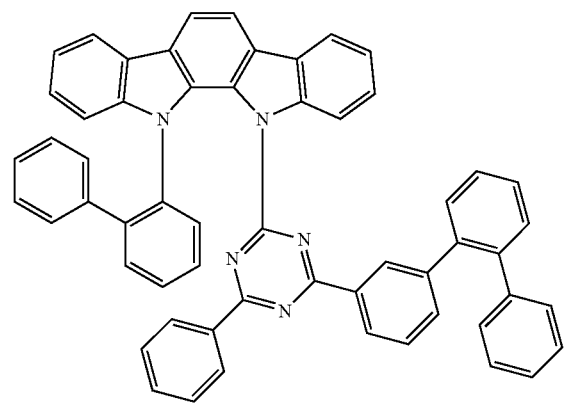
1-17
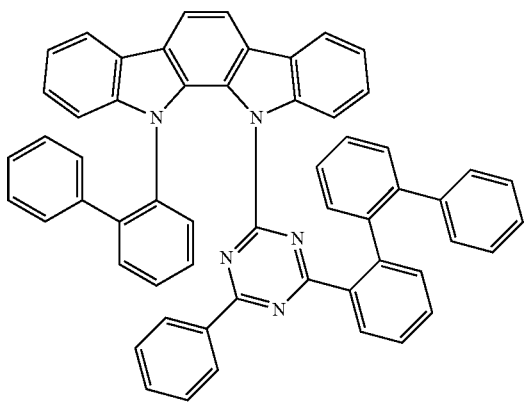
1-18
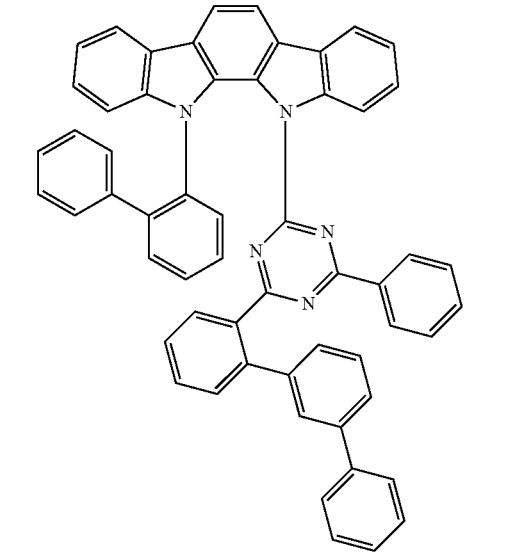
1-19

1-20
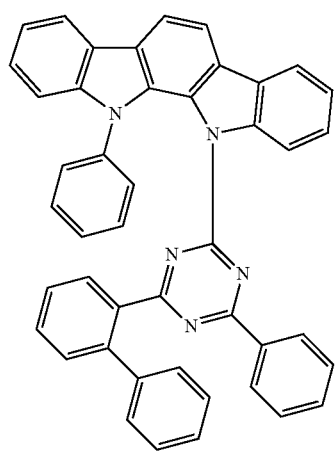
1-21
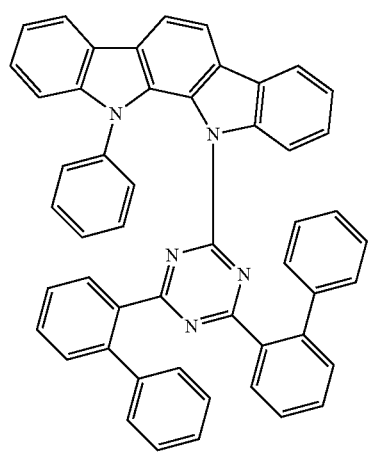
1-22
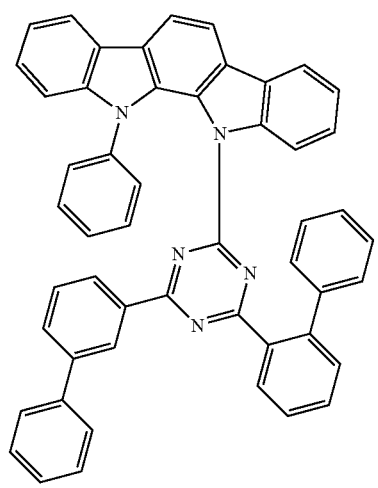
1-23
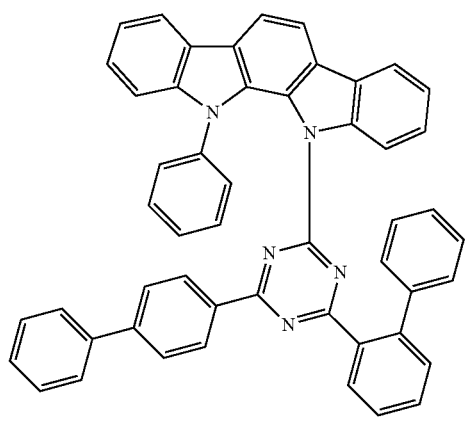
1-24
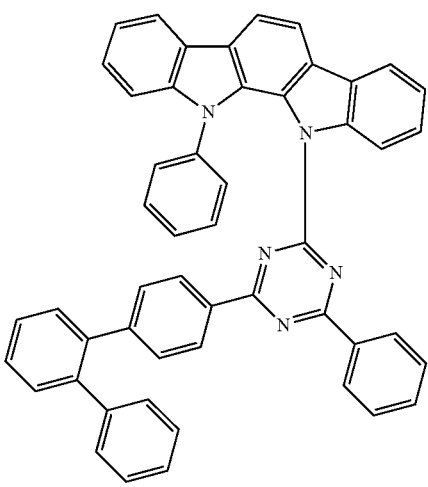
1-25
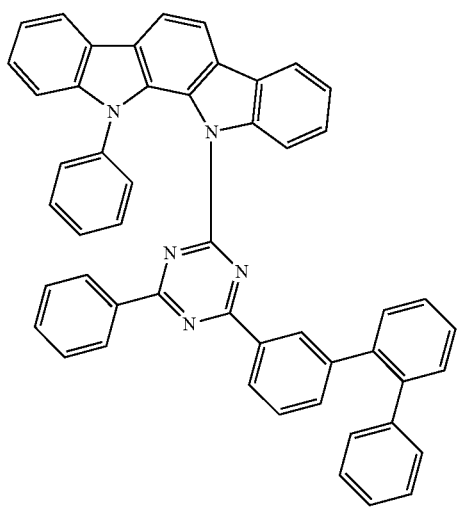

1-26
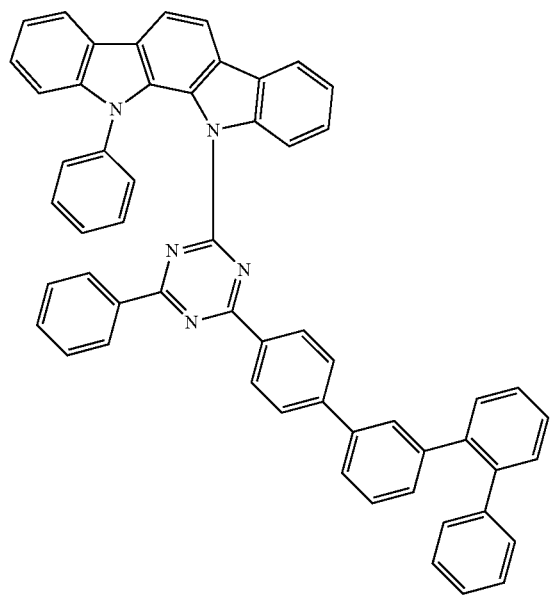
1-27
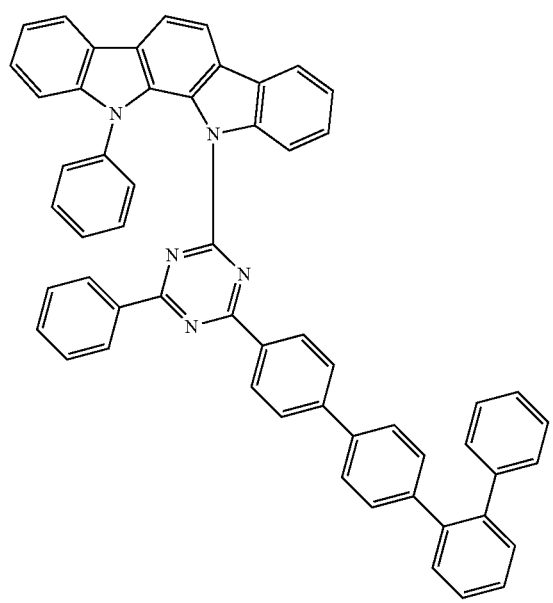
1-28
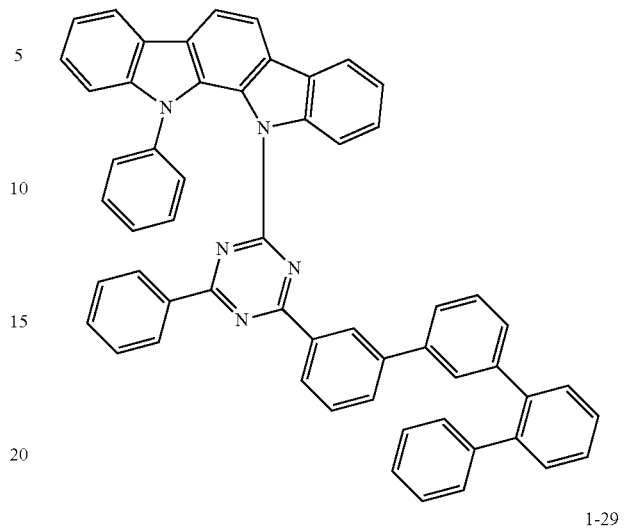
1-29
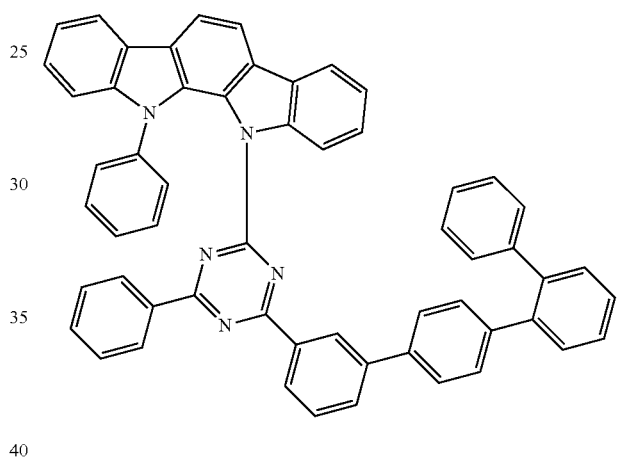
1-30
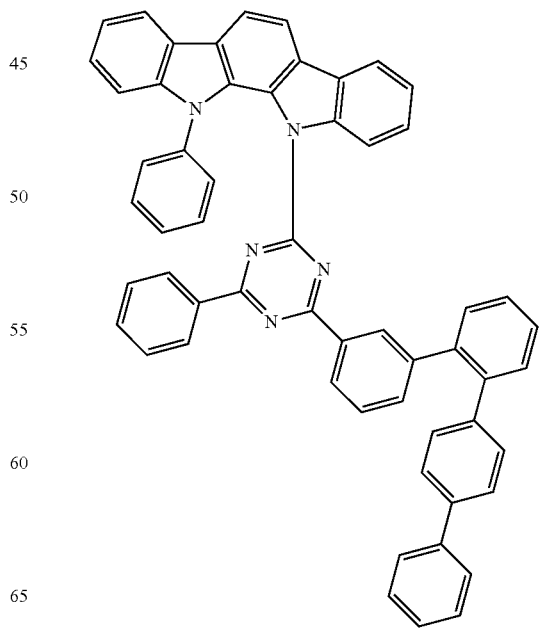

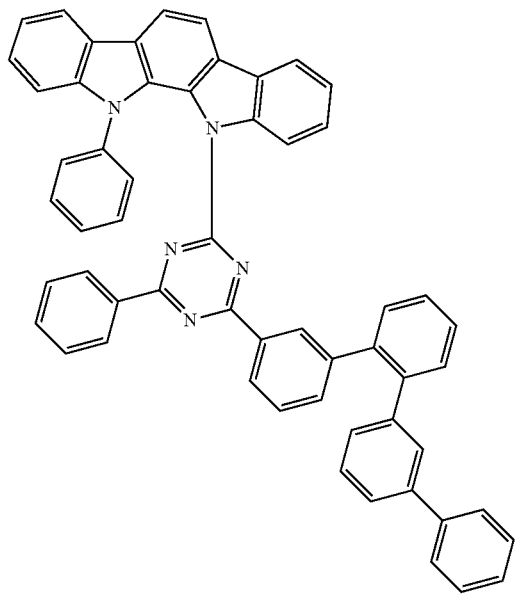
1-31
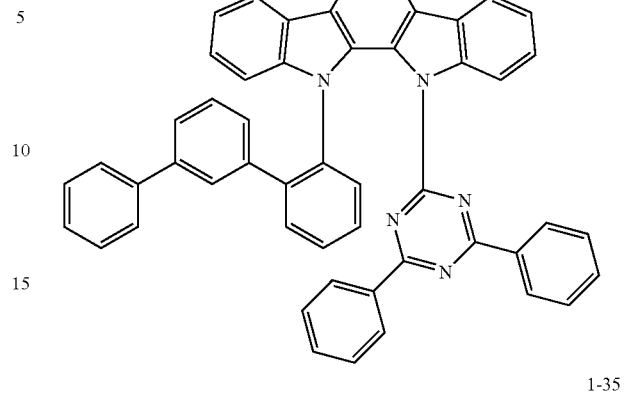
1-34
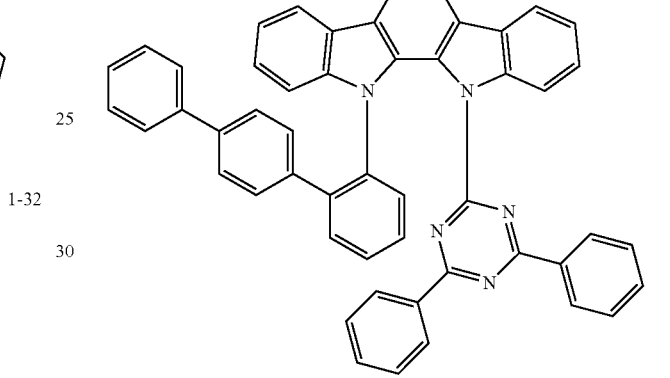
1-35
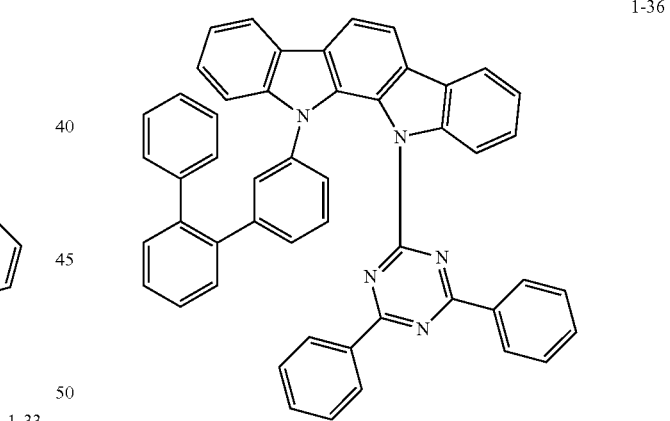
1-36
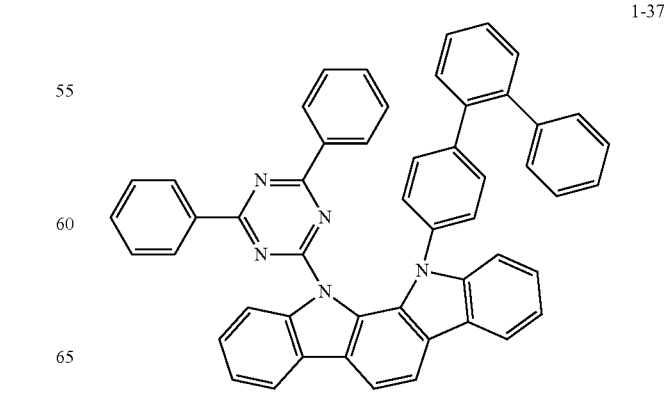
1-37

1-38
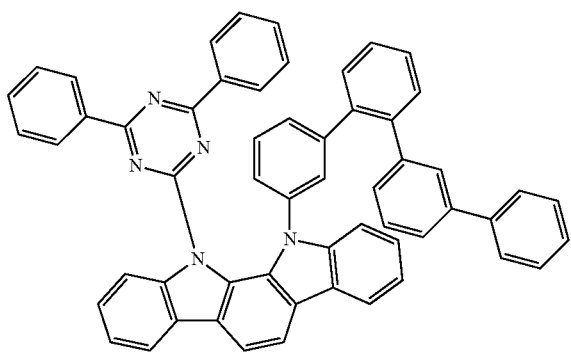
1-39
1-40
1-41
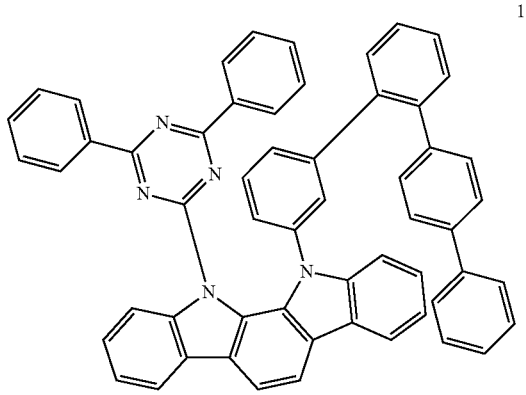
1-42
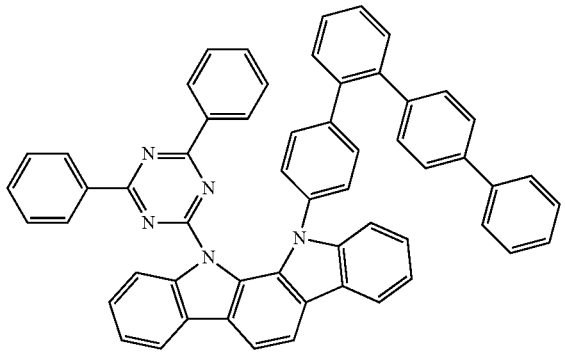
1-43
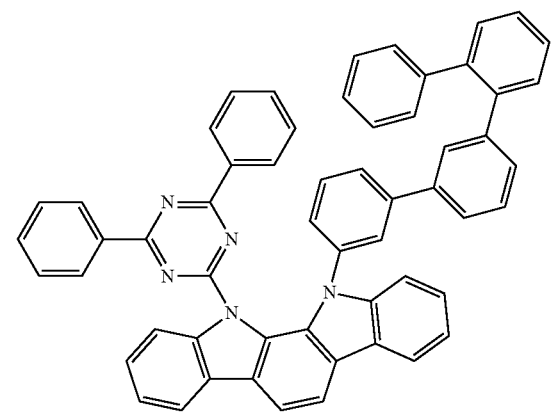
1-44
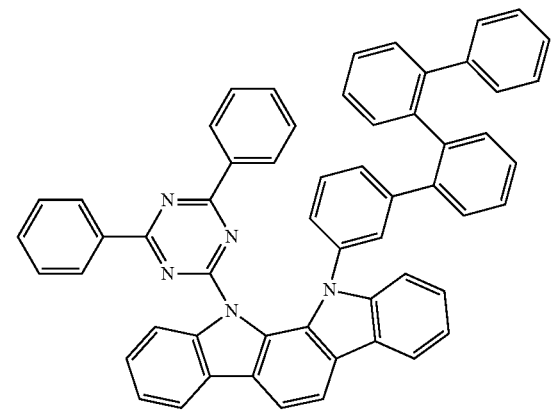

1-45
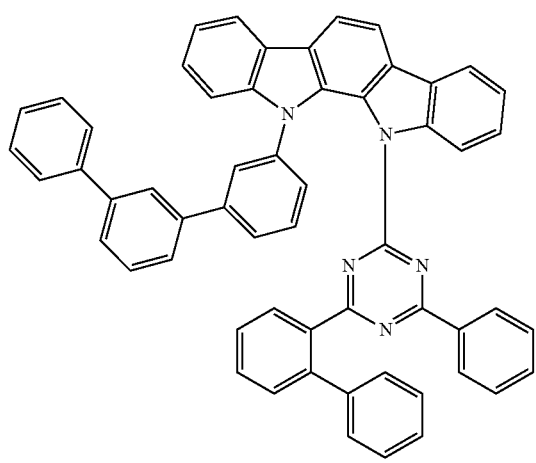
1-46
1-47
[C10]
1-48
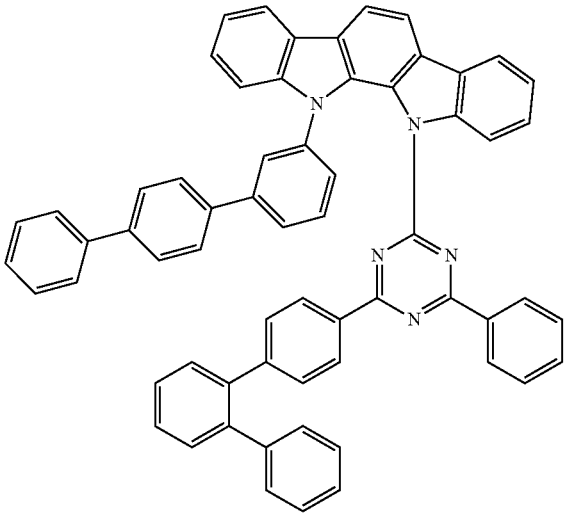
1-49
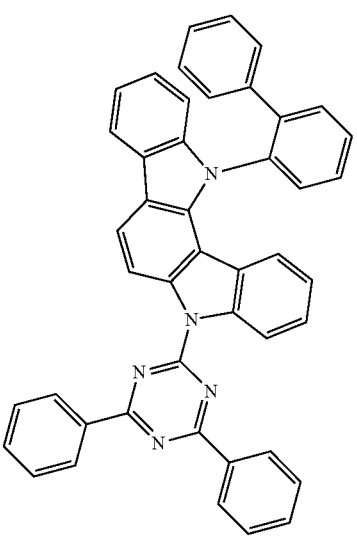
1-50
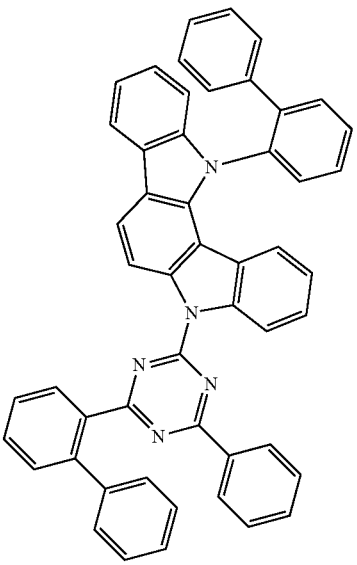

1-51
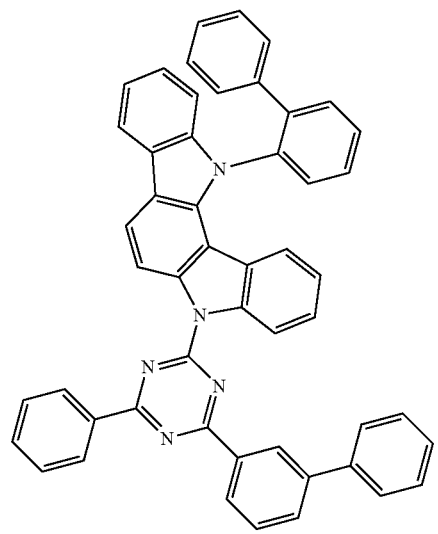
1-52
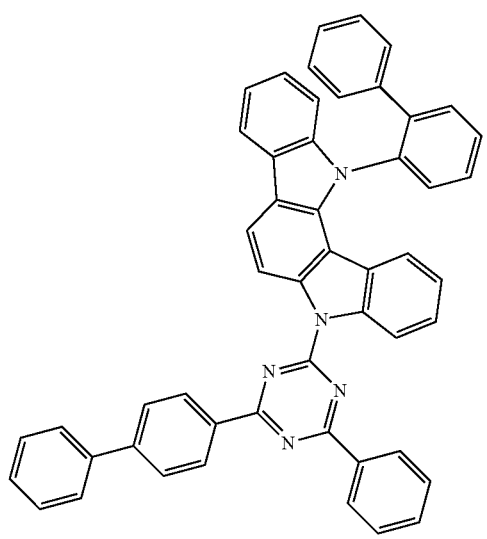
1-53
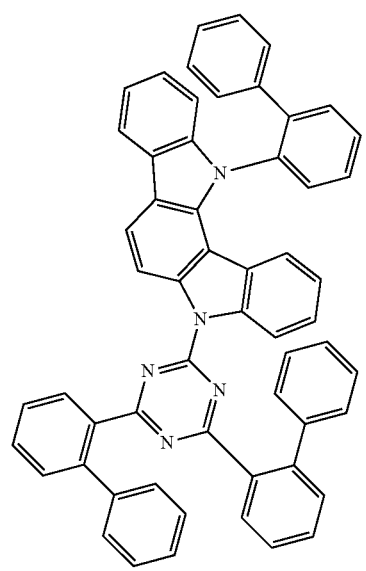
1-54
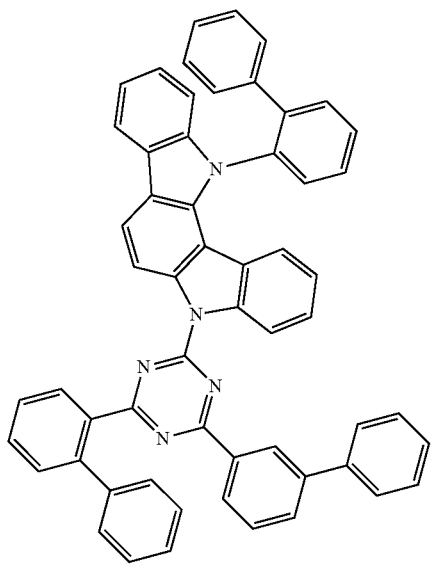
1-55
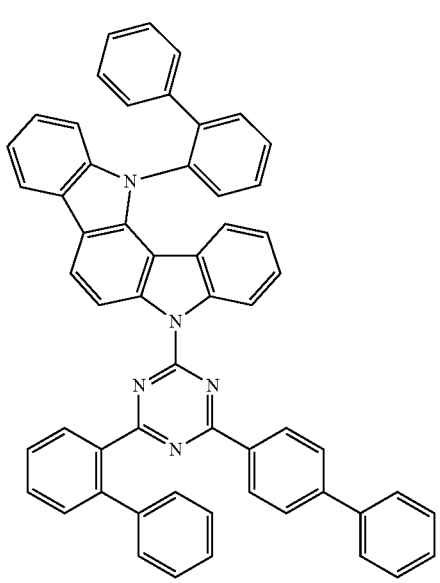

1-56
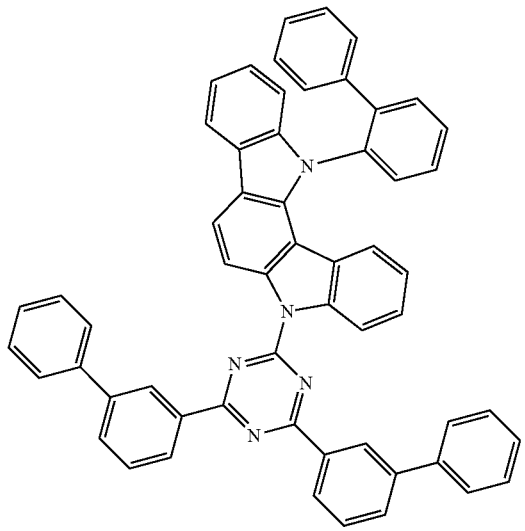
1-57
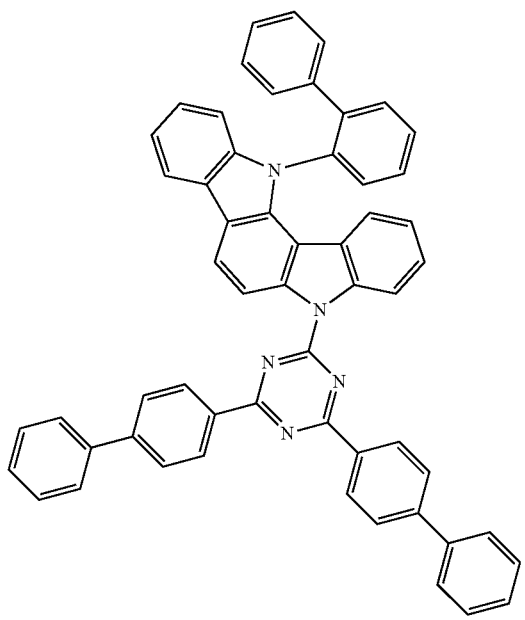
1-58
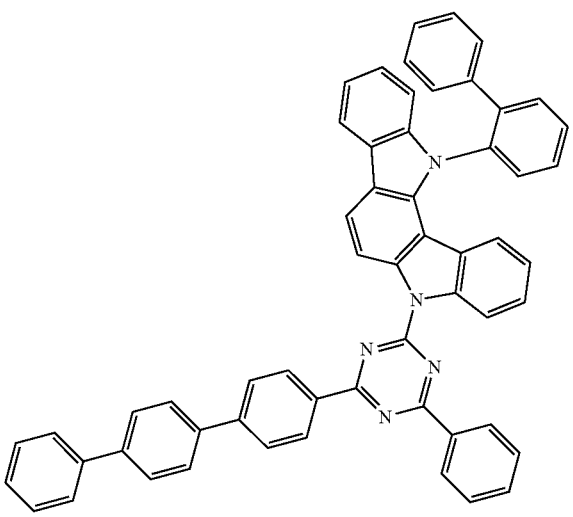
1-59
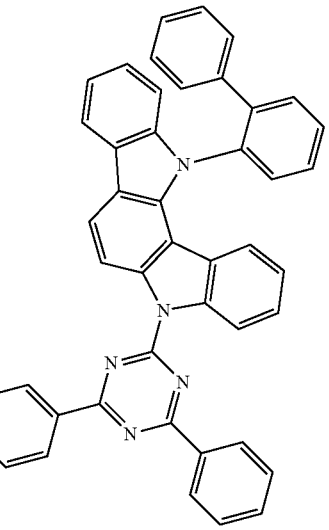
1-60
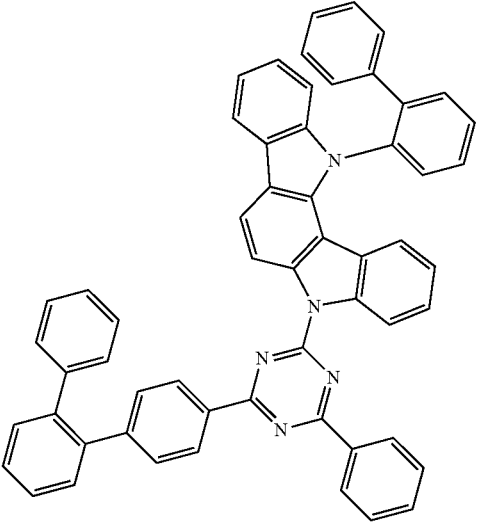

-continued
1-61
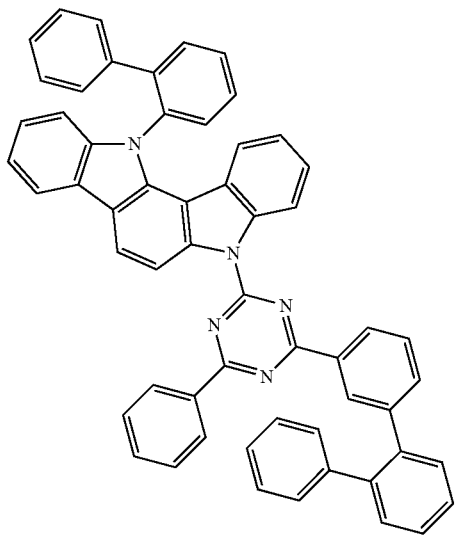
1-62
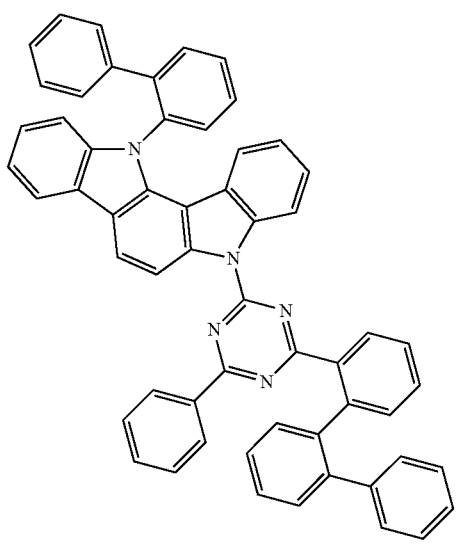
1-63
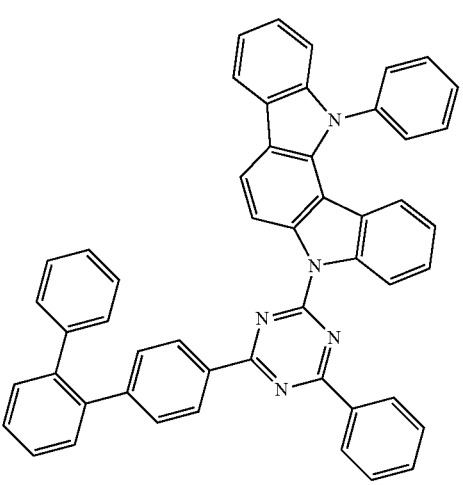
-continued
1-64
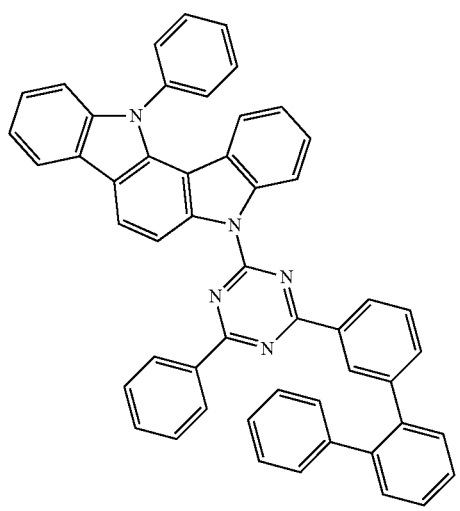
1-65
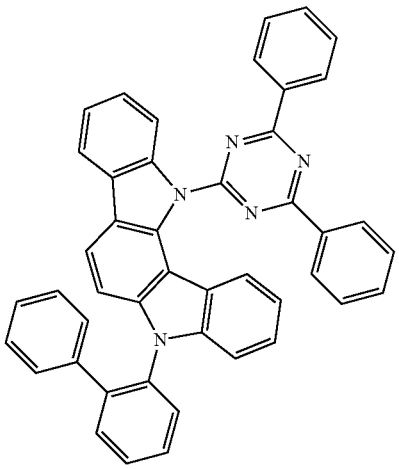
1-66
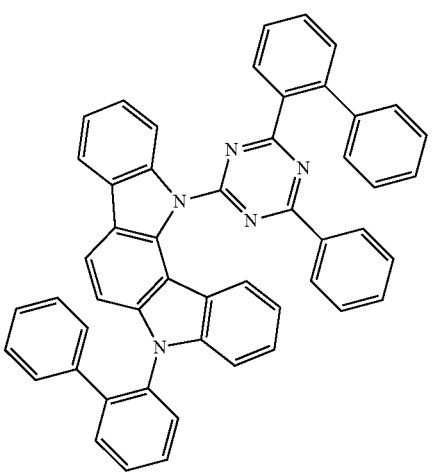

-continued
1-67
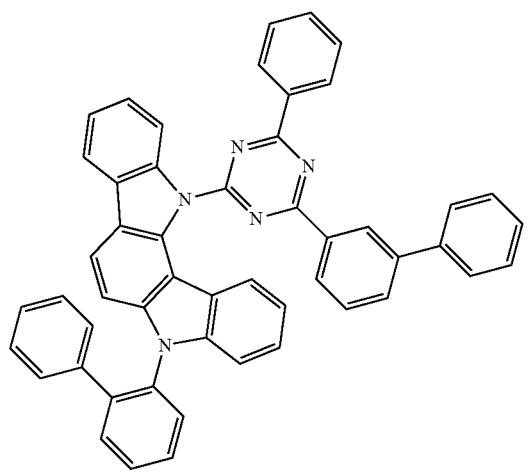
1-68
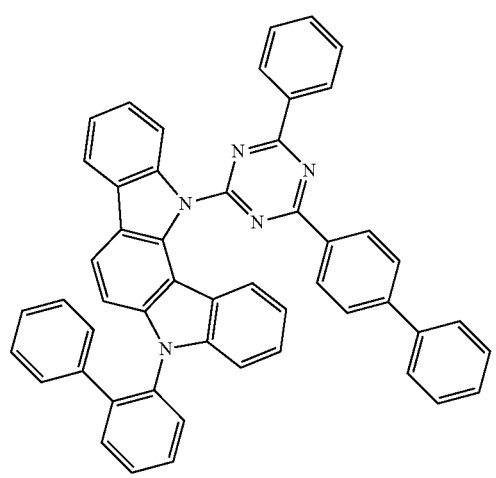
1-69
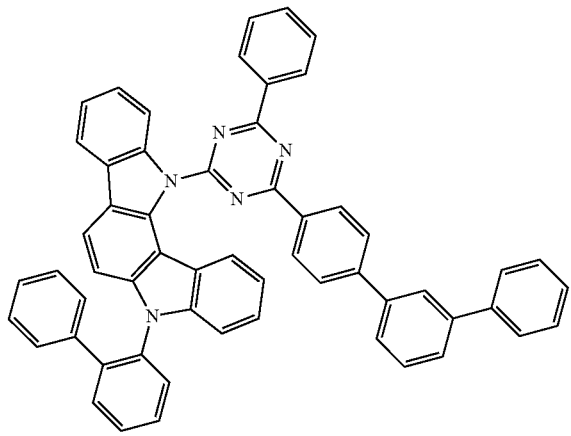
-continued
1-70
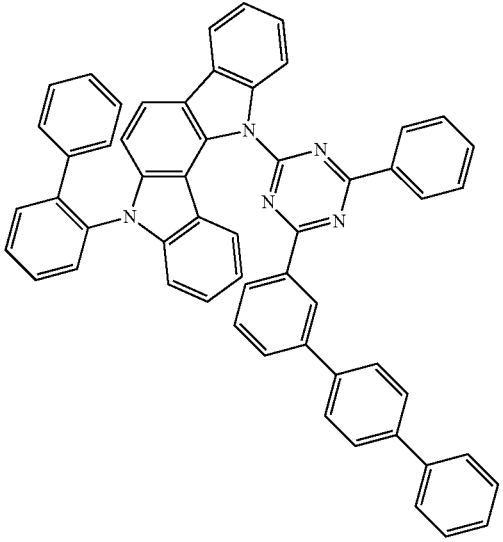
1-71
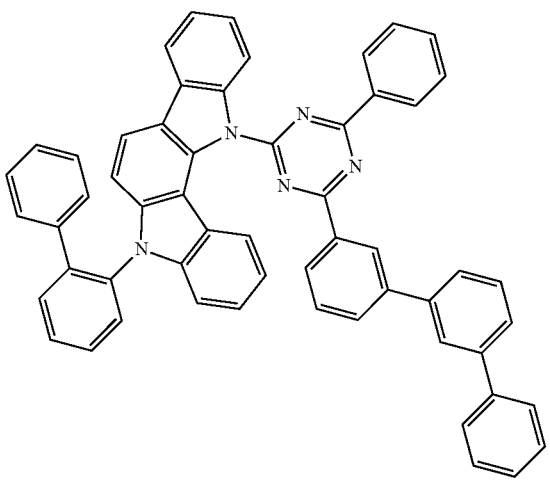
1-72
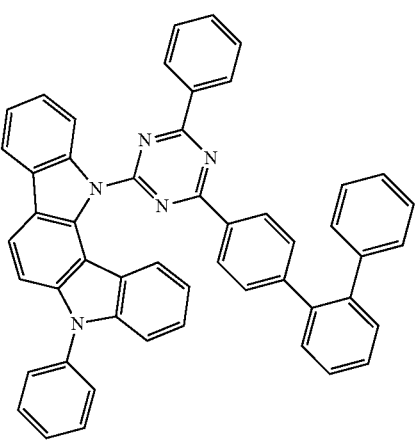

[C11]
1-73
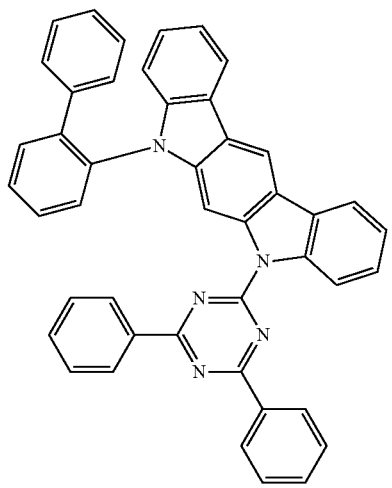
1-74
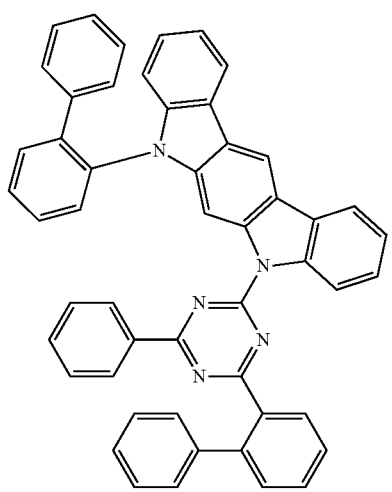
1-75
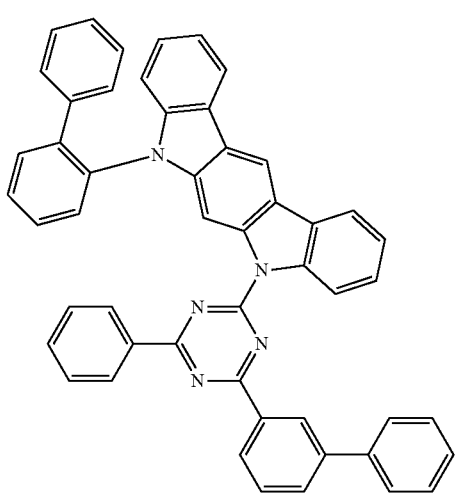
1-76
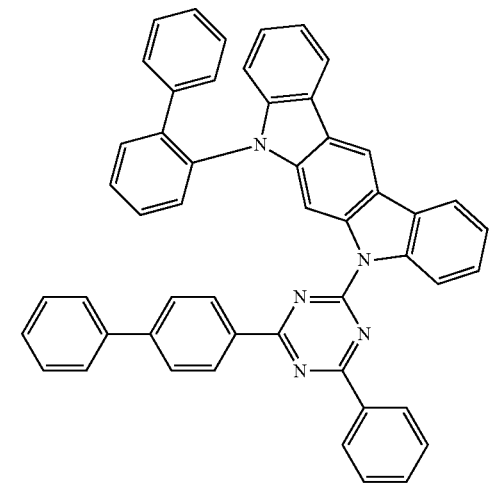
1-77
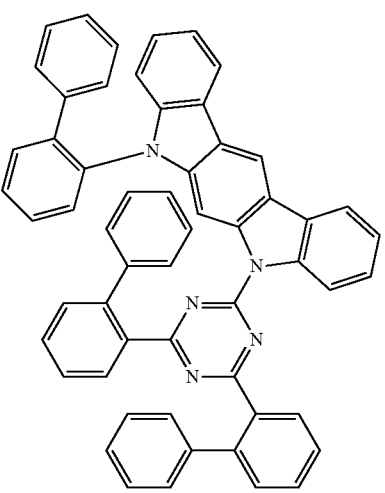
1-78
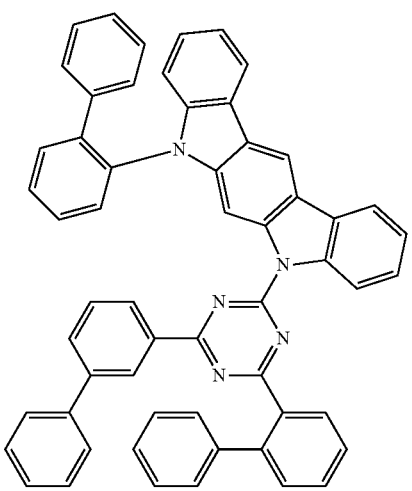

1-79
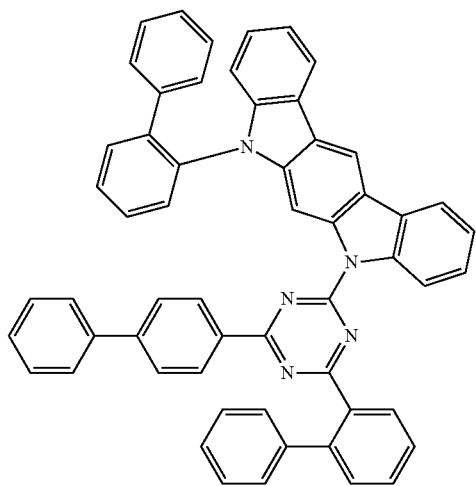
1-80
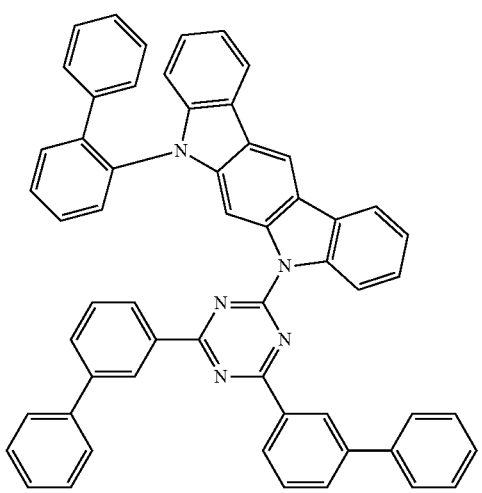
1-81
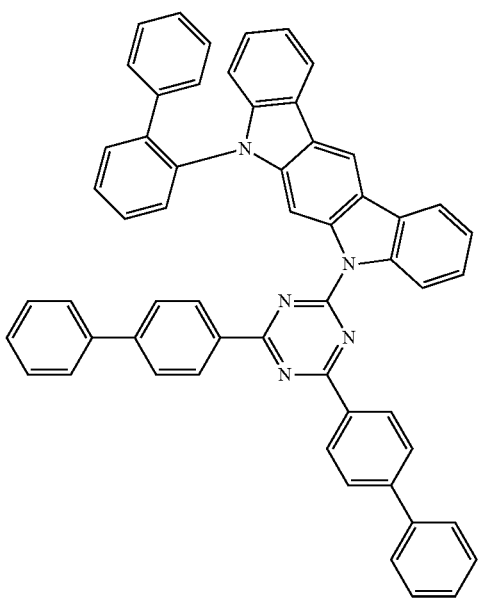
1-82
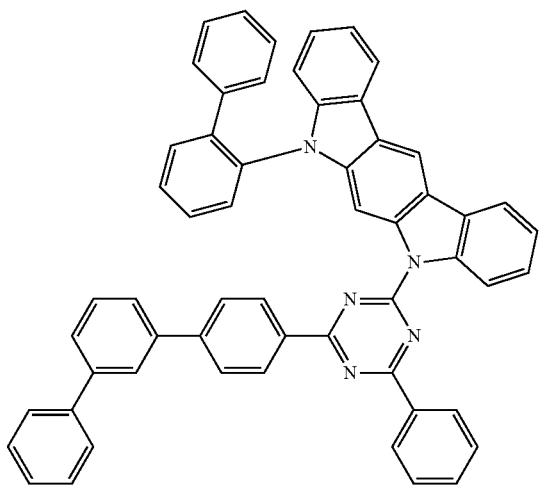
1-83
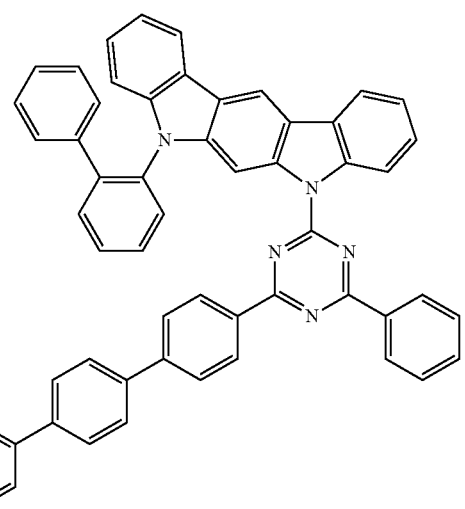
1-84
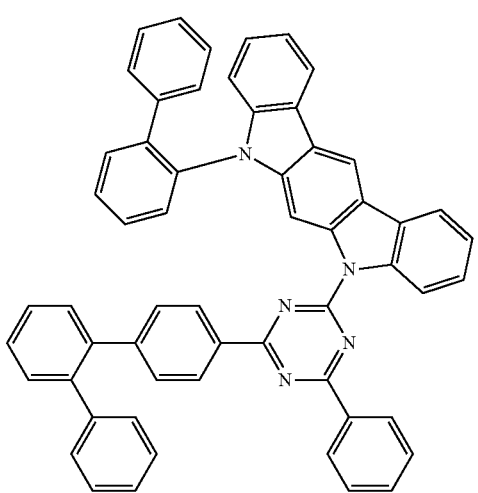

-continued
1-85
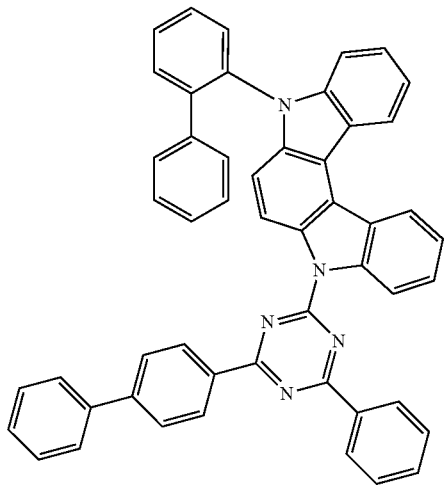
1-86
1-87
1-87b
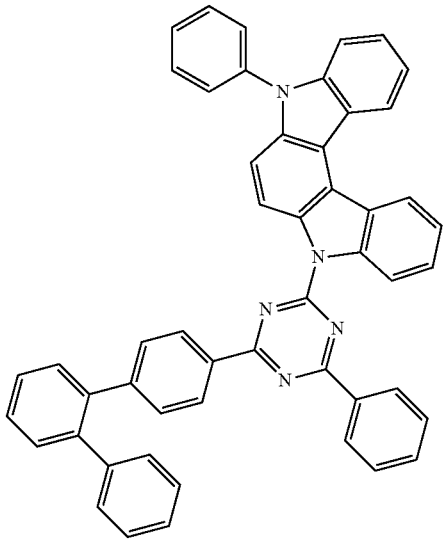
1-88
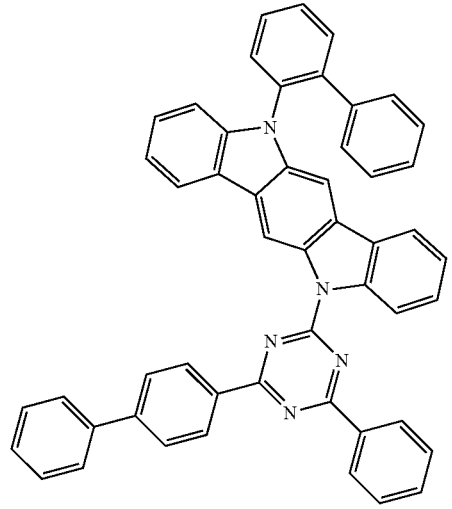
1-89
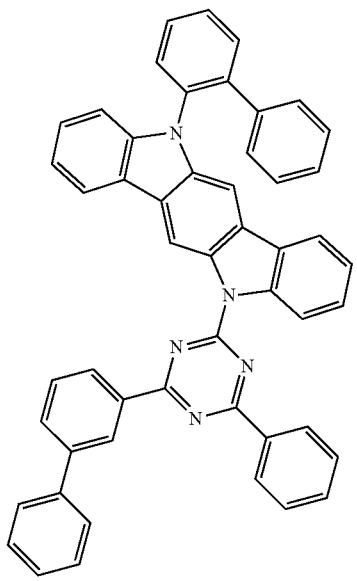

-continued
1-90
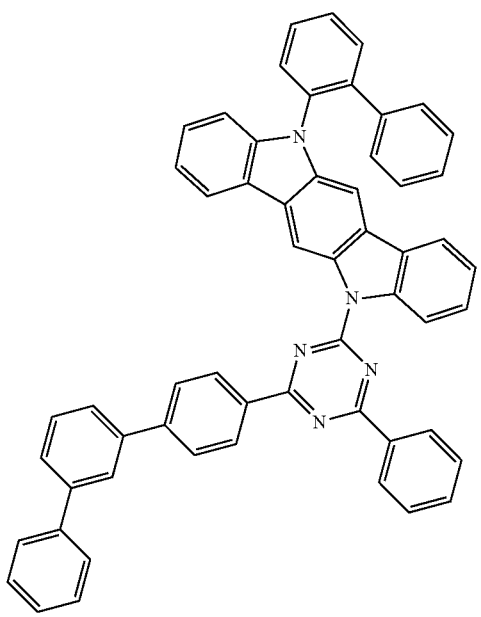
1-91
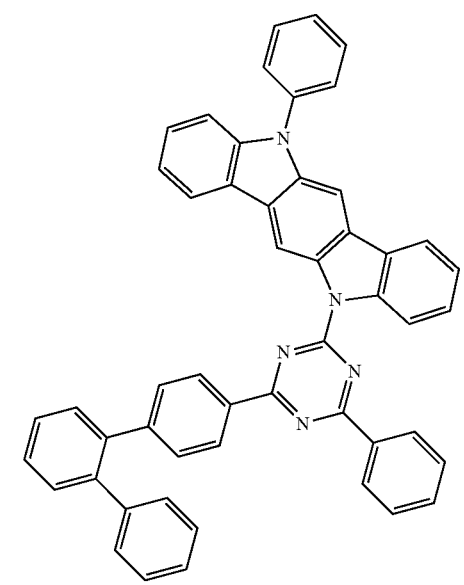
1-92
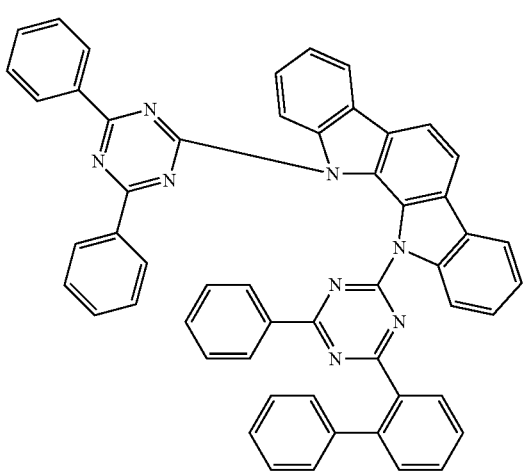
-continued
1-93
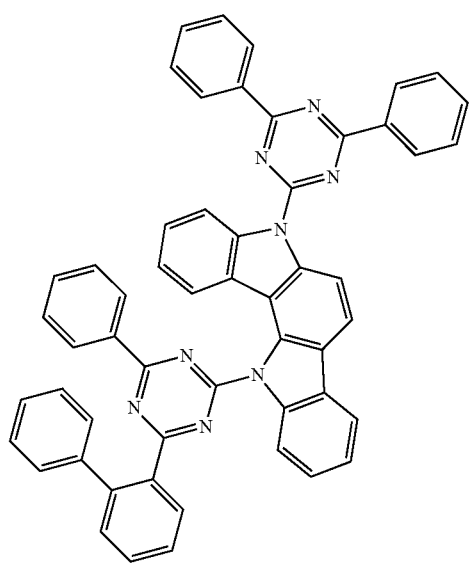
1-94
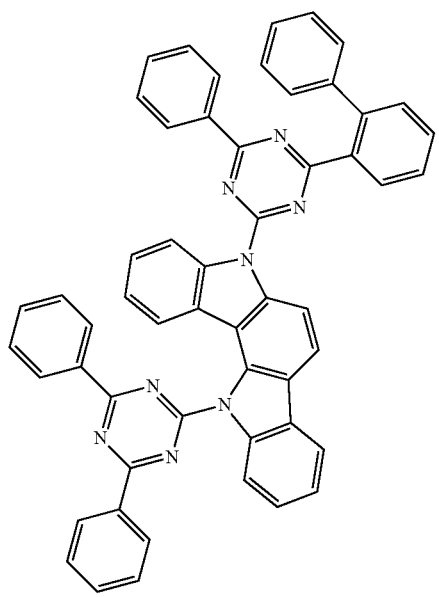
1-95
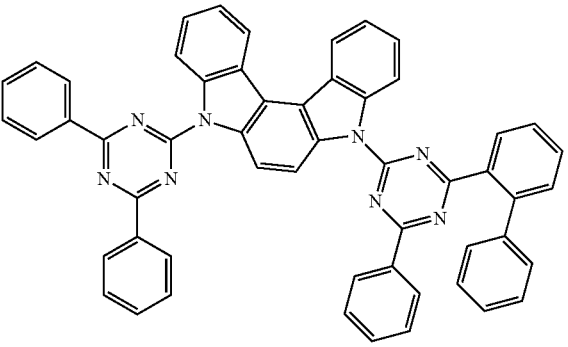

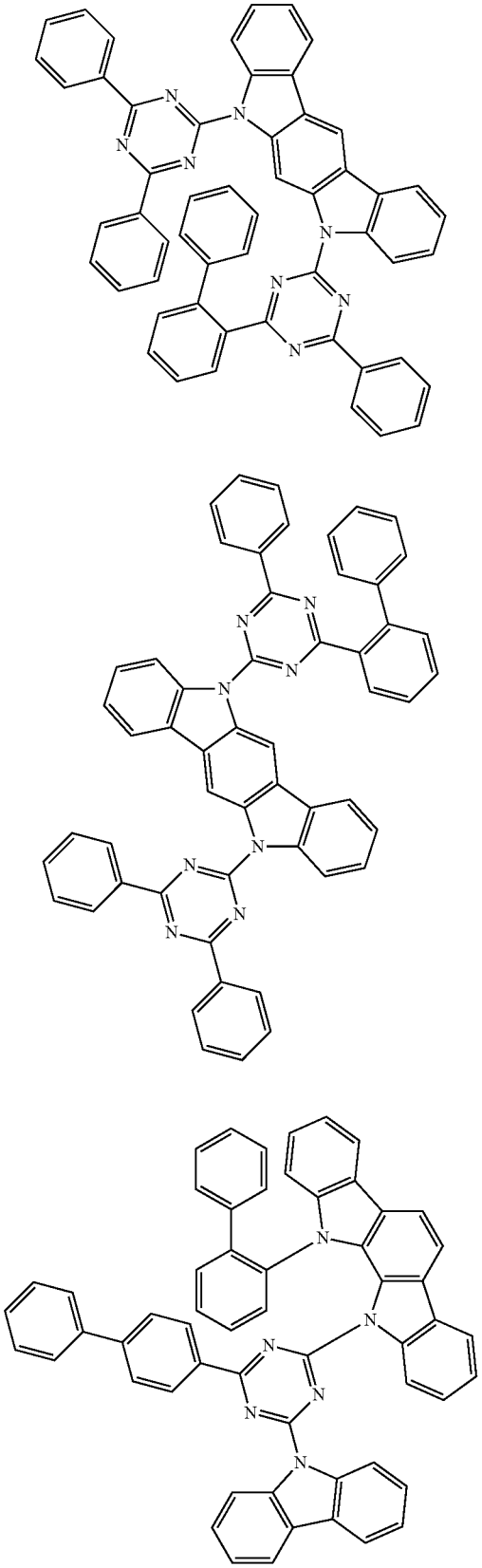
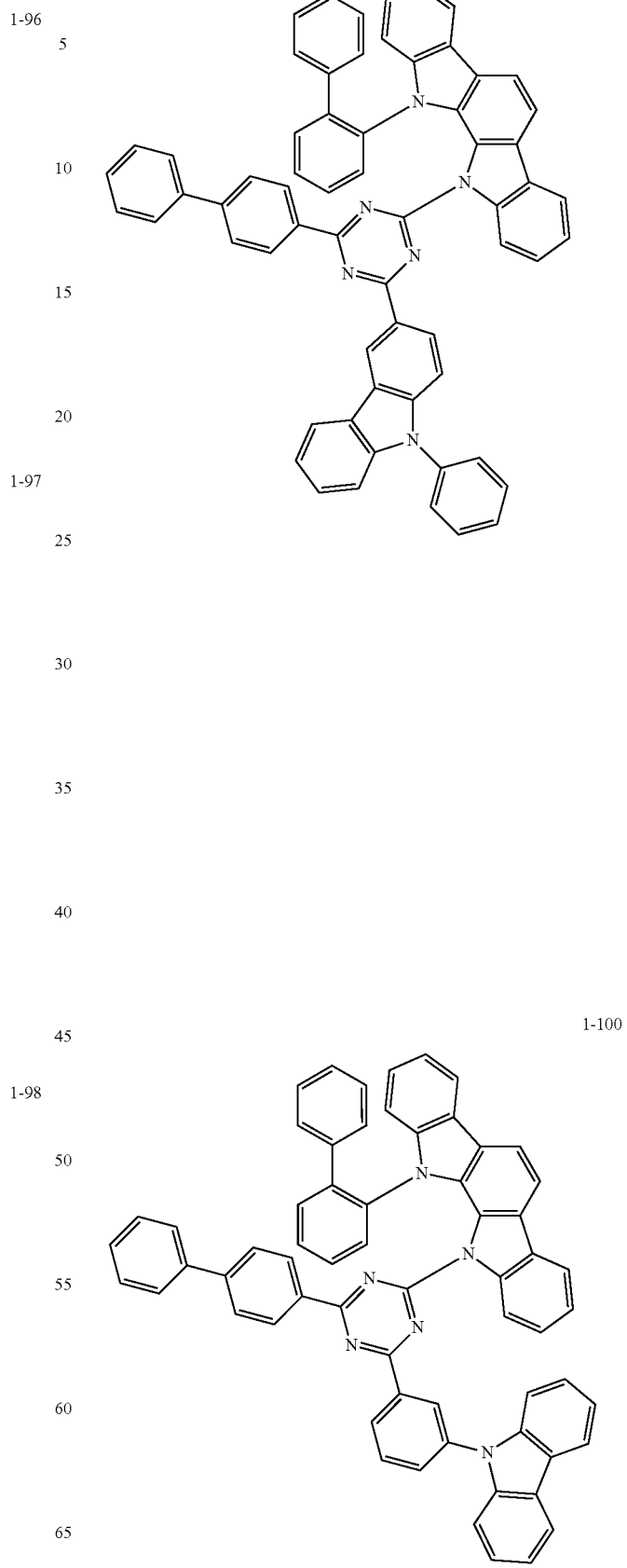

1-101
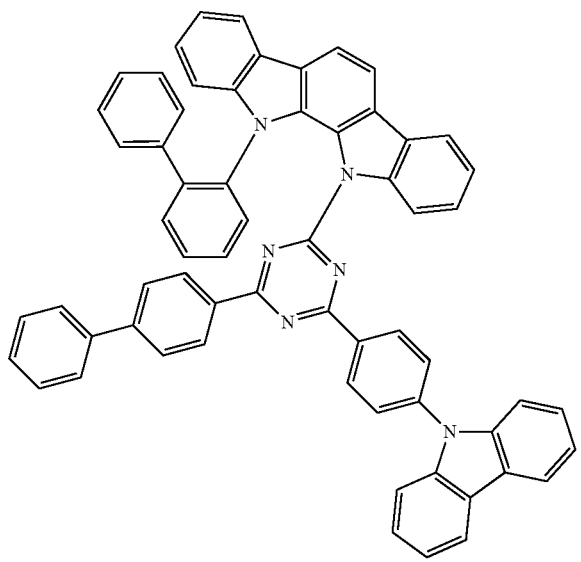
1-102
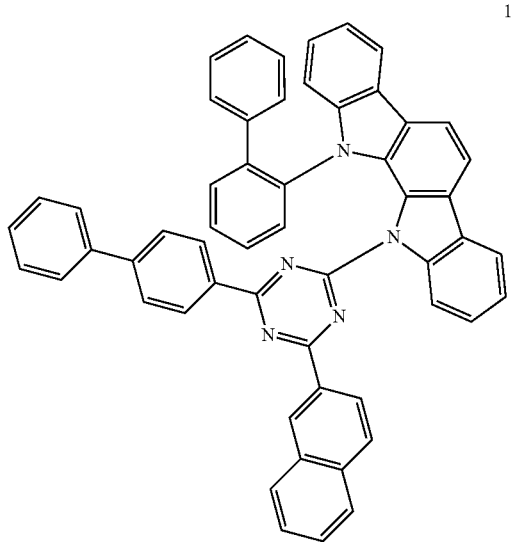
1-103
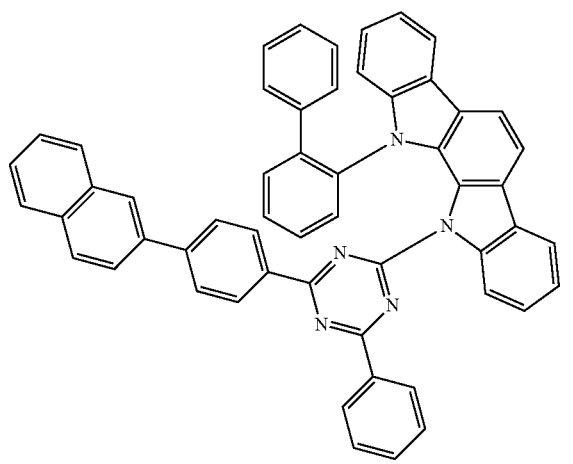
1-104
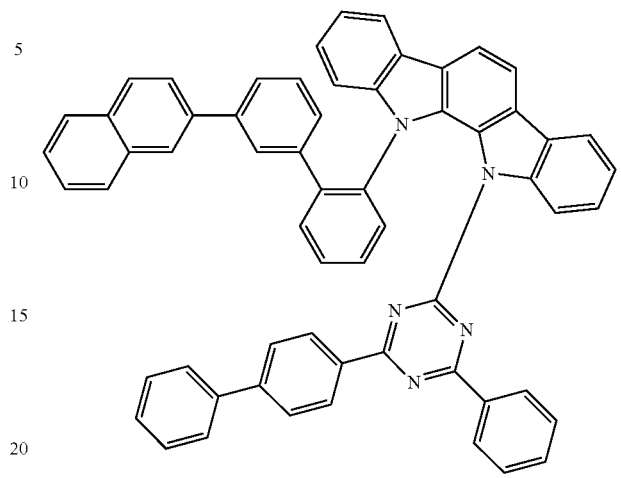
1-105
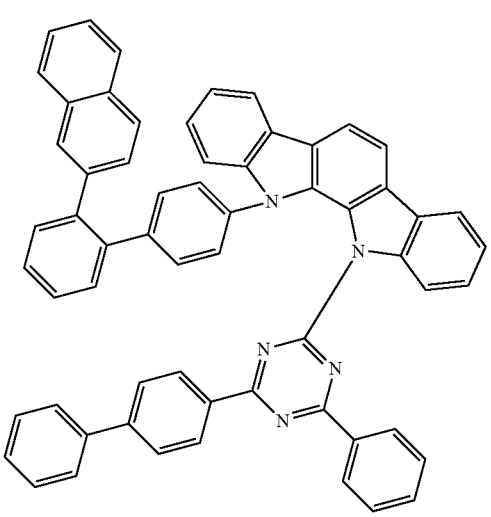
1-106
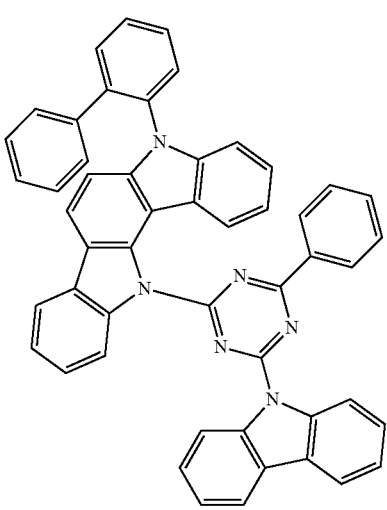

1-107
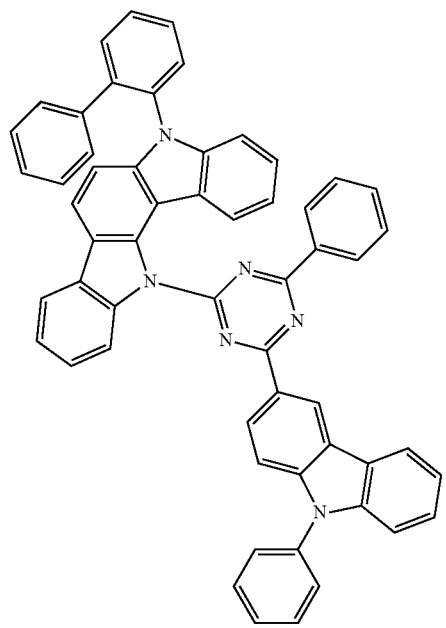
1-109
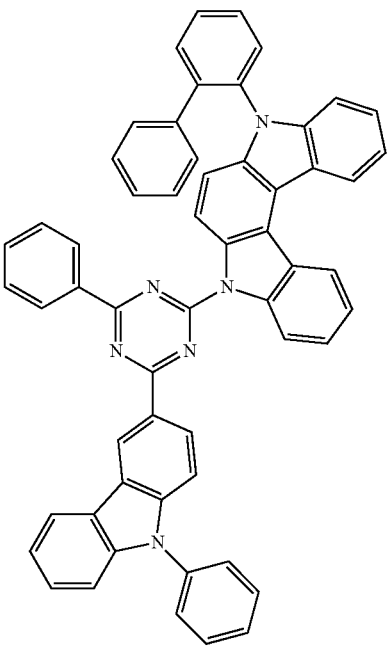
1-108
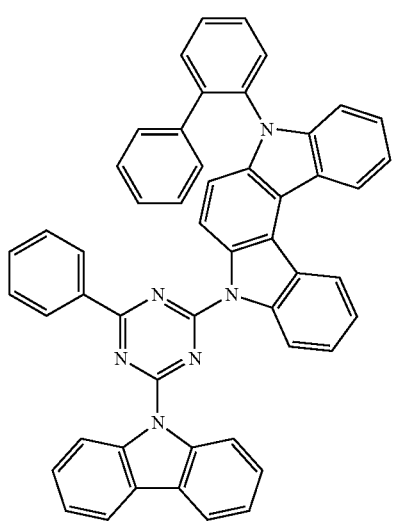
1-110
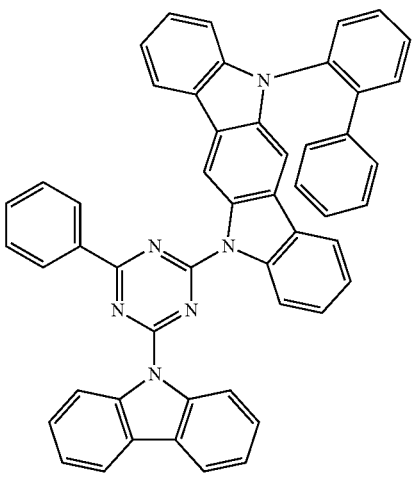

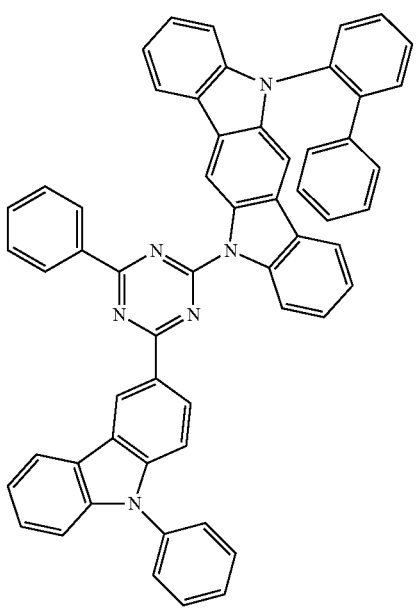

1-111

General Formula (2) which is the second host will be described.

In General Formula (2), $B^4$'s are independently hydrogen, an aromatic hydrocarbon group having 6 to 24 carbon atoms, or an aromatic heterocyclic group having 3 to 16 carbon atoms. It is preferable that $B^4$'s be independently hydrogen, an aromatic hydrocarbon group having 6 to 12 carbon atoms, or an aromatic heterocyclic group having 4 to 14 carbon atoms, and it is more preferable that $B^4$'s be independently an aromatic hydrocarbon group having 6 to 10 carbon atoms.

Specific examples of the above-described aromatic hydrocarbon group having 6 to 24 carbon atoms or aromatic heterocyclic group having 3 to 16 carbon atoms include aromatic groups formed by removing one H from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, benzothiadiazole, dibenzofuran, dibenzothiophene, dibenzoselenophene, or carbazole. Preferred examples thereof include aromatic groups formed from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, or benzothiadiazole. More preferred examples thereof include aromatic groups formed from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, or oxadiazole.

j represents a number of repetitions and represents an integer of 1 to 6 and preferably an integer of 1 to 3.

In the present specification, in a case where the number of repetitions is 2 or more, repeating units thereof may be the same as or different from each other.

R's independently represent hydrogen, an alkyl group having 1 to 20 carbon atoms, an acyl group having 2 to 20 carbon atoms, an alkoxy group having 2 to 20 carbon atoms, an aromatic hydrocarbon group having 6 to 24 carbon atoms, or an aromatic heterocyclic group having 3 to 16 carbon atoms, but are not a carbazole ring group. Hydrogen, an aromatic hydrocarbon group having 6 to 24 carbon atoms, or an aromatic heterocyclic group having 3 to 16 carbon atoms is preferable.

f, g, h, and i represent numbers of substitutions and each independently represent an integer of 1 to 3, and an integer of 1 or 2 is preferable.

X's independently represent N, C—R', or C—, and N or C—H is preferable. More preferably, all X's are C—H, or C—H and N. R' represents hydrogen, an alkyl group having 1 to 20 carbon atoms, an alkoxy group having 1 to 20 carbon atoms, or a diarylamino group having 12 to 44 carbon atoms.

Preferred specific examples of compounds represented by General Formula (2) will be shown below, but the present invention is not limited thereto.

[C13]

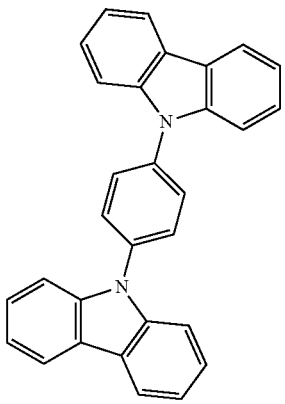

2-1

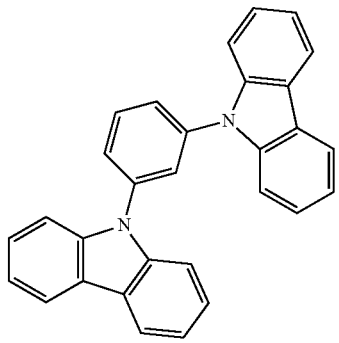

2-2

2-3
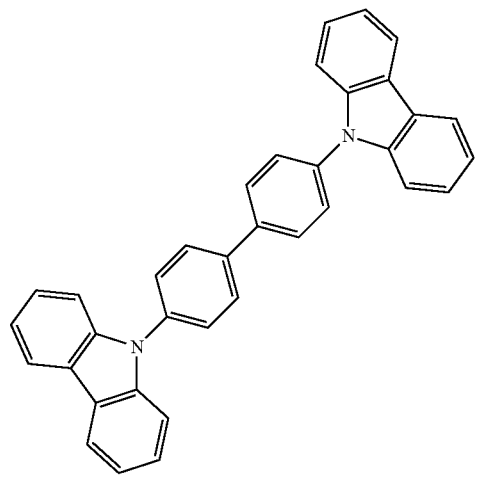
2-6
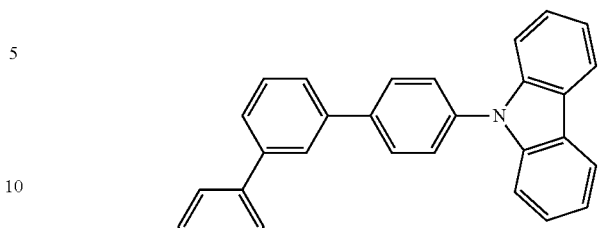
2-7
2-4
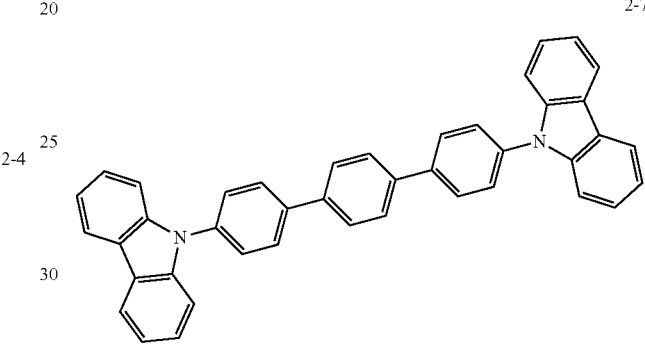
2-8
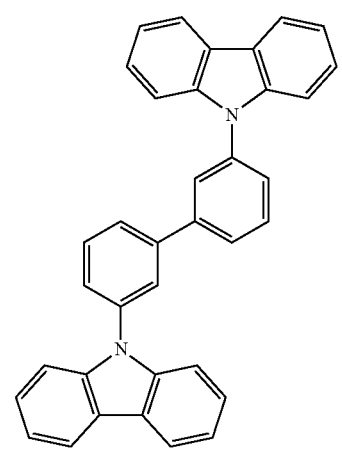
2-5
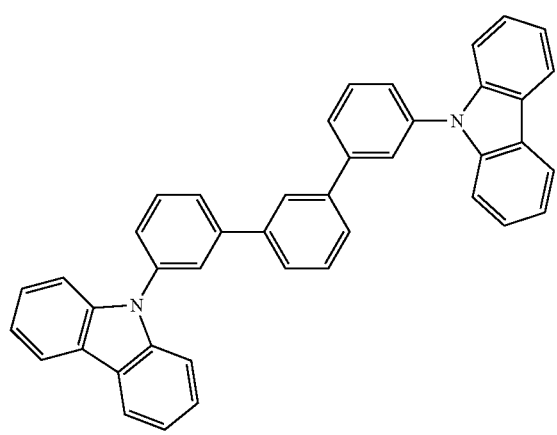
2-9
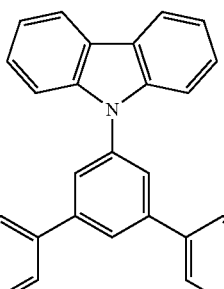

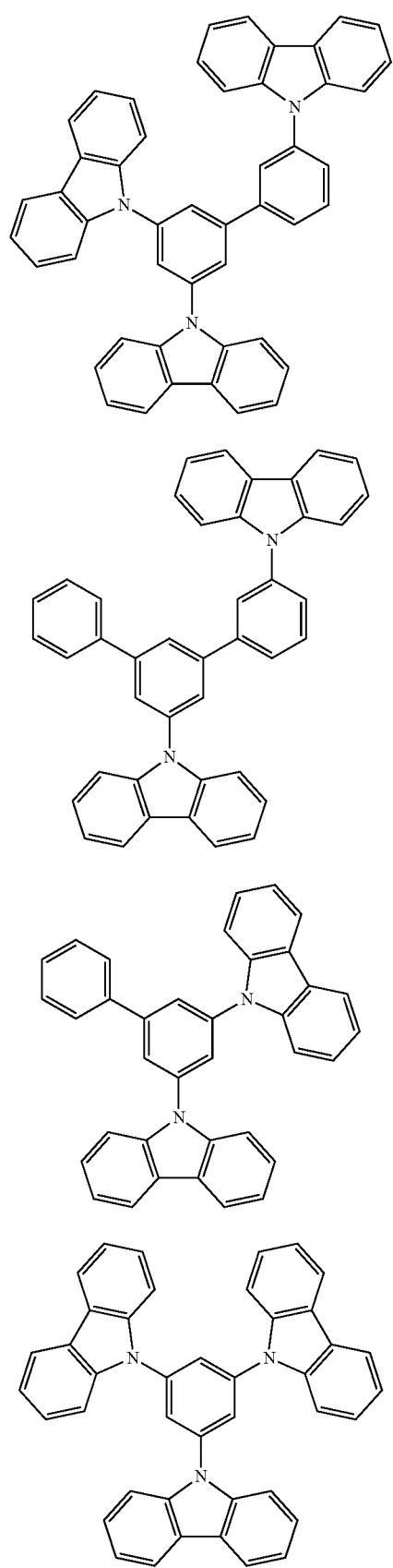
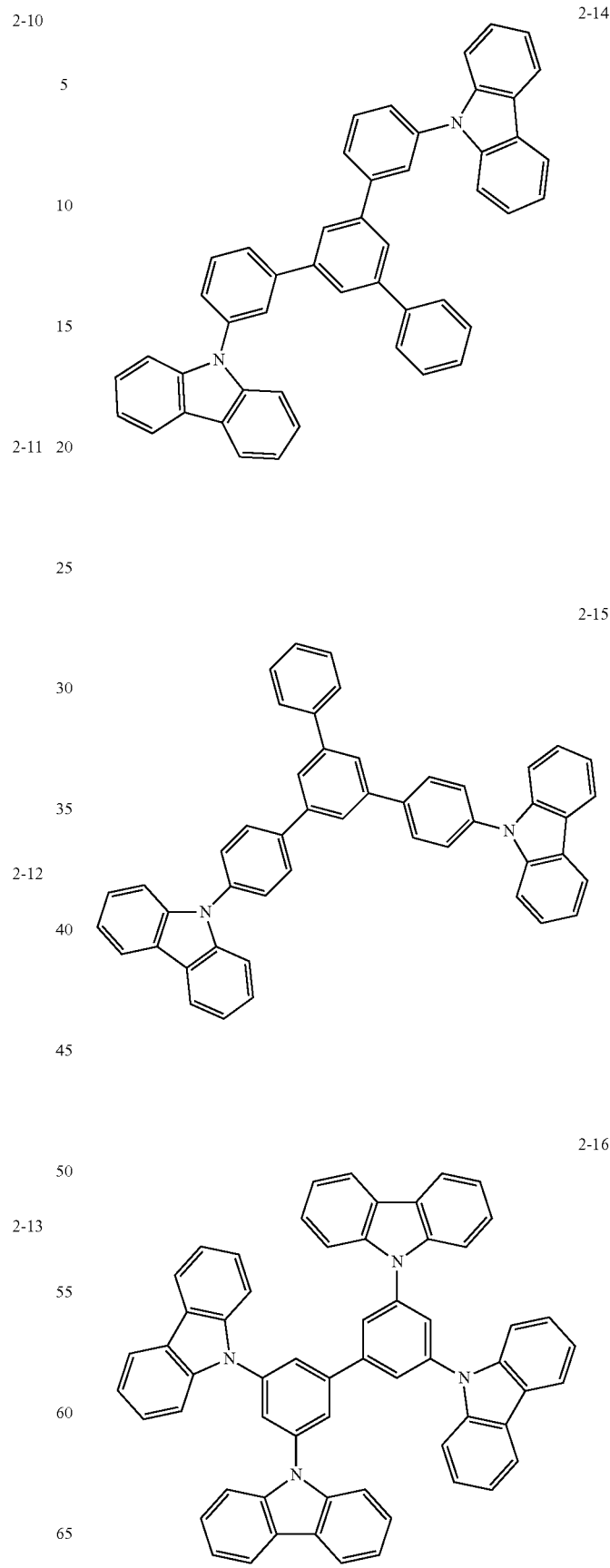

2-17 [C14]
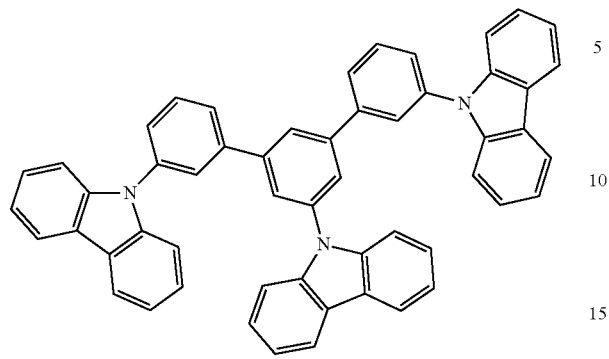
2-18
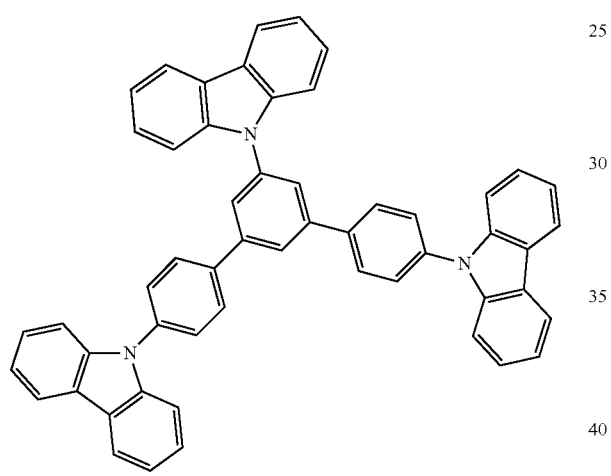
2-19
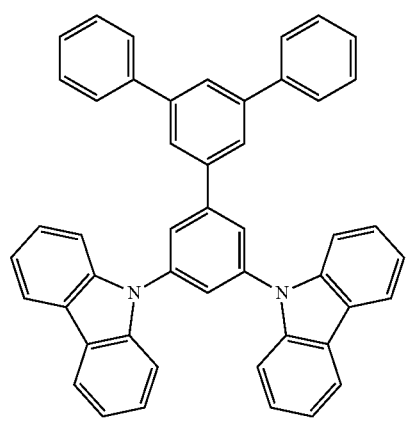
2-20
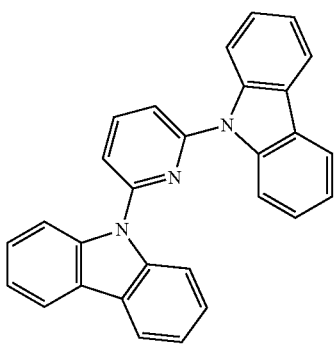
2-21
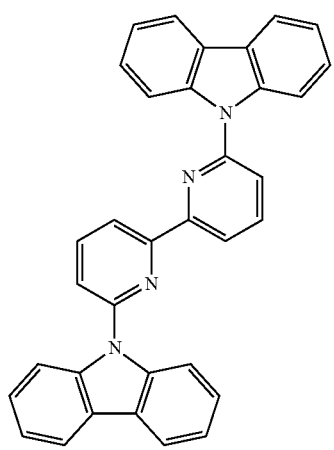
2-22
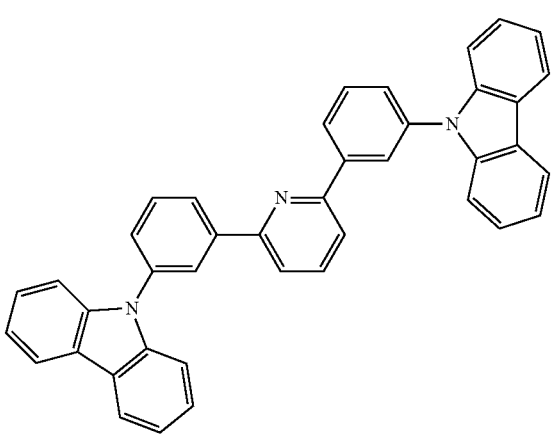

2-23
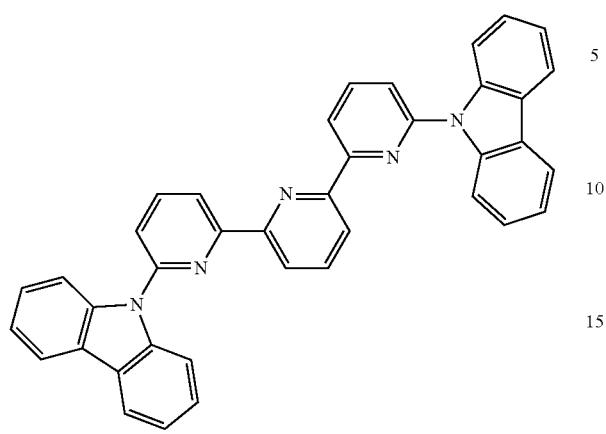
2-24
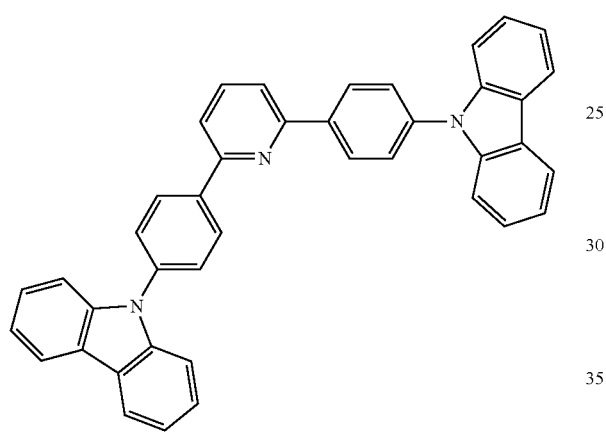
2-25
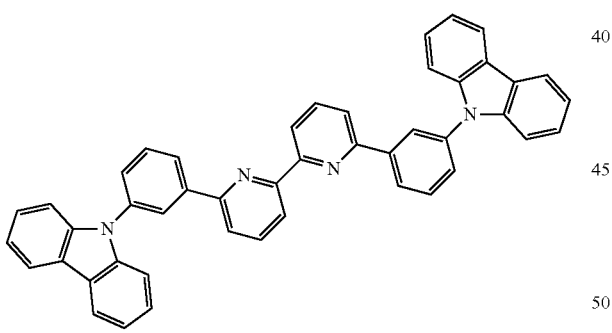
2-26
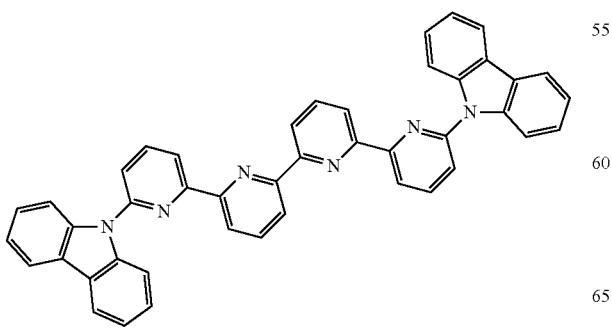
2-27
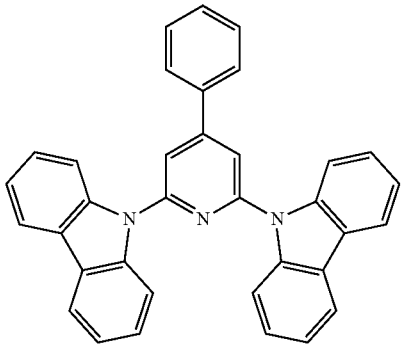
2-28
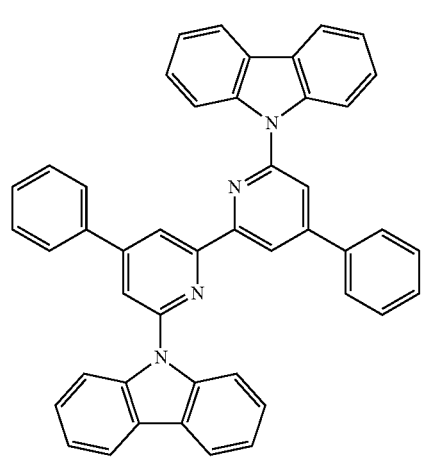
2-29
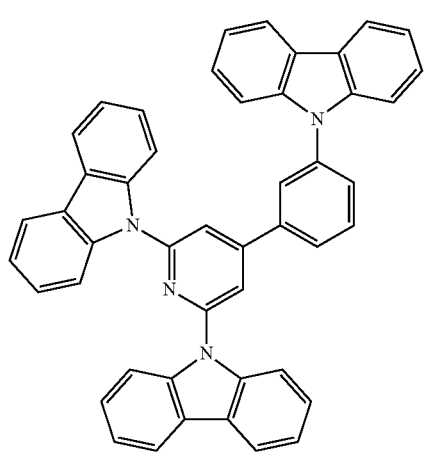

-continued
2-30
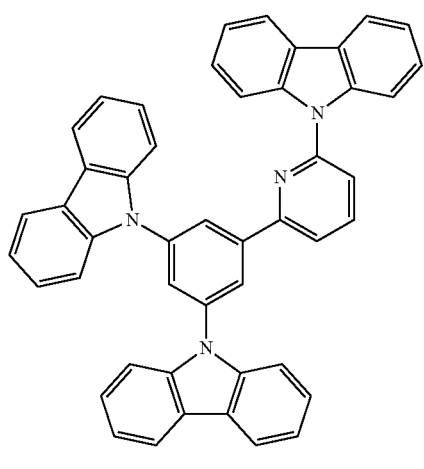
2-33
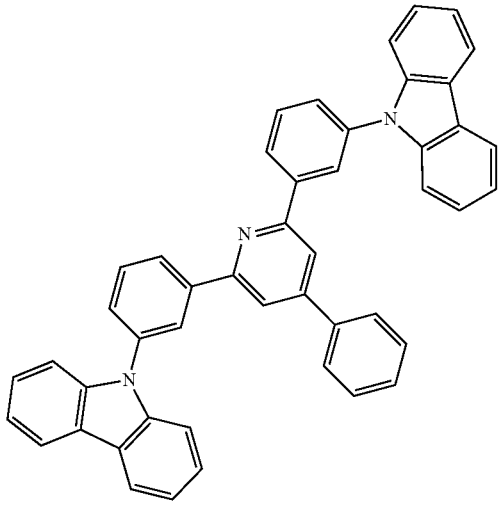
2-31
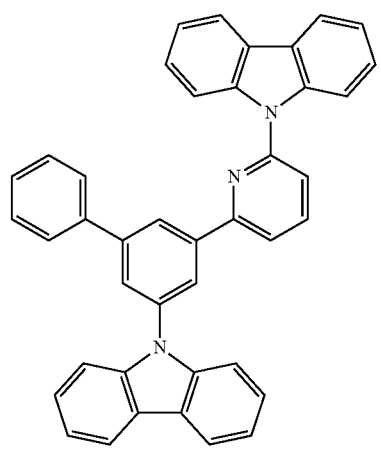
2-34
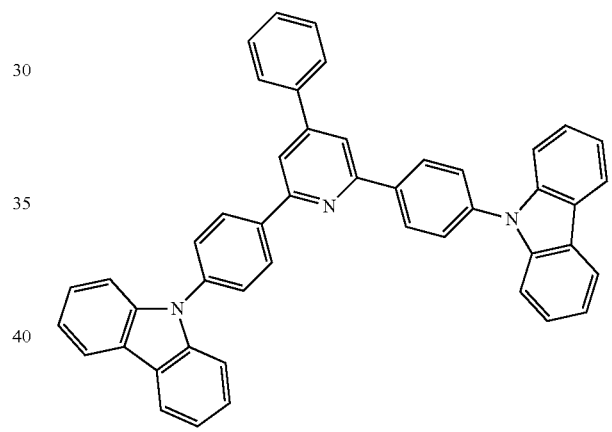
2-32
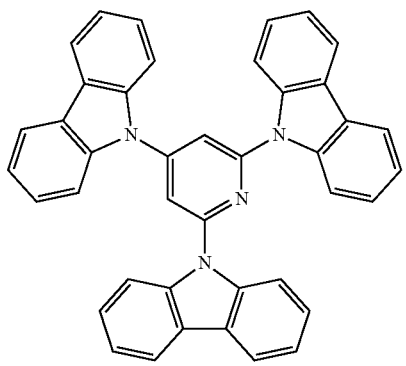
2-35
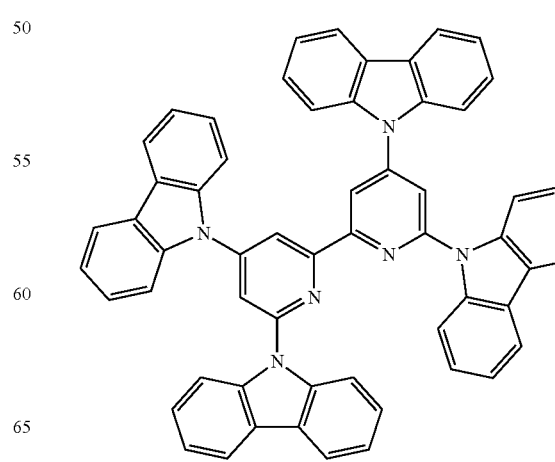

-continued
2-36
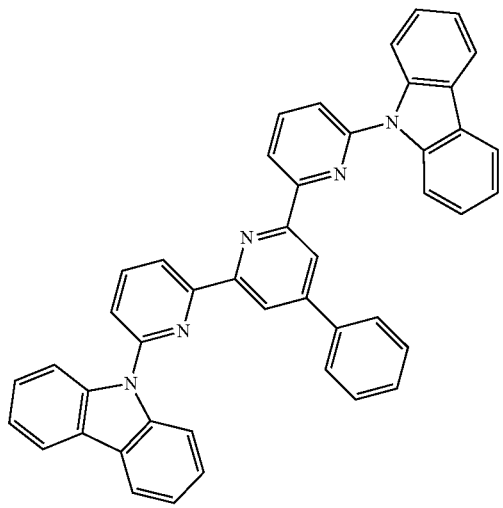
[C15]
2-37
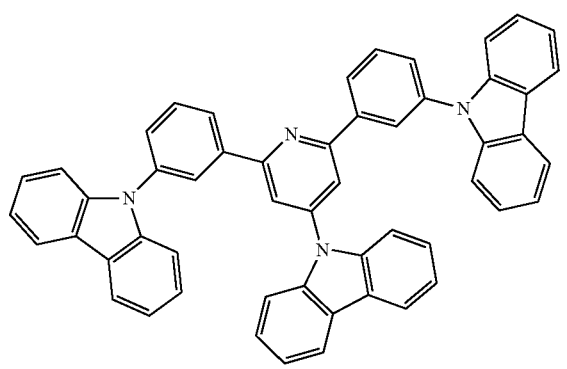
2-38
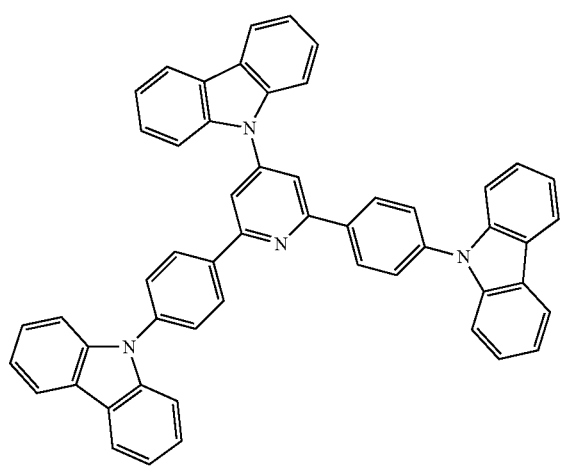
-continued
2-39
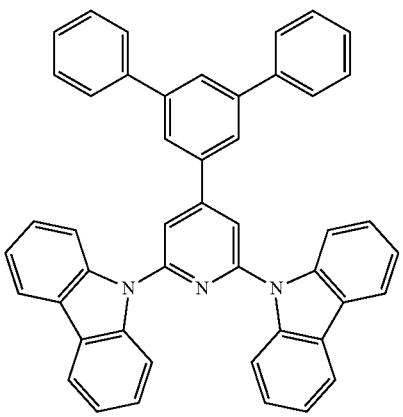
2-41
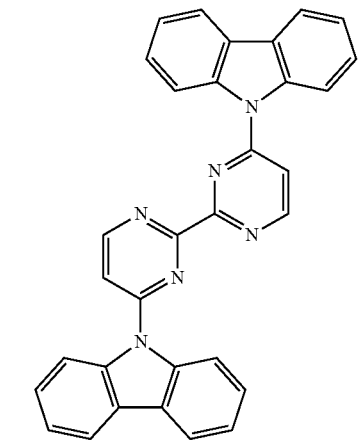
2-42
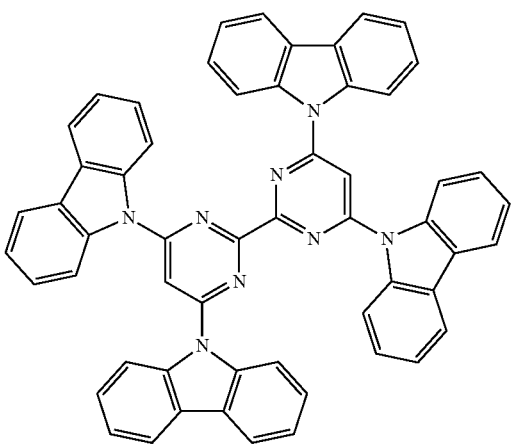

2-43
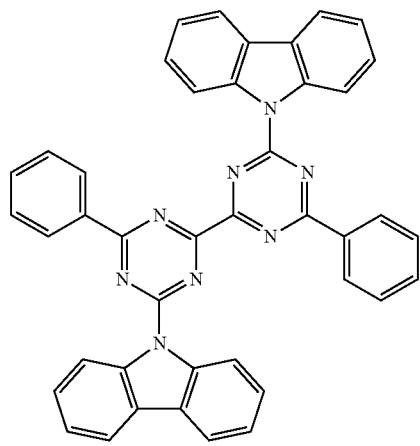
2-44
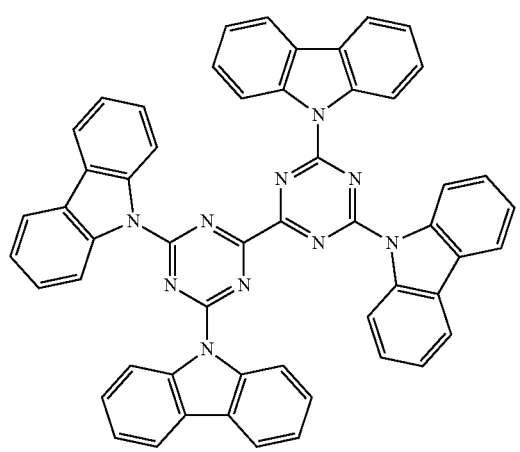
2-45
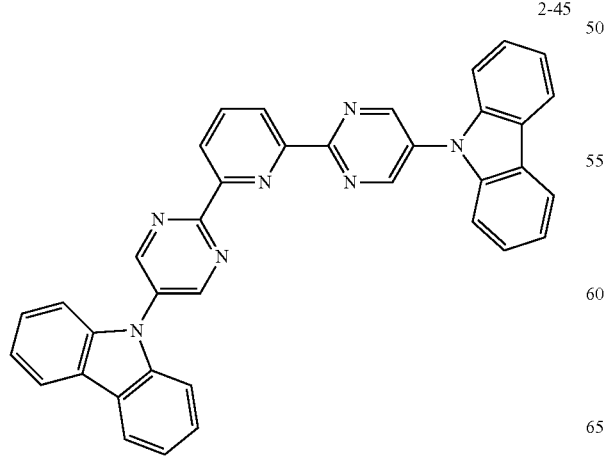
2-46
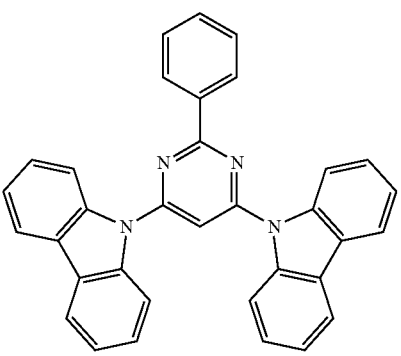
2-47
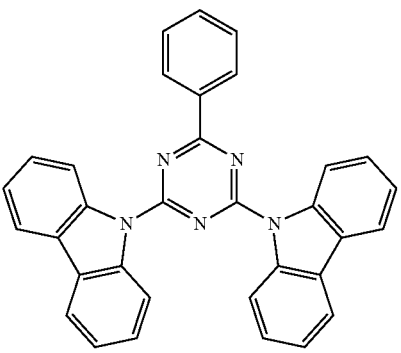
2-48
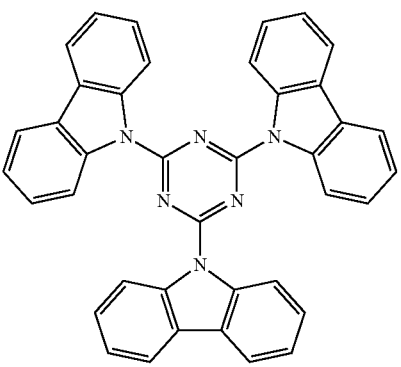
2-49
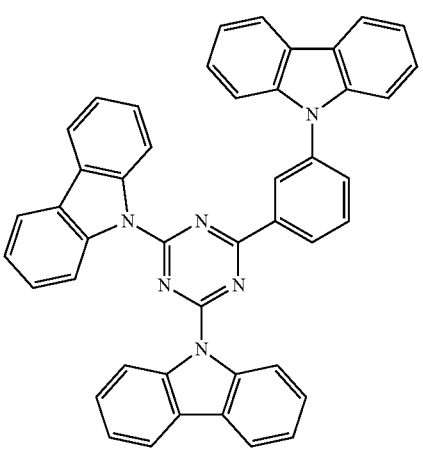

2-50
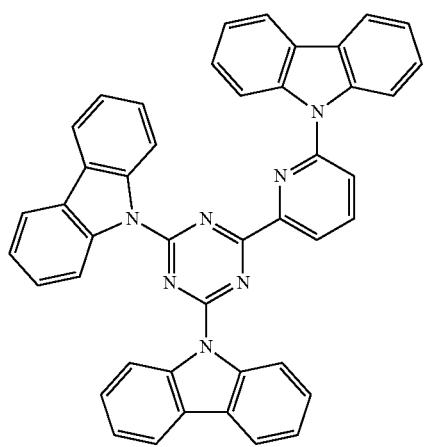
2-53
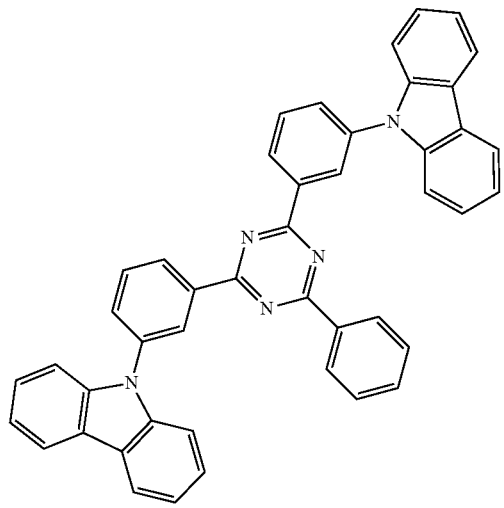
2-51
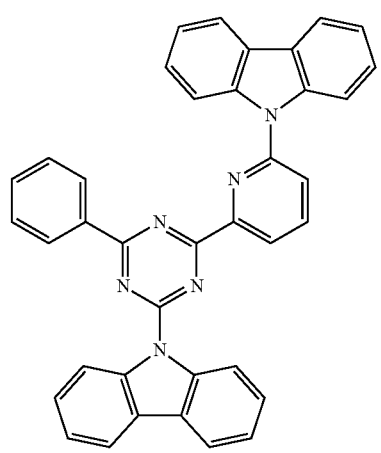
2-54
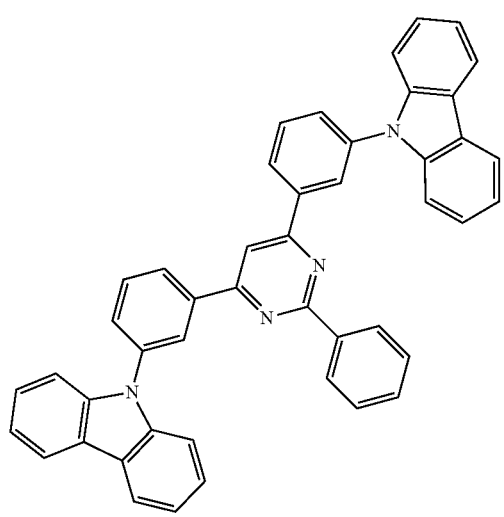
2-52
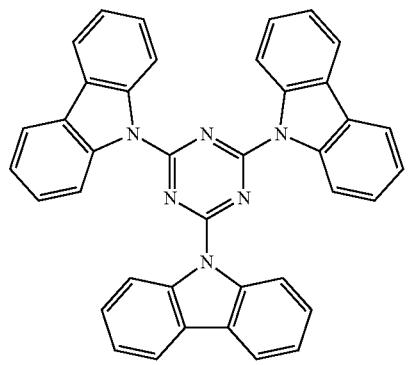
2-55
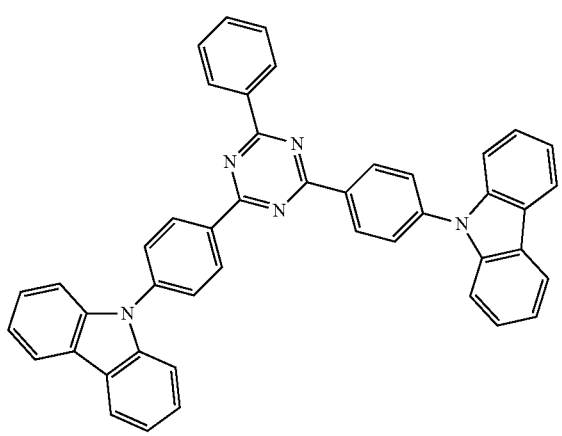

2-56

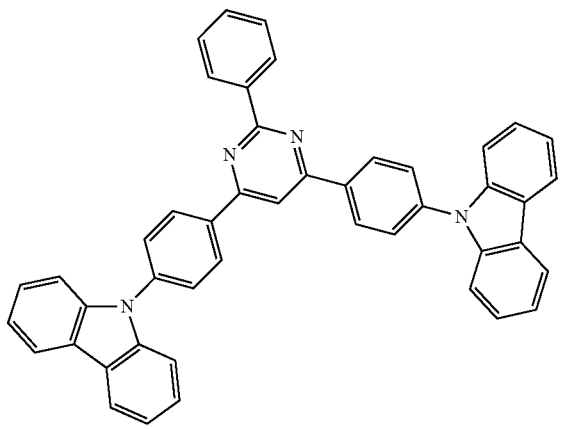

2-57

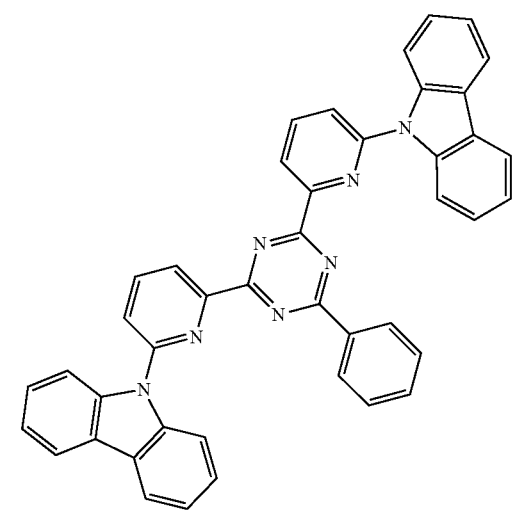

2-58

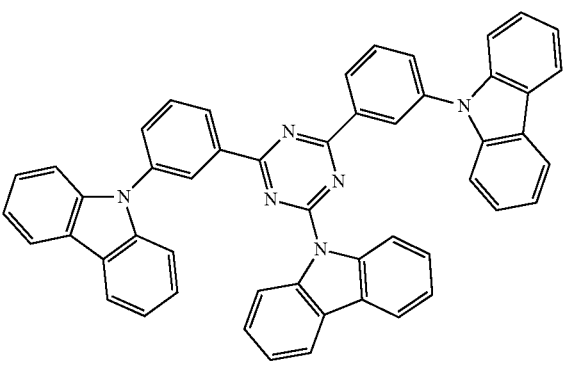

2-59

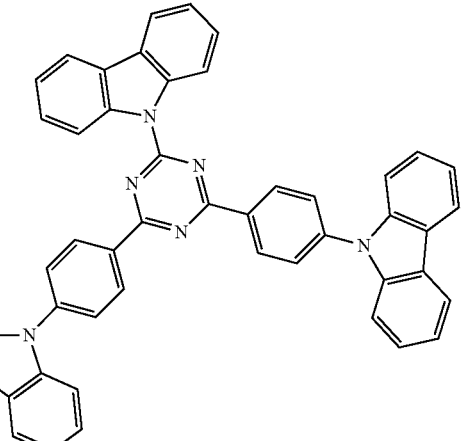

2-60

Next, General Formula (3) above will be described.

In General Formula (3), a ring C is a heterocyclic group represented by Formula (3a), and is preferably a heterocyclic group represented by Formula (4) or (5).

Y represents O or S.

$L^4$ and $L^5$ are independently a direct bond, an aromatic hydrocarbon group having 6 to 10 carbon atoms, or an aromatic heterocyclic group having 3 to 16 carbon atoms. An aromatic hydrocarbon group having 6 to 10 carbon atoms or an aromatic heterocyclic group represented by Formula (7) is preferable.

$B^5$ and $B^6$ are a direct bond or an aromatic hydrocarbon group having 6 to 22 carbon atoms. An aromatic hydrocarbon group represented by Formula (6) is preferable.

R's each independently represent hydrogen, an aromatic hydrocarbon group having 6 to 10 carbon atoms, an aromatic heterocyclic group having 3 to 16 carbon atoms, an alkyl group having 1 to 10 carbon atoms, or a cycloalkyl group having 3 to 11 carbon atoms.

In the present specification, the aromatic hydrocarbon group, the aromatic heterocyclic group, and the like may have a substituent unless otherwise specified.

m and n are numbers of substitutions and represent integers of 1 to 3, and are preferably integers of 1 and 2.

p and q are numbers of repetitions and are each independently integers of 1 to 4 and preferably integers of 1 and 2.

Specific examples of compounds represented by General Formula (3) will be shown below, but the present invention is not limited thereto.

[C16]
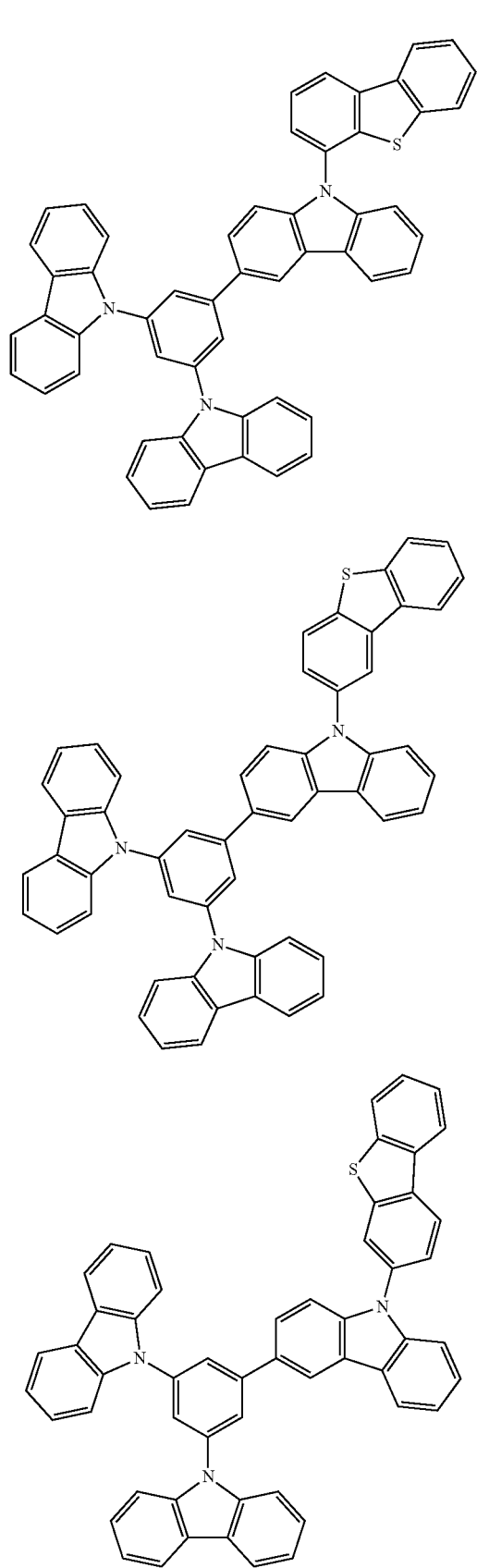
3-1
3-2
3-3
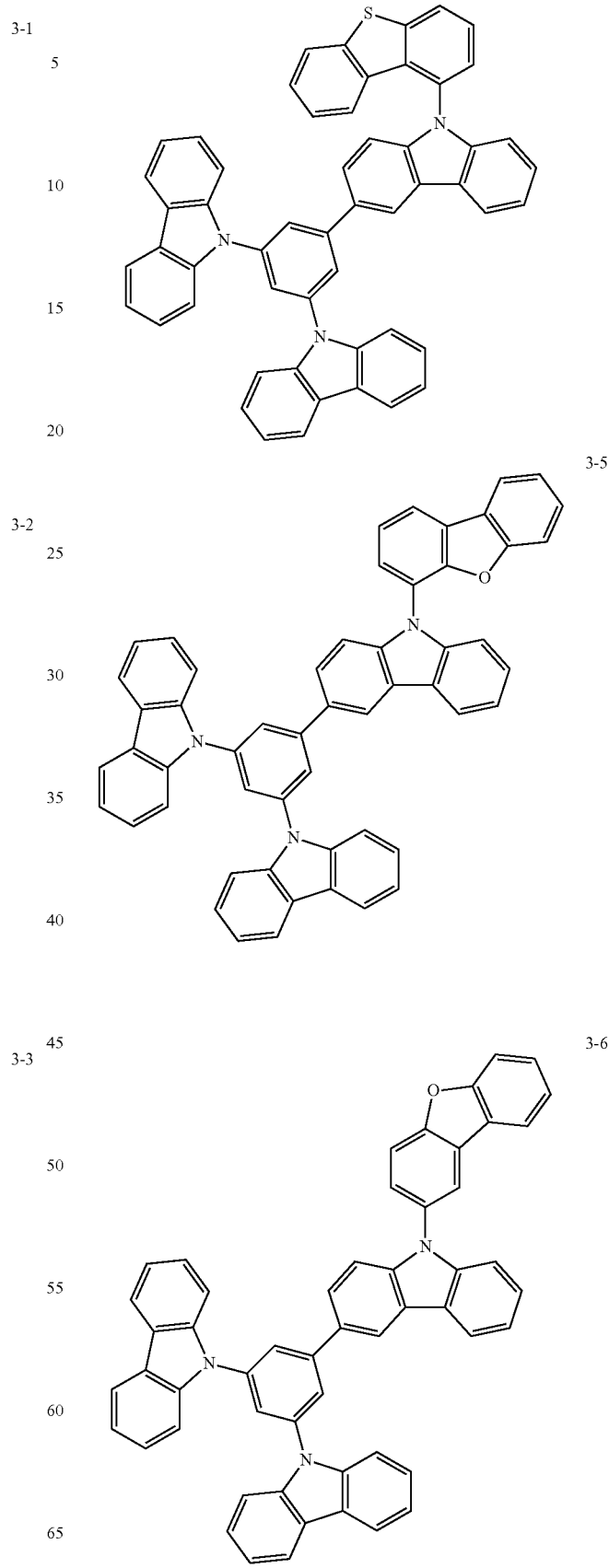
3-4
3-5
3-6

3-7
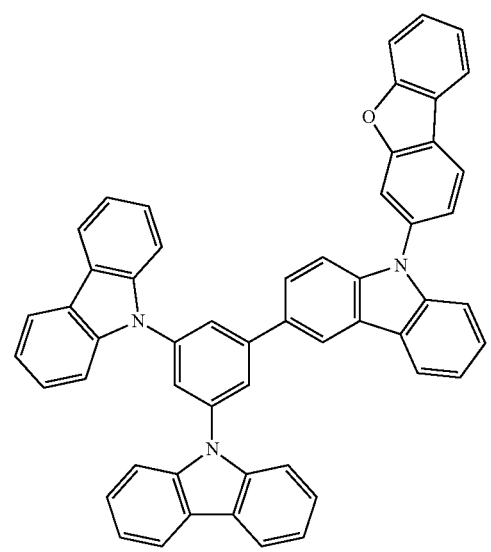
3-8
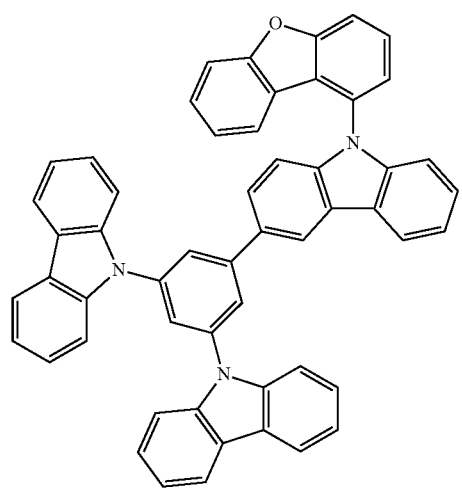
3-9
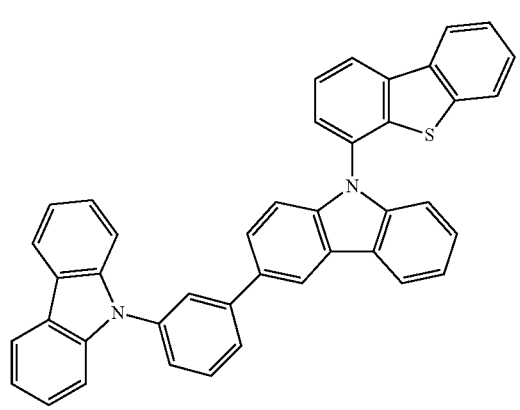
3-10
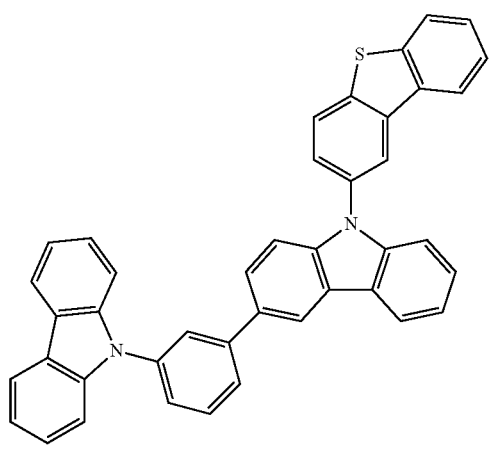
3-11
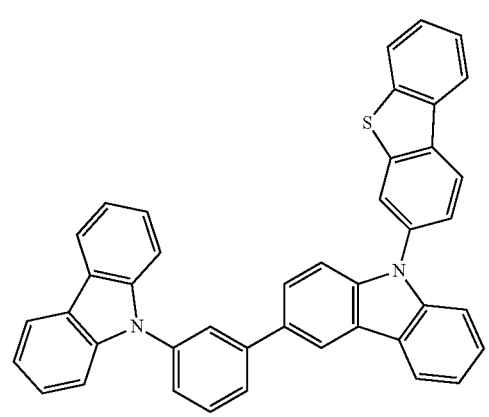
3-12
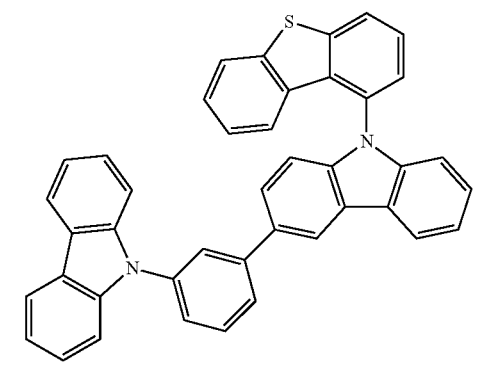
3-13
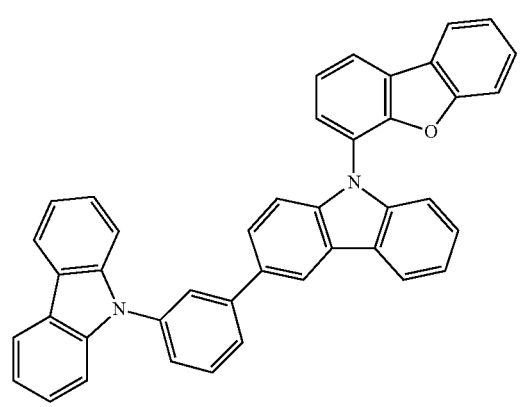

3-14
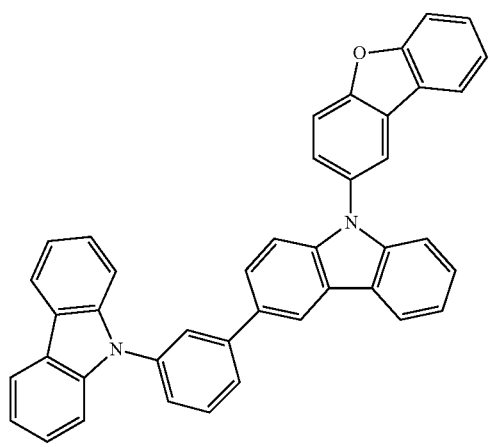
3-15
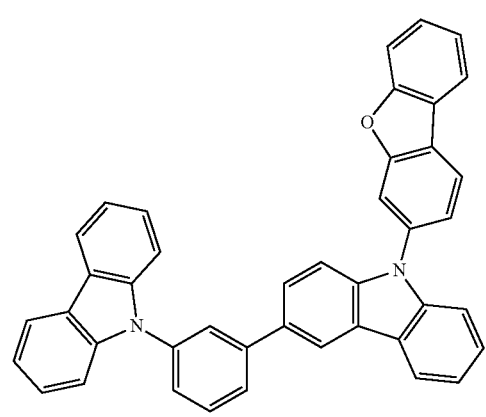
3-16
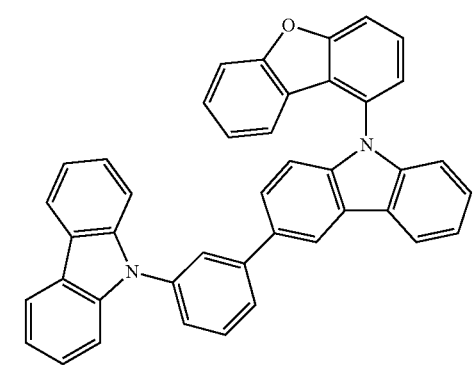
3-17
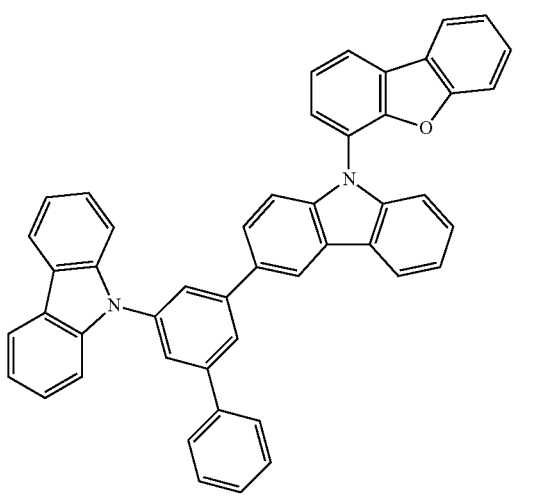
3-18
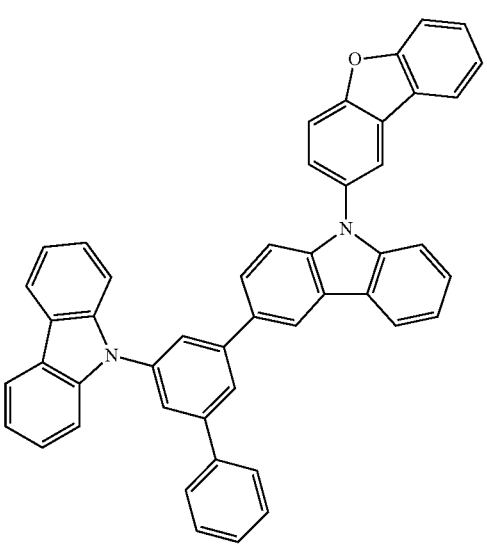
3-19
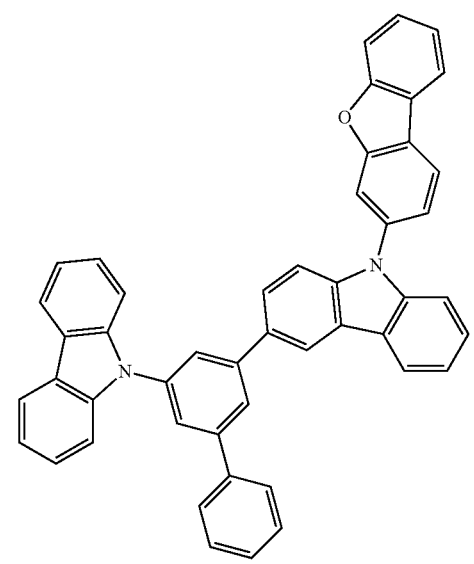

3-20
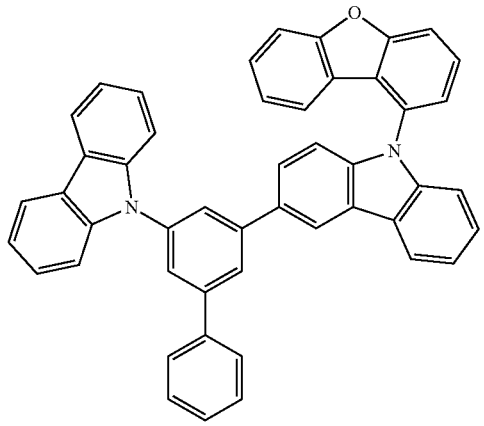
[C17]
3-21
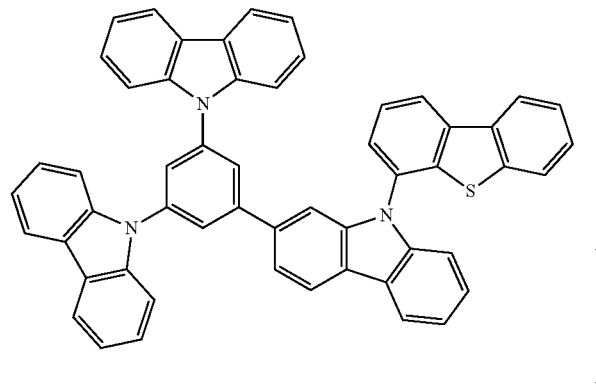
3-22
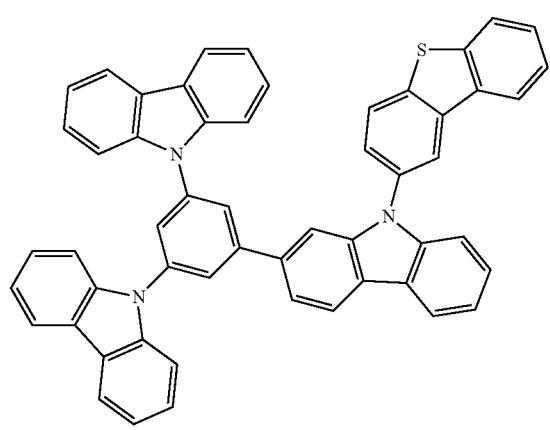
3-23
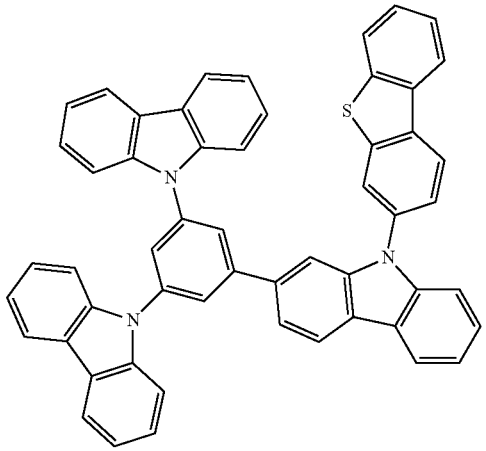
3-24
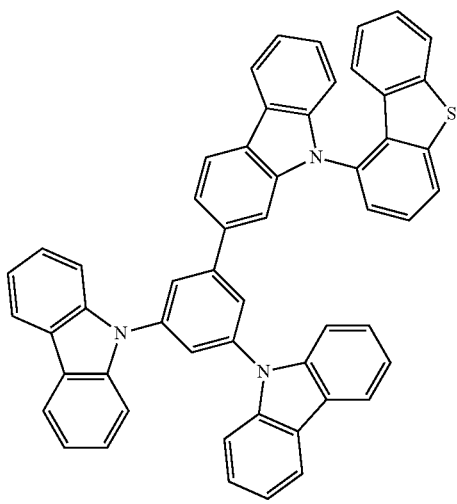
3-25
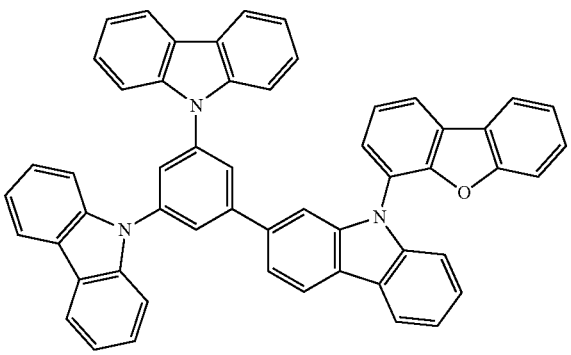

3-26
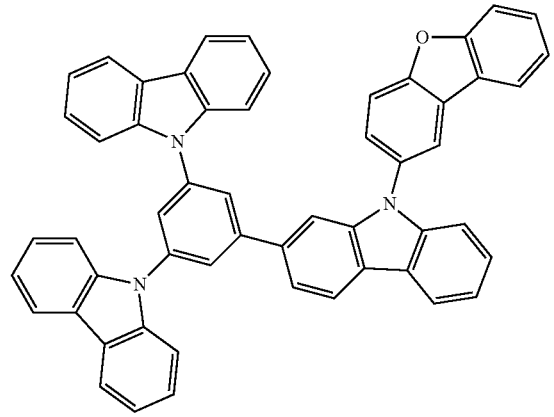
3-27
3-28
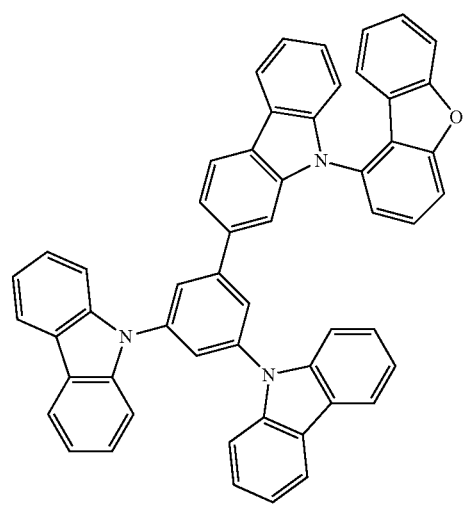
3-29
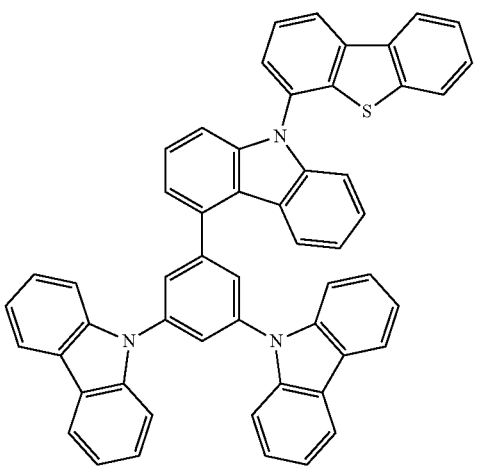
3-30
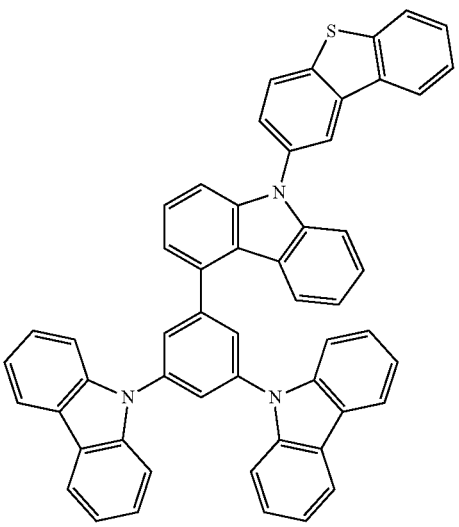
3-31

3-32
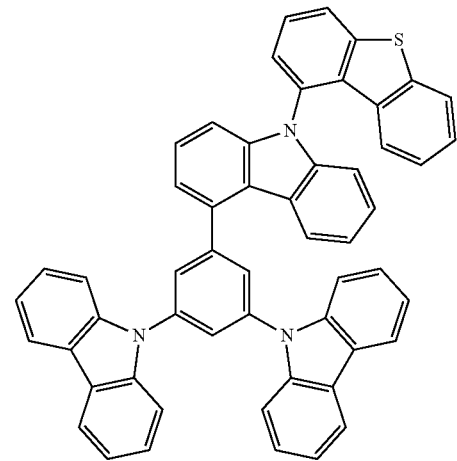
3-29b
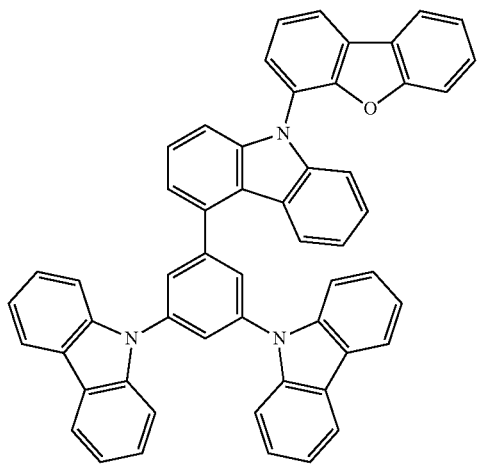
3-30b
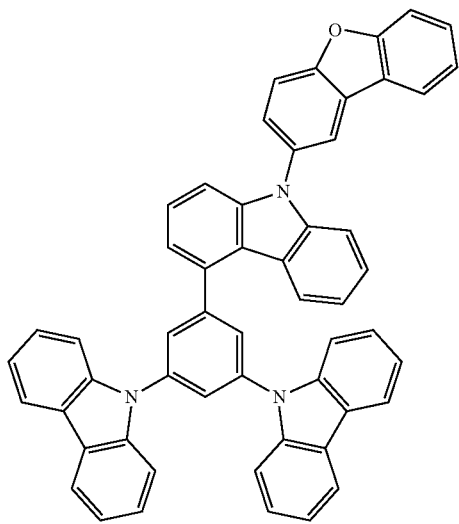
3-31b
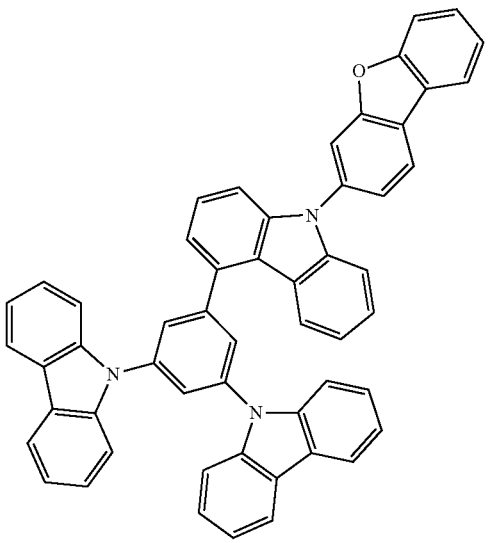
3-32b
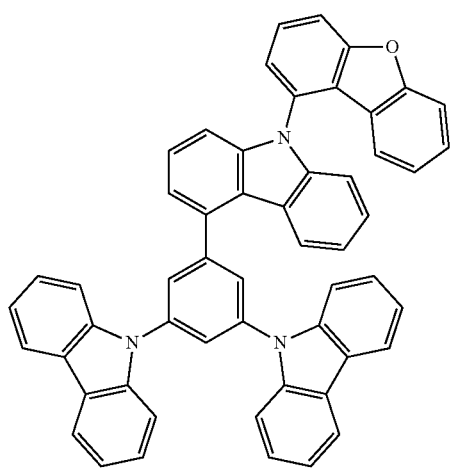
3-33
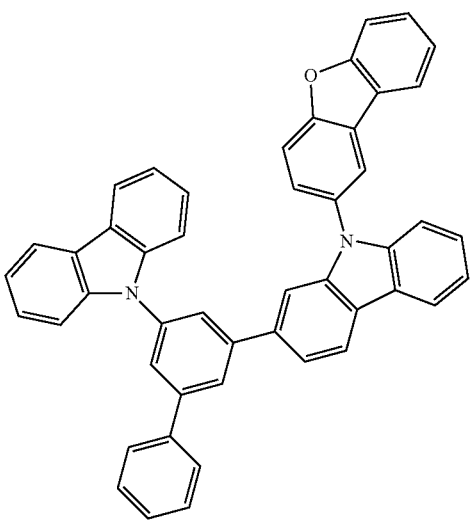

3-34
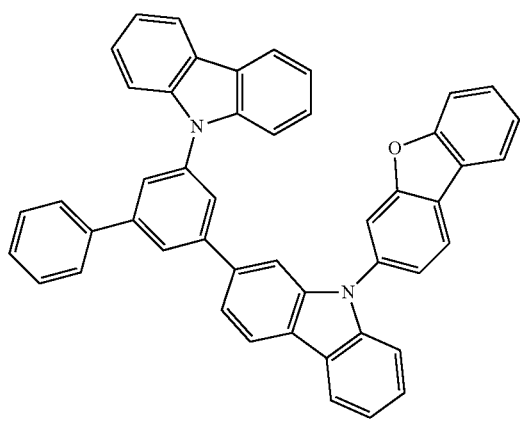
3-35
3-36
3-37
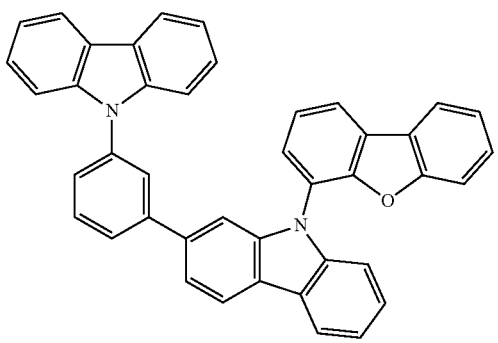
3-38
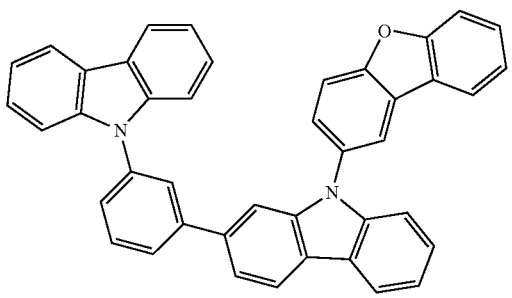
3-39
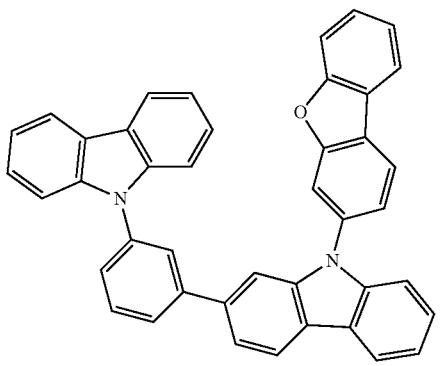
3-40
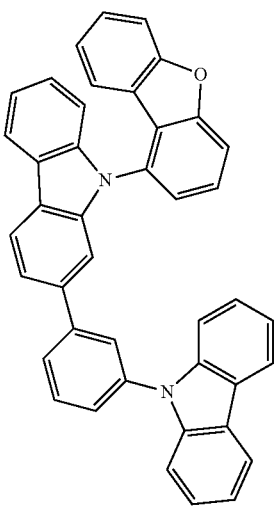

3-41
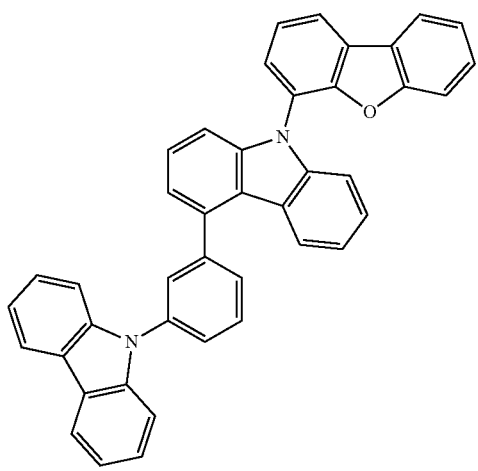
3-42
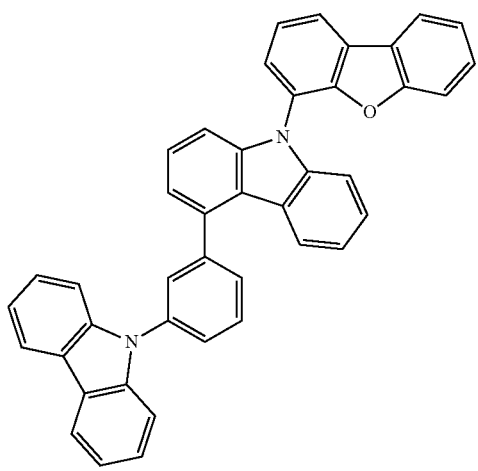
3-43
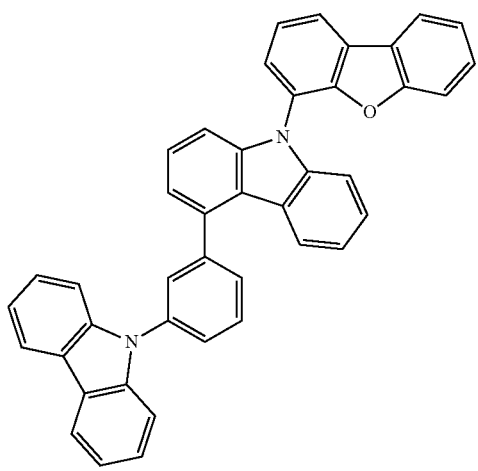
3-44
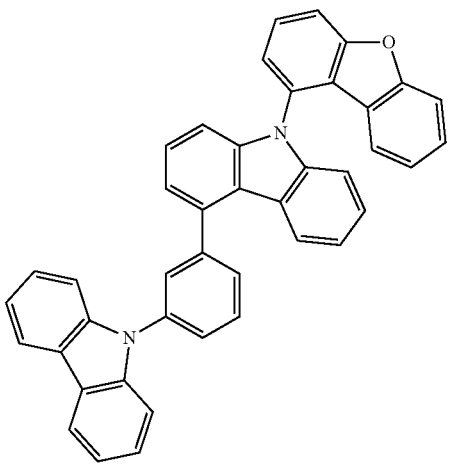
3-45
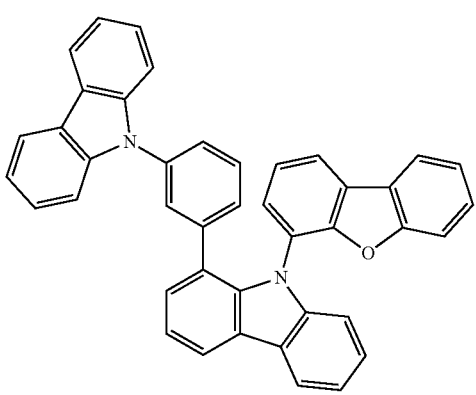
3-46
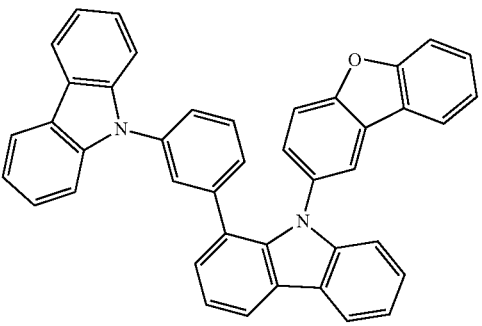
3-47
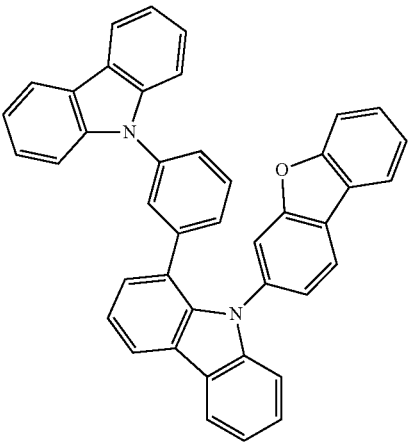

3-48
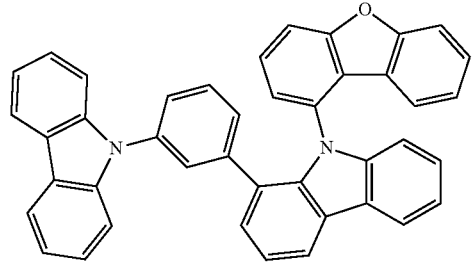
3-49
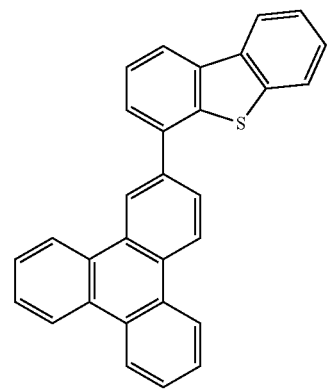
3-50
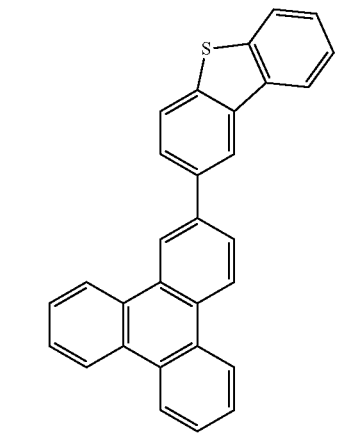
3-51
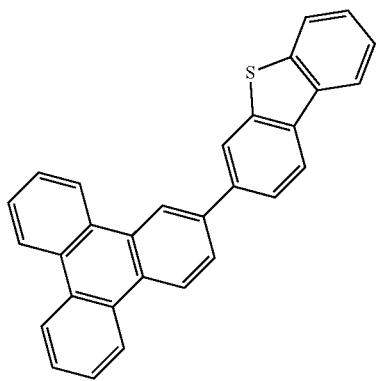
3-52
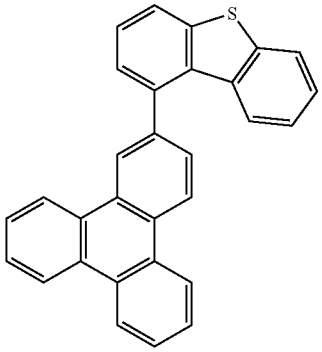
3-53
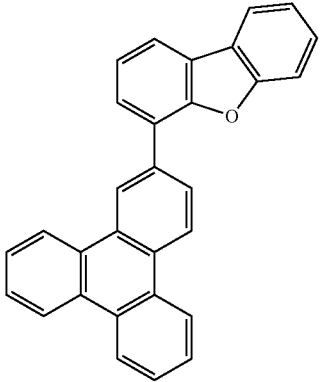
3-54
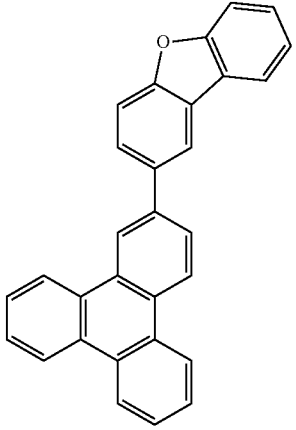
3-55
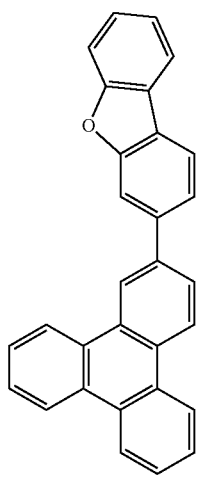

3-56
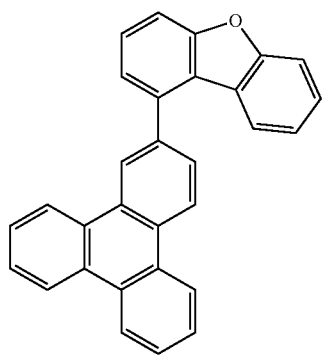
[C19]
3-57
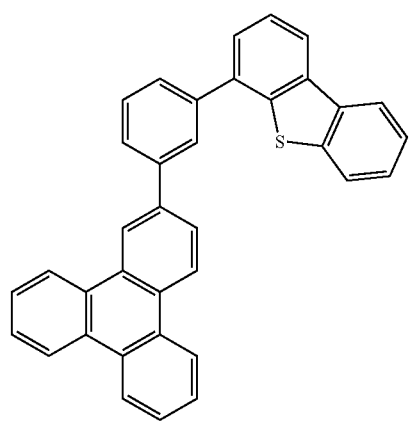
3-58
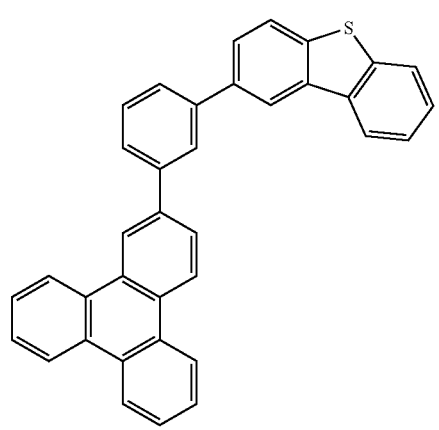
3-59
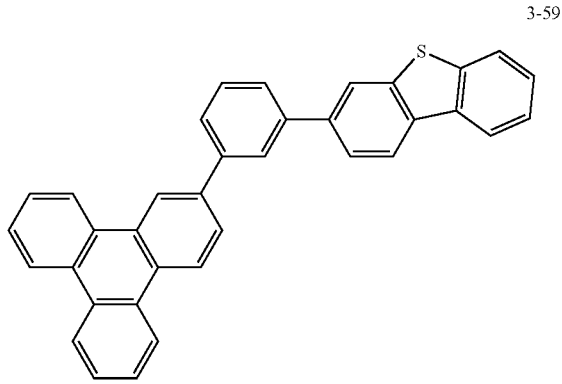
3-60
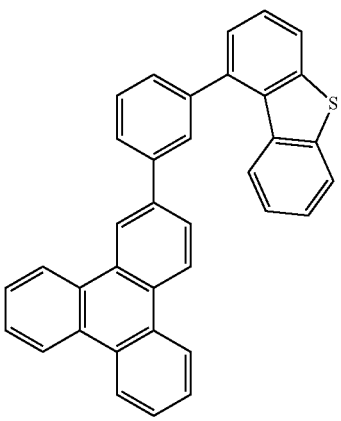
3-61
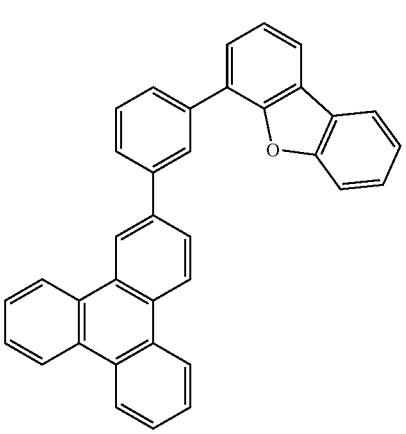
3-62
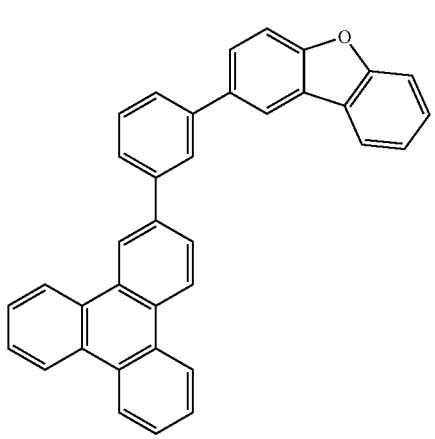
3-63
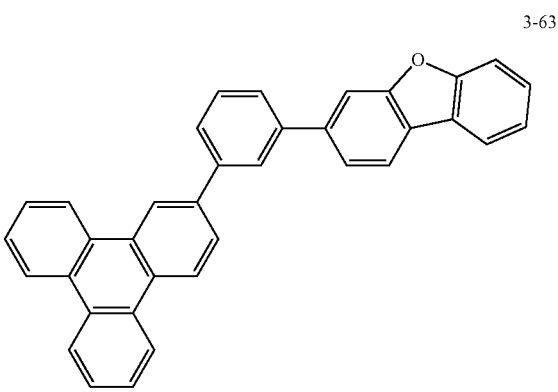

3-64
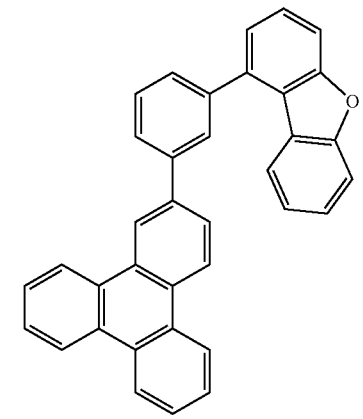
3-65
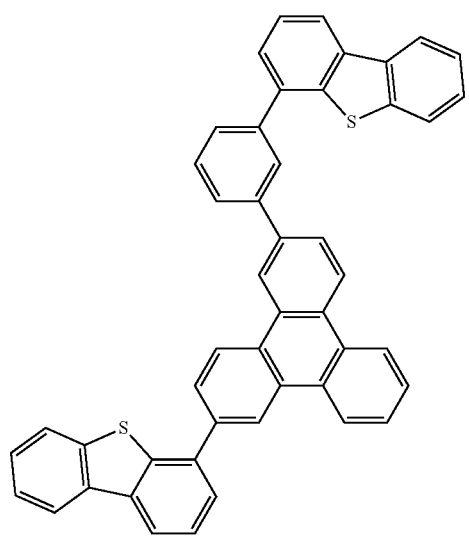
3-66
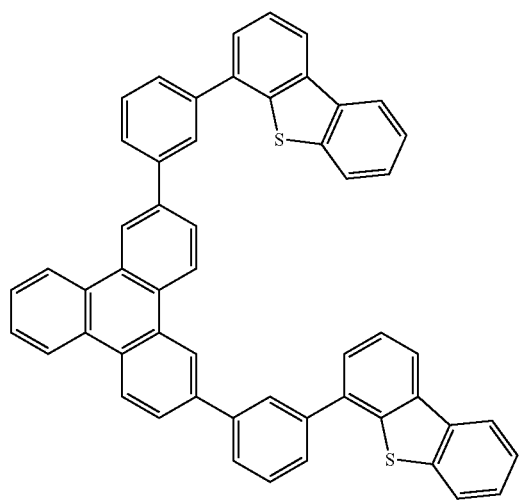
3-67
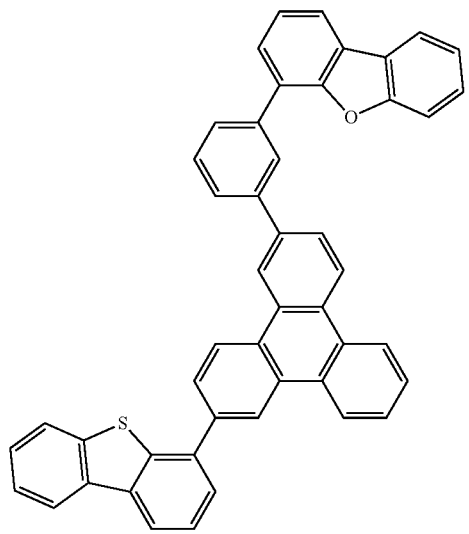
3-68
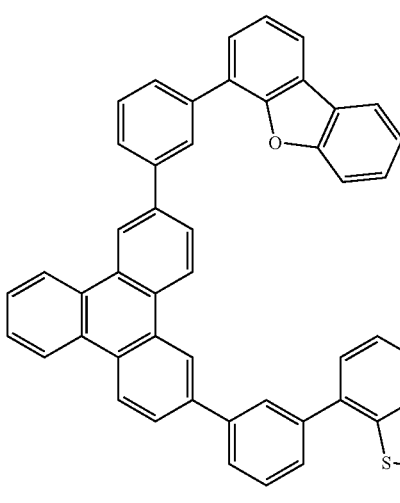
3-69
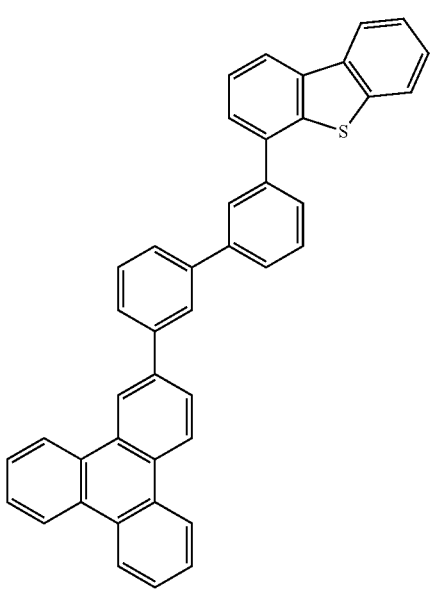

-continued
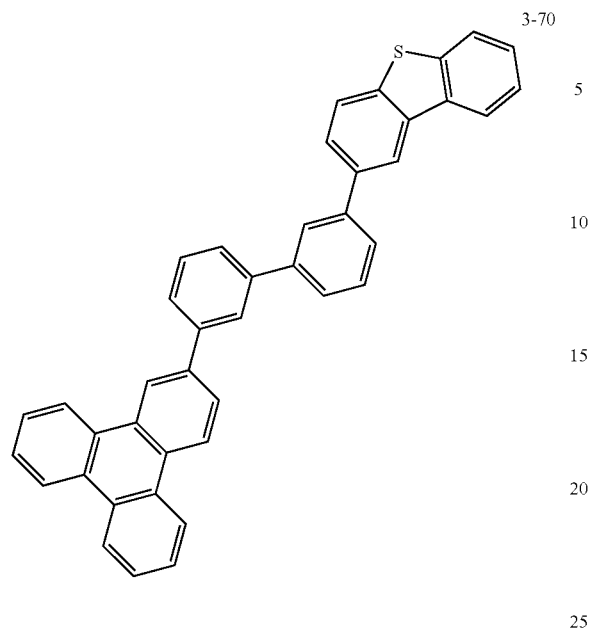
3-70
3-71
3-72
-continued
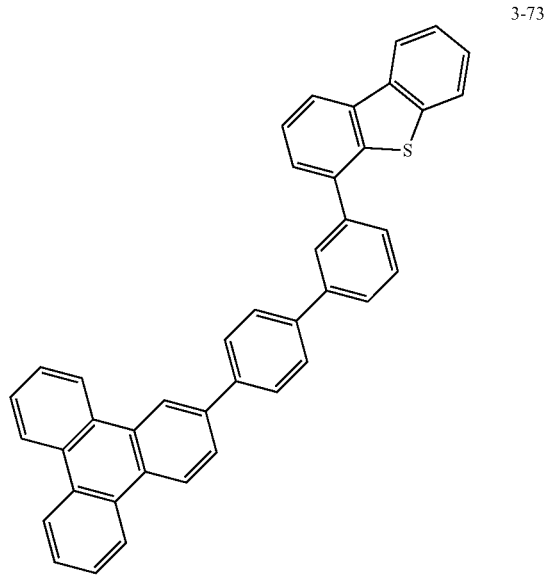
3-73
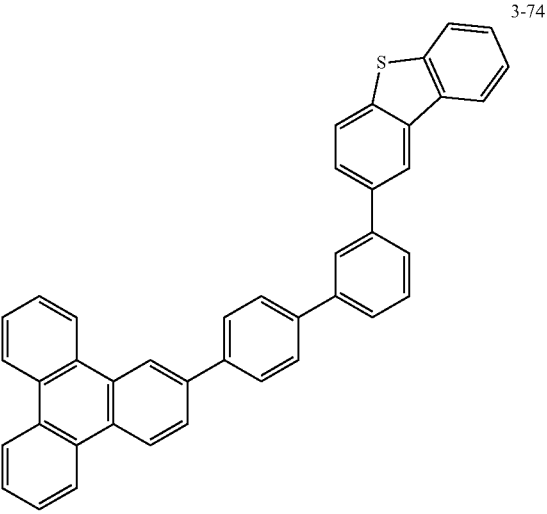
3-74
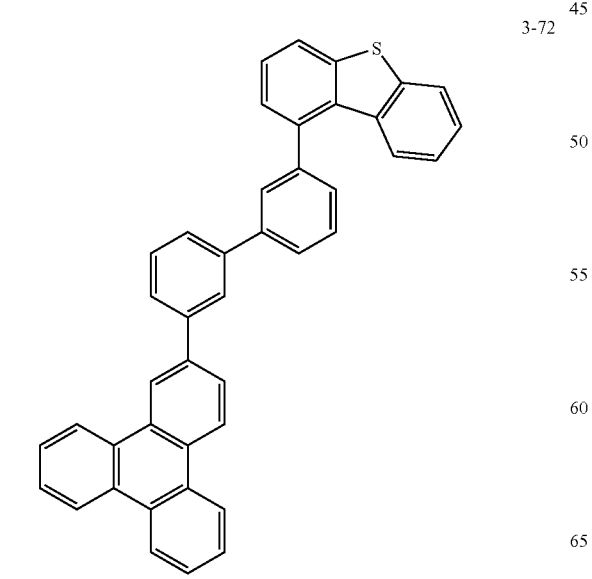
3-75

3-76

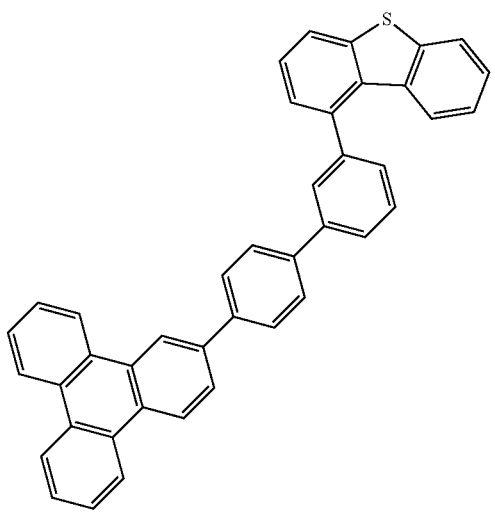

An excellent organic EL device can be provided using a first host selected from the compounds represented by General Formula (1) and a second host selected from the compounds represented by General Formulae (2) and (3) as host materials for a light emitting layer.

The first host and the second host can be used by being vapor-deposited from different vapor deposition sources. However, it is preferable that a premixture be prepared by premixing the first host and the second host before vapor deposition and these be vapor-deposited simultaneously from one vapor deposition source to form a light emitting layer. In this case, a luminescent dopant material required for forming a light emitting layer or other hosts used as necessary may be mixed with this premixture. However, in a case where there is a large difference between temperatures at which desired vapor pressures are obtained, the vapor deposition is preferably performed from different vapor deposition sources.

In addition, regarding the mixing ratio (weight ratio) between a first host and a second host, the proportion of the first host in the total amount of the first host and the second host may be 20% to 60%, and is preferably higher than 20% and lower than 55% and more preferably 40% to 50%.

Next, the structure of the organic EL device of the present invention will be described with reference to the drawings, but is not limited thereto.

FIG. 1 is a cross-sectional view illustrating a structural example of a general organic EL device used in the present invention. 1 represents a substrate, 2 represents an anode, 3 represents a hole injection layer, 4 represents a hole transport layer, 5 represents a light emitting layer, 6 represents an electron transport layer, and 7 represents a cathode. The organic EL device of the present invention may have an exciton-blocking layer adjacent to the light emitting layer or may have an electron-blocking layer between the light emitting layer and the hole injection layer. The exciton-blocking layer can be inserted into the light emitting layer on any position on the cathode side or an anode side and can be inserted into both sides at the same time. The organic EL device of the present invention has an anode, a light emitting layer, and a cathode as essential layers. However, it is preferable that the organic EL device of the present invention have a hole injection/transport layer and an electron injection/transport layer in addition to the essential layers and further have a hole-blocking layer between the light emitting layer and the electron injection/transport layer. The hole injection/transport layer means either or both of a hole injection layer and a hole transport layer, and the electron injection/transport layer means either or both of an electron injection layer and an electron transport layer.

A structure opposite to that of FIG. 1 can also be used, that is, a cathode 7, an electron transport layer 6, a light emitting layer 5, a hole transport layer 4, and an anode 2 are laminated on a substrate 1 in this order. Even in this case, layers can be added or omitted as necessary.

—Substrate—

The organic EL device of the present invention is preferably supported by a substrate. Such a substrate is not particularly limited as long as it is conventionally used in organic EL devices, and a substrate made of glass, transparent plastic, quartz, or the like can be used.

—Anode—

As materials for an anode in an organic EL device, metals, alloys, electrically conductive compounds, or materials composed of a mixture thereof which have a large work function (4 eV or more) are preferably used. Specific examples of such electrode materials include metals such as Au and conductive transparent materials such as CuI, indium tin oxide (ITO), $SnO_2$, and ZnO. In addition, amorphous materials such as IDIXO ($In_2O_3$—ZnO) capable of producing a transparent conductive film may be used. Regarding an anode, a thin film may be formed through a method such as vapor deposition or sputtering of these electrode materials to form a pattern having a desired shape through a photolithographic method. Alternatively, in a case where pattern accuracy is not required much (about 100 μm or more), a pattern may be formed using a mask having a desired shape during vapor-depositing or sputtering of the above-described electrode materials. Alternatively, in a case where an applicable substance such as an organic conductive compound is used, wet film formation methods such as a printing method or a coating method can also be used. In a case where light emission is taken out from this anode, it is desirable to increase the transmittance to more than 10% and it is preferable to set the sheet resistance of an anode to several hundred Ω/square or less. The film thickness also depends on materials, but is selected from a range of usually 10 to 1,000 nm and preferably 10 to 200 nm.

—Cathode—

On the other hand, as cathode materials (electron injecting metals), alloys, electrically conductive compounds, or materials composed of a mixture thereof which have a small work function (4 eV or less) are used. Specific examples of such electrode materials include sodium, sodium-potassium alloys, magnesium, lithium, magnesium-copper mixtures, magnesium-silver mixtures, magnesium-aluminum mixtures, magnesium-indium mixtures, aluminum-aluminum oxide ($Al_2O_3$) mixtures, indium, lithium-aluminum mixtures, and rare earth metals. Among these, a mixture of an electron injecting metal and a secondary metal which is a stable metal having a larger work function than the electron injecting metal, for example, a magnesium-silver mixture, a magnesium-aluminum mixture, a magnesium-indium mixture, an aluminum-aluminum oxide mixture, a lithium-aluminum mixture, or aluminum is suitable from the viewpoints of electron injecting properties and durability against oxidation. A cathode can be produced by forming a thin film through a method such as vapor deposition or sputtering of these cathode materials. In addition, the sheet resistance of a cathode is preferably several hundred Ω/square or less, and the film thickness is selected from a range of usually 10 nm to 5 µm and preferably 50 to 200 nm. It is preferable that the luminance be improved by making either an anode or a cathode of an organic EL device be transparent or translucent to allow emitted light to be transmitted therethrough.

In addition, after forming the above-described metals on a cathode at a film thickness of 1 to 20 nm, a conductive transparent material exemplified in the description of the anode can be formed thereon to produce a transparent or translucent cathode. By using this process, a device in which both an anode and a cathode are transparent can be produced.

—Light Emitting Layer—

A light emitting layer is a layer emitting light after production of excitons due to recombination of holes and electrons respectively injected from an anode and a cathode and contains an organic luminescent dopant material and a host material.

The first host represented by General Formula (1) and the second host represented by General Formula (2) or (3) are used as a host material in the light emitting layer. Furthermore, one kind or plural kinds of well-known host materials may be used in combination, and it is preferable that the amount used be 50 wt % or less and preferably 25 wt % or less based on the total amount of the host materials. In addition, one kind or two or more kinds of the first host represented by General Formula (1) and the second host represented by General Formula (2) or (3) may be used.

The first host and the second host can be vapor-deposited from different vapor deposition sources. Alternatively, a premixture can be prepared by premixing the first host and the second host before vapor deposition and vapor-deposited simultaneously from one vapor deposition source.

In the case where the first host and the second host are used by being premixed, the difference in 50% weight reduction temperature ($T_{50}$) is desirably small in order to produce an organic EL device having favorable characteristics with good reproducibility. The 50% weight reduction temperature is a temperature when the weight is reduced by 50% when the temperature is raised from room temperature to 550° C. at a rate of 10° C. per minute in TG-DTA measurement under nitrogen stream decompression (50 Pa). It is thought that vaporization due to evaporation or sublimation occurs most actively in the vicinity of this temperature range.

The difference in 50% weight reduction temperature between the first host and the second host is preferably within 20° C. and more preferably within 15° C. As the premixing method, a well-known method such as pulverizing and mixing can be employed, and it is desirable that the mixing be performed as uniformly as possible.

In a case where a phosphorescent dopant is used as a luminescent dopant material, a phosphorescent dopant containing an organic metal complex containing at least one metal selected from the group consisting of ruthenium, rhodium, palladium, silver, rhenium, osmium, iridium, platinum, and gold may be used. Specifically, iridium complexes disclosed in J. Am. Chem. Soc. 2001, 123, 4304 or Japanese Translation of PCT Application No. 2013-53051 are suitably used, but the present invention is not limited thereto.

Only one kind of a phosphorescent dopant material may be contained in a light emitting layer, or two or more kinds of phosphorescent dopant materials may be contained therein. The content of a phosphorescent dopant material with respect to a host material is preferably 0.1 to 30 wt % and more preferably 1 to 20 wt %.

The phosphorescent dopant material is not particularly limited, but specific examples thereof include the following.

[C20]

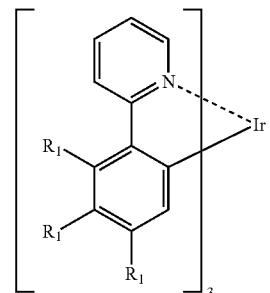

$R_1$: H, $CH_3$, $CF_3$, F

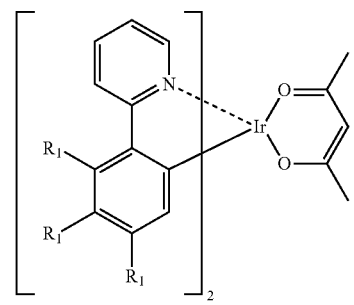

$R_2$: H, F

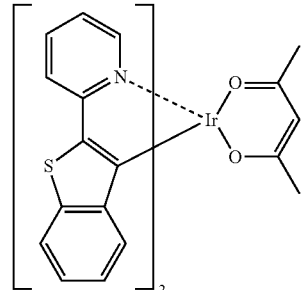

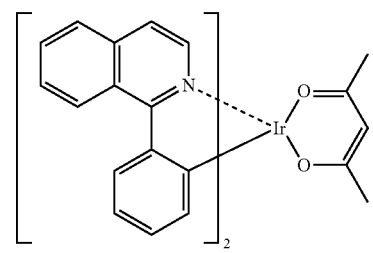

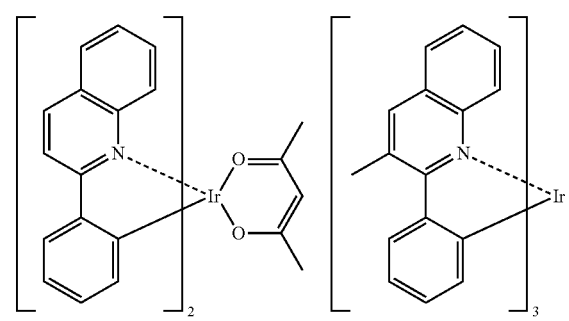

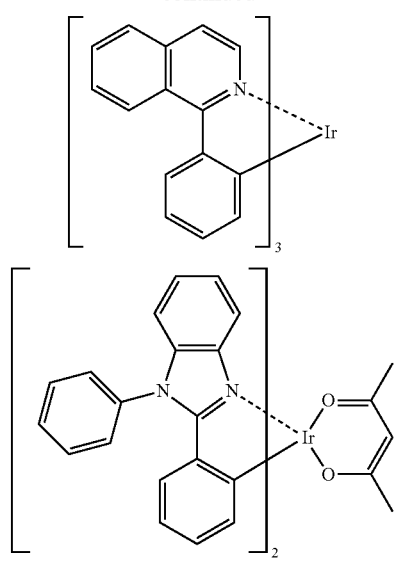
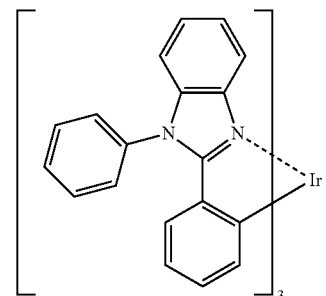
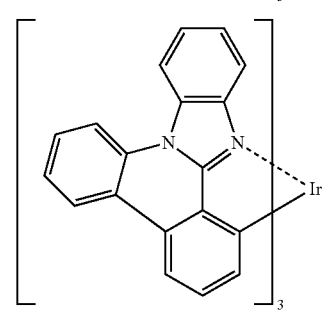
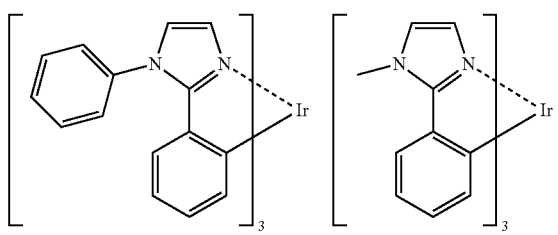
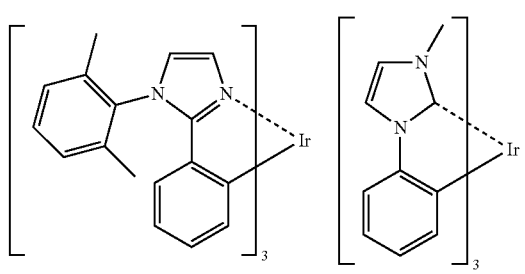
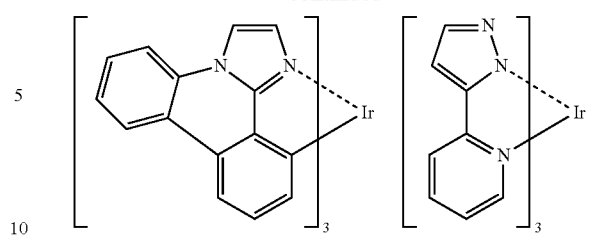
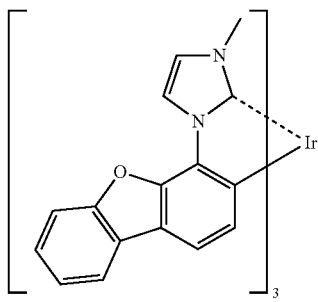
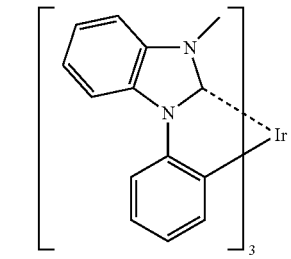
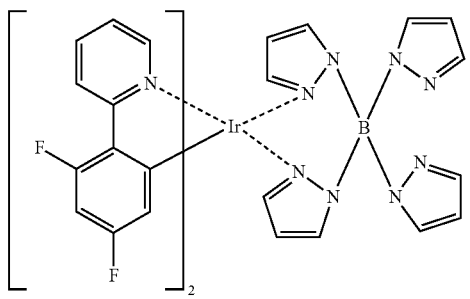
[C21]
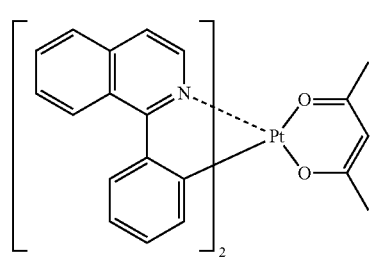
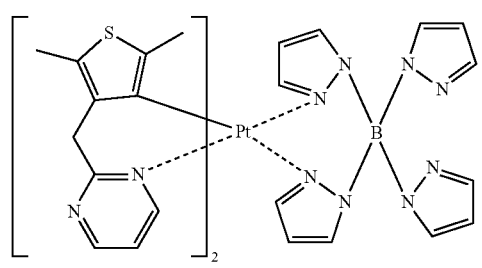

-continued

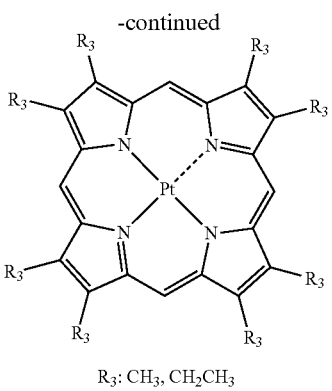

R₃: CH₃, CH₂CH₃

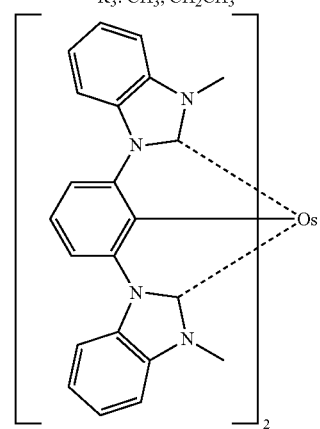

In a case where a fluorescent dopant is used as a luminescent dopant material, the fluorescent dopant is not particularly limited, but examples thereof include benzoxazole derivatives, benzothiazole derivatives, benzoimidazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyrrolidine derivatives, cyclopentadiene derivatives, bisstyrylanthracene derivatives, quinacridone derivatives, pyrrolopyridine derivatives, thiadiazolopyridine derivatives, styrylamine derivatives, diketopyrrolopyrrole derivatives, aromatic dimethylidyne compounds, various metal complexes typified by metal complexes of 8-quinolinol derivatives, metal complexes of pyrromethene derivatives, rare earth complexes, and transition metal complexes, polymer compounds such as polythiophene, polyphenylene, and polyphenylene vinylene, and organic silane derivatives. Preferred examples thereof include condensed aromatic derivatives, styryl derivatives, diketopyrrolopyrrole derivatives, oxazine derivatives, pyrromethene metal complexes, transition metal complexes, and lanthanoid complexes, and more preferred examples thereof include naphthalene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo [a] naphthalene, hexacene, naphth[2,1-f] isoquinoline, α-naphthaphenanthridin, phenanthrooxazole, quinolino[6,5-f]quinoline, and benzothiophanthrene. These may have an alkyl group, an aryl group, an aromatic heterocyclic group, or a diarylamino group as a substituent.

Only one kind of a fluorescent dopant material may be contained in a light emitting layer, or two or more kinds of phosphorescent dopant materials may be contained therein.

The content of a fluorescent dopant material with respect to a host material is preferably 0.1 to 20% and more preferably 1 to 10%.

In a case where a thermally activated delayed fluorescent dopant is used as a luminescent dopant material, although the thermally activated delayed fluorescent dopant is not particularly limited, examples thereof include metal complexes such as a tin complex or a copper complex, indolocarbazole derivatives disclosed in WO2011/070963, cyanobenzene derivatives and carbazole derivatives disclosed in Nature 2012, 492, 234, and phenazine derivatives, oxadiazole derivatives, triazole derivatives, sulfone derivatives, phenoxazine derivatives, and acridine derivatives disclosed in Nature Photonics 2014, 8, 326.

The thermally activated delayed fluorescent dopant material is not particularly limited, but specific examples thereof include the following.

[C22]

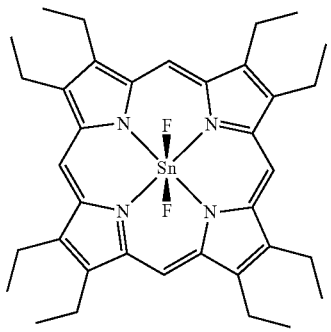

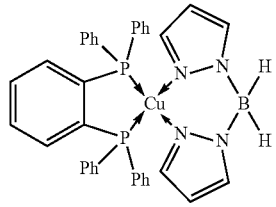

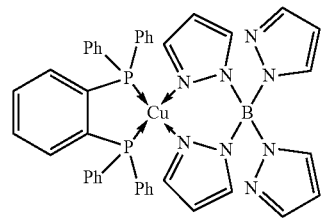

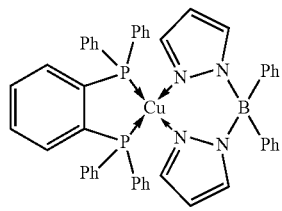

99
-continued
100
-continued
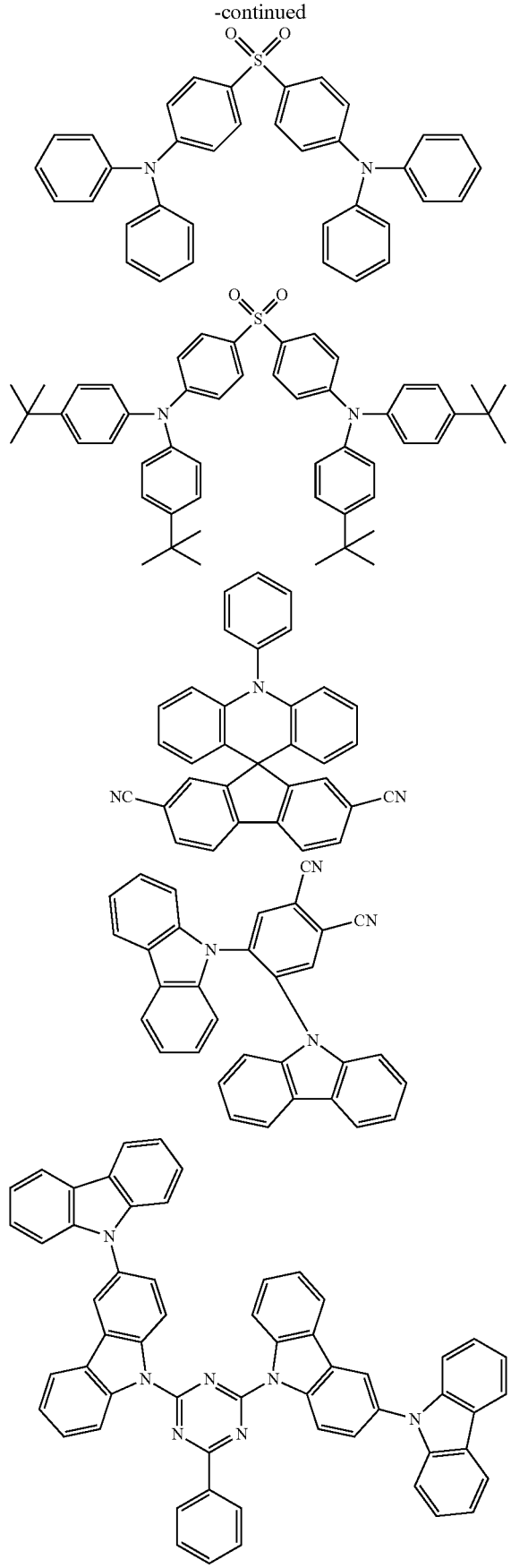
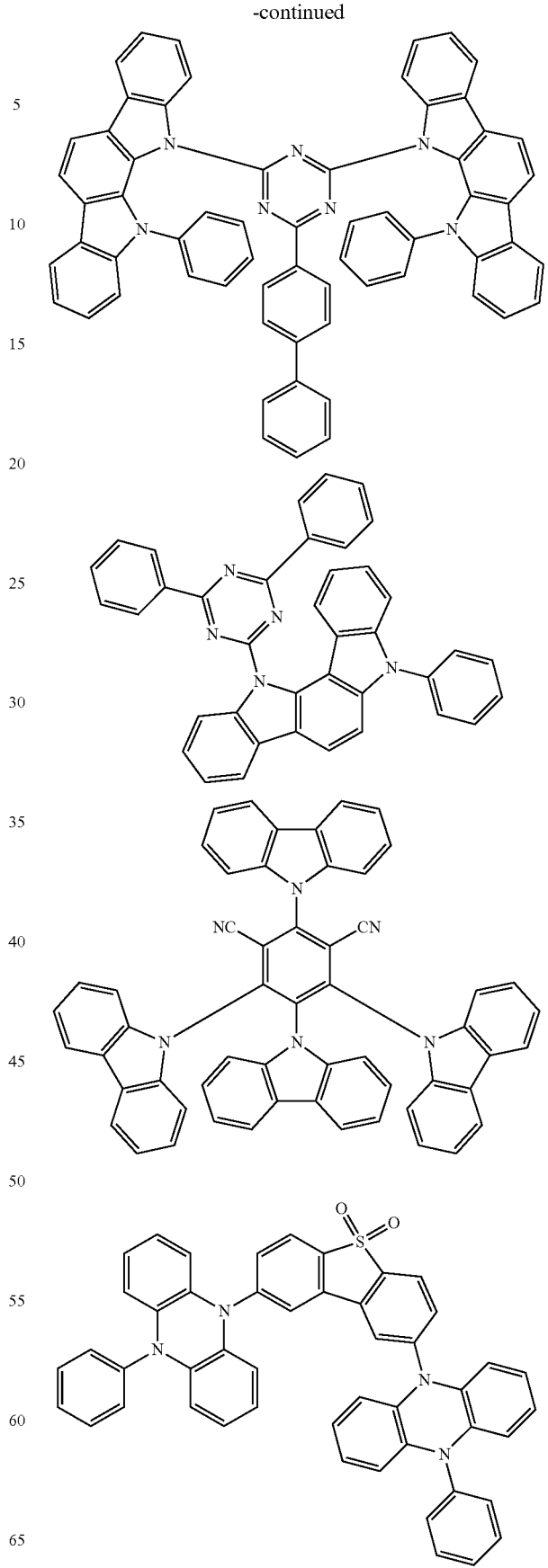

-continued

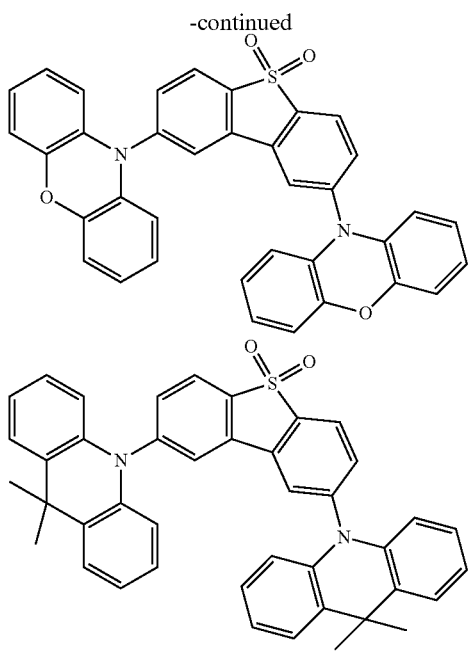

Only one kind of a thermally activated delayed fluorescent dopant material may be contained in a light emitting layer, or two or more kinds of thermally activated delayed fluorescent dopant materials may be contained therein. In addition, the thermally activated delayed fluorescent dopant may be used by being mixed with a phosphorescent dopant or a fluorescent dopant. The content of a thermally activated delayed fluorescent dopant material with respect to a host material is preferably 0.1 to 50% and more preferably 1 to 30%.

—Injection Layer—

An injection layer is a layer, such as a hole injection layer or an electron injection layer, provided between an electrode and an organic layer for reducing a drive voltage or improving luminance and may be present between an anode and a light emitting layer or a hole transport layer and between a cathode and a light emitting layer or an electron transport layer. The injection layer can be provided as necessary.

—Hole-Blocking Layer—

A hole-blocking layer has a function of an electron transport layer in a broad sense and is made of a hole-blocking material which has a function of transporting electrons and a significantly low ability of transporting holes. By blocking holes while transporting electrons, the probability of recombining electrons and holes in a light emitting layer can be increased.

A well-known hole-blocking layer material can be used in a hole-blocking layer, but the compound represented by General Formula (1) is preferably contained in a hole-blocking layer.

—Electron-Blocking Layer—

An electron-blocking layer has a function of a hole transport layer in a broad sense. By blocking electrons while transporting holes, the probability of recombining electrons and holes in a light emitting layer can be increased.

A well-known electron-blocking layer material can be used as the electron-blocking layer material, and a hole transport layer material to be described below can be used as necessary. The film thickness of an electron-blocking layer is preferably 3 to 100 nm and more preferably 5 to 30 nm.

—Exciton-Blocking Layer—

An exciton-blocking layer is a layer for blocking excitons generated by recombination of holes and electrons in a light emitting layer from being diffused in a charge transport layer. When this exciton-blocking layer is inserted, excitons can be efficiently confined in a light emitting layer and the luminous efficiency of a device can be improved. In a case of a device in which two or more light emitting layers are adjacent, an exciton-blocking layer can be inserted between the two adjacent light emitting layers.

A well-known exciton-blocking layer material can be used as the exciton-blocking layer material. Examples thereof include 1,3-dicarbazolylbenzene (mCP) and bis(2-methyl-8-quinolinolato)-4-phenylphenolato aluminum (III) (BAlq).

—Hole Transport Layer—

A hole transport layer is made of a hole transport material having a function of transporting holes, and a single hole transport layer or a plurality of hole transport layers can be provided.

As a hole transport material, one which is either an organic substance or an inorganic substance having either a function of injecting or transporting holes or electron barrier properties may be used. An arbitrary compound selected from conventionally well-known compounds can be used in a hole transport layer. Examples of such hole transport materials include porphyrin derivatives, arylamine derivatives, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, and conductive polymer oligomers, and especially thiophene oligomers. Porphyrin derivatives, arylamine derivatives, and styrylamine derivatives are preferably used, and arylamine derivatives are more preferably used.

—Electron Transport Layer—

An electron transport layer is made of a material having a function of transporting electrons, and a single electron transport layer or a plurality of electron transport layers can be provided.

An electron transport material (which may also serve as a hole-blocking material) may have a function of transmitting electrons injected from a cathode to a light emitting layer. An arbitrary compound selected from conventionally well-known compounds can be used in an electron transport layer, and examples thereof include polycyclic aromatic derivatives such as naphthalene, anthracene, and phenanthroline, tris(8-quinolinolato)aluminum (III) derivatives, phosphine oxide derivatives, nitro-substituted fluorene derivatives, diphenylquinone derivatives, thiopyran dioxide derivatives, carbodiimide, fluorenylidene methane derivatives, anthraquinodimethane, anthrone derivatives, bipyridine derivatives, quinoline derivatives, oxadiazole derivatives, benzoimidazole derivatives, benzothiazole derivatives, and indolocarbazole derivatives. Furthermore, polymer materials in which these materials are introduced into polymer chains or used as polymer main chains can also be used.

EXAMPLES

Hereinafter, the present invention will be described in more detail with reference to examples. However, the present invention is not limited to these examples and can be carried out in various forms as long as it does not exceed the gist thereof.

Example 1

Each thin film was laminated on a glass substrate, on which an anode made of ITO and having a film thickness of 110 nm was formed, with a vacuum degree of $4.0 \times 10^{-5}$ Pa through a vacuum vapor deposition method. First, 25 nm thick HAT-CN was formed on the ITO as a hole injection layer, and then 30 nm thick NPD was formed thereon as a hole transport layer. Next, 10 nm thick HT-1 was formed thereon as an electron-blocking layer. Next, a compound 1-4 as a first host, a compound 2-4 as a second host, and Ir (ppy)$_3$ as a luminescent dopant were subjected to co-vapor deposition from different vapor deposition sources to form a light emitting layer having a thickness of 40 nm. At this time, the co-vapor deposition was performed under the vapor deposition conditions where the concentration of Ir (ppy)$_3$ was 10 wt % and the weight ratio of the first host to the second host was 30:70. Next, 20 nm thick ET-1 was formed thereon as an electron transport layer. Furthermore, 1 nm thick LiF was formed on the electron transport layer as an electron injection layer. Finally, 70 nm thick Al was formed on the electron injection layer as a cathode to produce an organic EL device.

Examples 2 to 46

Organic EL devices were produced in the same manner as in Example 1 except that each compound shown in Tables 1 and 2 was used as a first host and a second host.

Examples 47 to 51

A first host and a second host were mixed with each other in advance to prepare a premixture and subjected to co-vapor deposition from one vapor deposition source.

A first host (0.30 g) and a second host (0.70 g) in Example 1 were weighed and mixed with each other while being ground in a mortar to obtain a premixture. Organic EL devices were produced in the same manner as in Example 1 except that this premixture was used.

Evaluation results of the produced organic EL devices are shown in Tables 1 and 2. In the tables, the luminance, the drive voltage, and the luminous efficiency are values when the drive current is 20 mA/cm$^2$ and are initial characteristics. LT70 is the time required for the initial luminance to attenuate to 70% and represents lifespan characteristics.

TABLE 1

| Ex. | First host compd. | Second host compd. | Luminance (cd/m2) | Voltage (V) | Power efficiency (lm/W) | LT70 (h) |
|---|---|---|---|---|---|---|
| 1 | 1-4 | 2-4 | 11000 | 4.4 | 39.3 | 1000 |
| 2 | 1-4 | 2-5 | 10500 | 4.2 | 39.3 | 1200 |
| 3 | 1-4 | 2-6 | 10500 | 4.2 | 39.3 | 1300 |
| 4 | 1-4 | 2-9 | 10500 | 4.2 | 39.3 | 1000 |
| 5 | 1-4 | 2-10 | 10500 | 4.1 | 40.2 | 1100 |
| 6 | 1-4 | 2-13 | 10500 | 4.1 | 40.2 | 1100 |
| 7 | 1-4 | 2-21 | 10500 | 4.1 | 40.2 | 1100 |
| 8 | 1-4 | 2-22 | 10500 | 4.2 | 39.3 | 1300 |
| 9 | 1-4 | 2-23 | 10500 | 4.1 | 40.2 | 1100 |
| 10 | 1-4 | 2-24 | 10500 | 4.0 | 41.2 | 1000 |
| 11 | 1-4 | 2-27 | 10500 | 4.0 | 41.2 | 1000 |
| 12 | 1-4 | 2-28 | 10500 | 4.0 | 41.2 | 1000 |
| 13 | 1-4 | 2-47 | 10500 | 4.0 | 41.2 | 1000 |
| 14 | 1-4 | 2-48 | 10500 | 4.0 | 41.2 | 1100 |
| 15 | 1-4 | 3-1 | 10500 | 4.2 | 39.3 | 1100 |
| 16 | 1-4 | 3-5 | 10500 | 4.2 | 39.3 | 1100 |
| 17 | 1-4 | 3-8 | 10500 | 4.2 | 39.3 | 1100 |
| 18 | 1-4 | 3-12 | 10500 | 4.2 | 39.3 | 1100 |
| 19 | 1-4 | 3-16 | 10800 | 4.3 | 39.5 | 1100 |
| 20 | 1-4 | 3-32 | 10800 | 4.3 | 39.5 | 1100 |
| 21 | 1-4 | 3-49 | 10500 | 4.0 | 41.2 | 1100 |
| 22 | 1-4 | 3-57 | 10500 | 4.1 | 40.2 | 1200 |
| 23 | 1-4 | 3-69 | 10500 | 4.1 | 40.2 | 1000 |
| 24 | 1-11 | 2-4 | 11000 | 4.4 | 39.3 | 1000 |
| 25 | 1-11 | 2-5 | 10800 | 4.2 | 40.4 | 1200 |

TABLE 2

| Ex. | First host compd. | Second host compd. | Luminance (cd/m2) | Voltage (V) | Power efficiency (lm/W) | LT70 (h) |
|---|---|---|---|---|---|---|
| 26 | 1-11 | 2-6 | 10800 | 4.2 | 40.4 | 1300 |
| 27 | 1-11 | 2-9 | 10800 | 4.2 | 40.4 | 1000 |
| 28 | 1-11 | 2-10 | 10200 | 4.1 | 39.1 | 1100 |
| 29 | 1-11 | 2-13 | 10200 | 4.1 | 39.1 | 1100 |
| 30 | 1-11 | 2-21 | 10200 | 4.1 | 39.1 | 1100 |
| 31 | 1-11 | 2-22 | 10600 | 4.2 | 39.6 | 1300 |
| 32 | 1-11 | 2-23 | 10400 | 4.1 | 39.8 | 1100 |
| 33 | 1-11 | 2-24 | 10600 | 4.2 | 39.6 | 1000 |
| 34 | 1-11 | 2-27 | 10600 | 4.2 | 39.6 | 1000 |
| 35 | 1-11 | 2-28 | 10600 | 4.2 | 39.6 | 1000 |
| 36 | 1-11 | 2-47 | 10800 | 4.3 | 39.5 | 1000 |
| 37 | 1-11 | 2-48 | 10500 | 4.1 | 40.2 | 1100 |
| 38 | 1-11 | 3-1 | 11000 | 4.3 | 40.2 | 1100 |
| 39 | 1-11 | 3-5 | 10800 | 4.3 | 39.5 | 1100 |
| 40 | 1-11 | 3-8 | 10800 | 4.3 | 39.5 | 1100 |
| 41 | 1-11 | 3-12 | 10700 | 4.3 | 39.1 | 1100 |
| 42 | 1-11 | 3-16 | 11000 | 4.4 | 39.3 | 1100 |
| 43 | 1-11 | 3-32 | 11000 | 4.4 | 39.3 | 1100 |
| 44 | 1-11 | 3-49 | 10700 | 4.2 | 40.0 | 1100 |
| 45 | 1-11 | 3-57 | 10800 | 4.2 | 40.4 | 1200 |
| 46 | 1-11 | 3-69 | 10800 | 4.3 | 39.5 | 1000 |
| 47 | 1-4 | 2-5 | 10500 | 4.2 | 39.3 | 1200 |
| 48 | 1-4 | 2-13 | 10500 | 4.1 | 40.2 | 1100 |
| 49 | 1-4 | 3-12 | 10500 | 4.2 | 39.3 | 1100 |
| 50 | 1-4 | 3-16 | 10800 | 4.3 | 39.5 | 1100 |
| 51 | 1-4 | 3-57 | 10500 | 4.1 | 40.2 | 1200 |

Comparative Example 1

An organic EL device was produced in the same manner as in Example 1 except that a compound 1-1 was used alone as a host. The thickness of a light emitting layer and the concentration of a luminescent dopant are the same as those in Example 1.

Comparative Examples 2 to 15

Organic EL devices were produced in the same manner as in Comparative Example 1 except that each compound shown in Table 3 was used alone as a host.

Comparative Examples 16 to 19

Organic EL devices were produced in the same manner as in Example 1 except that a compound A was used as a first host and a compound 2-5, a compound 2-48, a compound 3-8, or a compound 3-49 was used as a second host.

Comparative Examples 20 to 23

Organic EL devices were produced in the same manner as in Comparative Examples 16 to 19 except that a compound B was used as a first host.

Comparative Examples 24 to 27

Organic EL devices were produced in the same manner as in Comparative Examples 16 to 19 except that a compound C was used as a first host.

Evaluation results of the produced organic EL devices are shown in Table 3.

TABLE 3

| Comp. Ex. | First host compd. | Second host compd. | Luminance (cd/m2) | Voltage (V) | Power efficiency (lm/W) | LT70 (h) |
|---|---|---|---|---|---|---|
| 1 | 1-1 | — | 7000 | 3.3 | 33.3 | 700 |
| 2 | 1-3 | — | 7100 | 3.3 | 33.8 | 700 |
| 3 | 1-4 | — | 7000 | 3.2 | 34.4 | 850 |
| 4 | 1-11 | — | 7000 | 3.2 | 34.4 | 800 |
| 5 | 1-20 | — | 7000 | 3.3 | 33.3 | 700 |
| 6 | 1-24 | — | 7000 | 3.1 | 35.5 | 800 |
| 7 | — | 2-4 | 9500 | 4.7 | 31.8 | 500 |
| 8 | — | 2-5 | 9000 | 4.7 | 30.1 | 550 |
| 9 | — | 2-6 | 8000 | 4.9 | 25.6 | 500 |
| 10 | — | 2-13 | 8000 | 4.9 | 25.6 | 500 |
| 11 | — | 2-48 | 8000 | 4.7 | 26.7 | 450 |
| 12 | — | 3-8 | 8000 | 4.7 | 26.7 | 450 |
| 13 | — | 3-12 | 10000 | 4.9 | 32.1 | 550 |
| 14 | — | 3-16 | 10000 | 4.9 | 32.1 | 550 |
| 15 | — | 3-49 | 10000 | 4.9 | 32.1 | 600 |
| 16 | A | 2-5 | 8500 | 3.9 | 34.2 | 700 |
| 17 | A | 2-48 | 8500 | 3.9 | 34.2 | 700 |
| 18 | A | 3-8 | 8800 | 3.9 | 35.4 | 700 |
| 19 | A | 3-49 | 8700 | 3.8 | 36.0 | 700 |
| 20 | B | 2-5 | 10500 | 4.6 | 35.9 | 700 |
| 21 | B | 2-48 | 10500 | 4.5 | 36.7 | 700 |
| 22 | B | 3-8 | 10500 | 4.7 | 35.1 | 750 |
| 23 | B | 3-49 | 10500 | 4.6 | 35.9 | 750 |
| 24 | C | 2-5 | 10000 | 4.5 | 34.9 | 750 |
| 25 | C | 2-48 | 10000 | 4.4 | 35.7 | 700 |
| 26 | C | 3-8 | 10000 | 4.4 | 35.7 | 700 |
| 27 | C | 3-49 | 10000 | 4.5 | 34.9 | 850 |

It can be seen from Tables 1 and 2 that Examples 1 to 51 have improved power efficiency and lifespan characteristics and show favorable characteristics.

Example 52

Each thin film was laminated on a glass substrate, on which an anode made of ITO and having a film thickness of 110 nm was formed, with a vacuum degree of $4.0 \times 10^{-5}$ Pa through a vacuum vapor deposition method. First, 25 nm thick HAT-CN was formed on the ITO as a hole injection layer, and then 45 nm thick NPD was formed thereon as a hole transport layer. Next, 10 nm thick HT-1 was formed thereon as an electron-blocking layer. Next, a compound 1-4 as a first host, a compound 2-4 as a second host, and Ir(piq)$_2$acac as a luminescent dopant were subjected to co-vapor deposition from different vapor deposition sources to form a light emitting layer having a thickness of 40 nm. At this time, the co-vapor deposition was performed under the vapor deposition condition where the concentration of Ir(piq)$_2$acac was 6.0 wt %. Next, 37.5 nm thick ET-1 was formed thereon as an electron transport layer. Then, 1 nm thick LiF was formed on the electron transport layer as an electron injection layer. Finally, 70 nm thick Al was formed on the electron injection layer as a cathode to produce an organic EL device.

Examples 53 to 73

Organic EL devices were produced in the same manner as in Example 52 except that each compound shown in Table 4 was used as a first host and a second host.

Evaluation results of the produced organic EL devices are shown in Table 4. Here, LT95 is the time required for the initial luminance to attenuate to 95% and represents lifespan characteristics.

TABLE 4

| Ex. | First host compd. | Second host compd. | Luminance (cd/m2) | Voltage (V) | Power efficiency (lm/W) | LT95 (h) |
|---|---|---|---|---|---|---|
| 52 | 1-4 | 2-4 | 5000 | 4.4 | 17.8 | 250 |
| 53 | 1-4 | 2-5 | 5000 | 4.2 | 18.7 | 250 |
| 54 | 1-4 | 2-6 | 5000 | 4.2 | 18.7 | 250 |
| 55 | 1-4 | 2-13 | 5000 | 4.1 | 19.2 | 200 |
| 56 | 1-4 | 2-48 | 5000 | 4.0 | 19.6 | 200 |
| 57 | 1-4 | 3-1 | 5000 | 4.2 | 18.7 | 250 |
| 58 | 1-4 | 3-5 | 5000 | 4.2 | 18.7 | 200 |
| 59 | 1-4 | 3-8 | 5000 | 4.2 | 18.7 | 200 |
| 60 | 1-4 | 3-12 | 5000 | 4.2 | 18.7 | 250 |
| 61 | 1-4 | 3-16 | 5000 | 4.3 | 18.3 | 250 |
| 62 | 1-4 | 3-57 | 5000 | 4.1 | 19.2 | 200 |
| 63 | 1-11 | 2-4 | 5000 | 4.4 | 17.8 | 250 |
| 64 | 1-11 | 2-5 | 5000 | 4.2 | 18.7 | 250 |
| 65 | 1-11 | 2-6 | 5000 | 4.2 | 18.7 | 250 |
| 66 | 1-11 | 2-13 | 5000 | 4.1 | 19.2 | 200 |
| 67 | 1-11 | 2-48 | 5000 | 4.0 | 19.6 | 200 |
| 68 | 1-11 | 3-1 | 5000 | 4.2 | 18.7 | 250 |
| 69 | 1-11 | 3-5 | 5000 | 4.2 | 18.7 | 200 |
| 70 | 1-11 | 3-8 | 5000 | 4.2 | 18.7 | 200 |
| 71 | 1-11 | 3-12 | 5000 | 4.2 | 18.7 | 250 |
| 72 | 1-11 | 3-16 | 5000 | 4.3 | 18.3 | 250 |
| 73 | 1-11 | 3-57 | 5000 | 4.1 | 19.2 | 200 |

Comparative Example 28

An organic EL device was produced in the same manner as in Example 52 except that a compound 1-1 was used alone as a host. The thickness of a light emitting layer and the concentration of a luminescent dopant are the same as those in Example 52.

Comparative Examples 29 and 41

Organic EL devices were produced in the same manner as in Comparative Example 28 except that each compound shown in Table 5 was used alone as a host.

Comparative Examples 42 to 45

Organic EL devices were produced in the same manner as in Example 52 except that a compound A was used as a first host and a compound 2-5, compound 2-48, a compound 3-8, or a compound 3-49 was used as a second host.

Comparative Examples 46 to 49

Organic EL devices were produced in the same manner as in Comparative Examples 42 to 45 except that a compound B was used as a first host.

Comparative Examples 44 and 50 to 53

Organic EL devices were produced in the same manner as in Comparative Examples 42 to 45 except that a compound C was used as a first host.

Evaluation results of the produced organic EL devices are shown in Table 5.

TABLE 5

| Comp. Ex. | First host compd. | Second host compd. | Luminance (cd/m2) | Voltage (V) | Power efficiency (lm/W) | LT95 (h) |
|---|---|---|---|---|---|---|
| 28 | 1-1 | — | 3000 | 3.4 | 13.9 | 150 |
| 29 | 1-3 | — | 3000 | 3.4 | 13.9 | 150 |
| 30 | 1-4 | — | 3000 | 3.3 | 14.3 | 180 |
| 31 | 1-11 | — | 3000 | 3.4 | 13.9 | 180 |
| 32 | 1-20 | — | 3000 | 3.4 | 13.9 | 150 |
| 33 | 1-24 | — | 3200 | 3.6 | 14.0 | 180 |
| 34 | — | 2-4 | 4000 | 4.7 | 13.4 | 100 |
| 35 | — | 2-5 | 4000 | 4.7 | 13.4 | 100 |
| 36 | — | 2-6 | 4000 | 4.9 | 12.8 | 100 |
| 37 | — | 2-13 | 4000 | 4.9 | 12.8 | 100 |
| 38 | — | 2-48 | 4000 | 4.7 | 13.4 | 100 |
| 39 | — | 3-12 | 4000 | 4.7 | 13.4 | 80 |
| 40 | — | 3-16 | 4000 | 4.9 | 12.8 | 90 |
| 41 | — | 3-49 | 4000 | 4.9 | 12.8 | 100 |
| 42 | A | 2-5 | 4500 | 4.4 | 16.1 | 150 |
| 43 | A | 2-48 | 4500 | 4.1 | 17.2 | 150 |
| 44 | A | 3-8 | 4500 | 4.4 | 16.1 | 150 |
| 45 | A | 3-49 | 4500 | 4.5 | 15.7 | 150 |
| 46 | B | 2-5 | 4500 | 4.0 | 17.7 | 120 |
| 47 | B | 2-48 | 4500 | 4.5 | 15.7 | 120 |
| 48 | B | 3-8 | 4500 | 4.5 | 15.7 | 120 |
| 49 | B | 3-49 | 4500 | 4.2 | 16.8 | 120 |
| 50 | C | 2-5 | 4500 | 4.5 | 15.7 | 110 |
| 51 | C | 2-48 | 4500 | 4.4 | 16.1 | 110 |
| 52 | C | 3-8 | 4500 | 4.4 | 16.1 | 110 |
| 53 | C | 3-49 | 4500 | 4.5 | 15.7 | 110 |

It can be seen from Table 4 that Examples 52 to 73 have improved power efficiency and lifespan characteristics and show favorable characteristics.

The compounds used in the examples are shown below.

[C23]

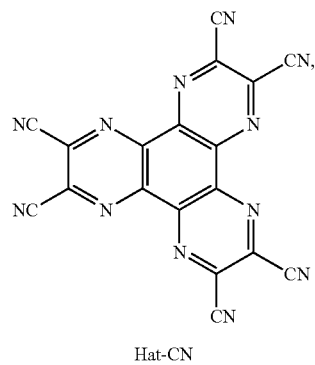

Hat-CN

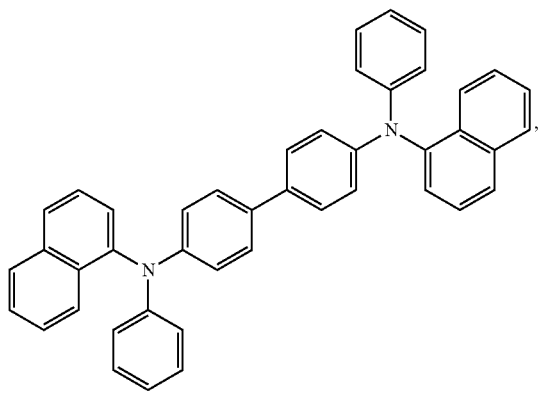

NPD

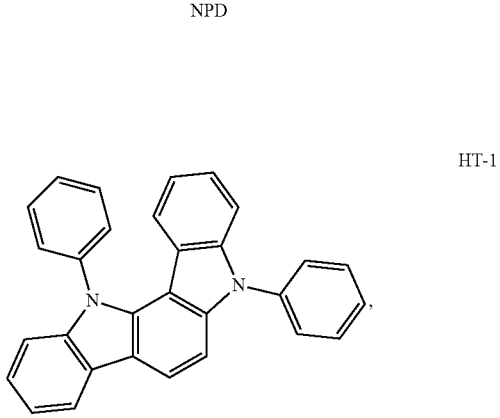

HT-1

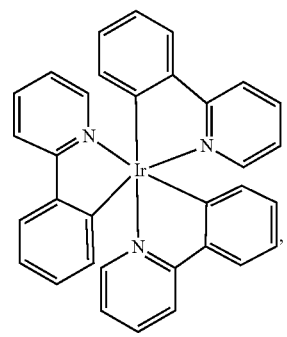

Ir(ppy)₃

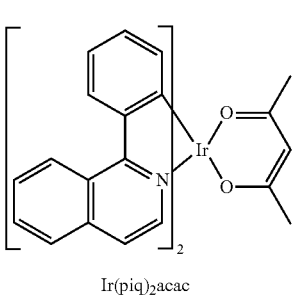

Ir(piq)₂acac

ET-1

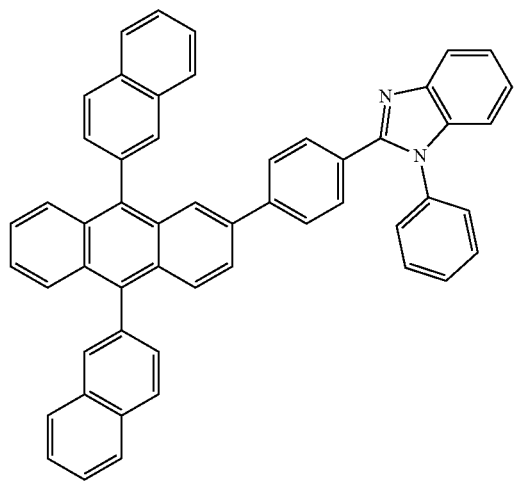

Compound A

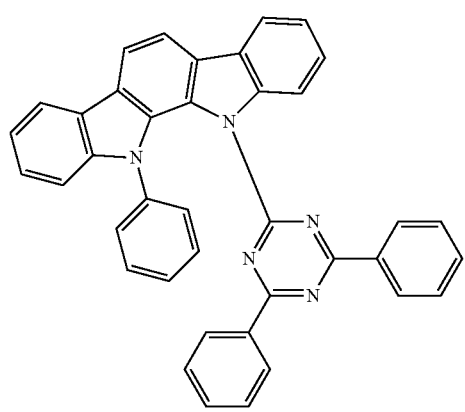

Compound B

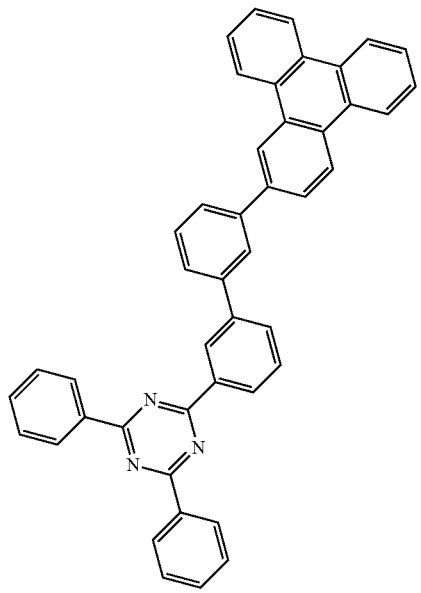

Compound C

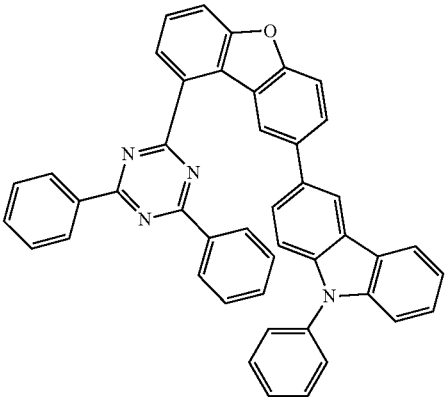

INDUSTRIAL APPLICABILITY

The organic EL device of the present invention has a low drive voltage, high efficiency, and high drive stability.

REFERENCE SIGNS LIST

1 Substrate
2 Anode
3 Hole injection layer
4 Hole transport layer
5 Light emitting layer
6 Electron transport layer
7 Cathode

The invention claimed is:
1. An organic electroluminescent device comprising:
one or more light emitting layers between an anode and a cathode facing each other,
wherein at least one light emitting layer contains a first host selected from compounds represented by General Formula (1) below and a second host selected from compounds represented by General Formula (2) or (3) below,

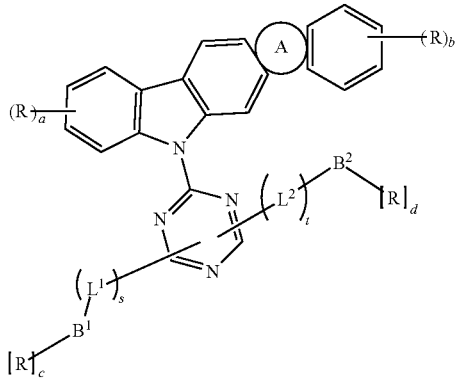

(1)

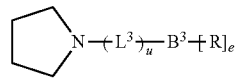

(1a)

(1b)

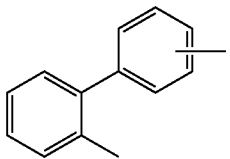

wherein, a ring A is a heterocyclic ring represented by Formula (1a) and condensed with an adjacent ring at an arbitrary position, R's are independently hydrogen, an aliphatic hydrocarbon group having 1 to 10 carbon atoms, an aromatic hydrocarbon group having 6 to 10 carbon atoms, or an aromatic heterocyclic group having 3 to 12 carbon atoms, $L^1$, $L^2$ and $L^3$ are independently a direct bond, an aromatic hydrocarbon group having 6 to 10 carbon atoms, or an aromatic heterocyclic group having 3 to 12 carbon atoms, $B^1$, $B^2$ and $B^3$ independently represent a direct bond or a biphenyldiyl group represented by Formula (1b), at least one of $B^1$, $B^2$ and $B^3$ is the biphenyldiyl group, and a, b, c, d, and e each independently represent an integer of 0 to 3, and s, t, and u each independently represent an integer of 1 and 2, (2)

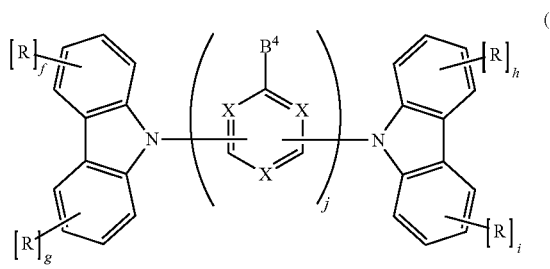

wherein, R's independently represent hydrogen, an alkyl group having 1 to 20 carbon atoms, an acyl group having 2 to 20 carbon atoms, an alkoxy group having 2 to 20 carbon atoms, an aromatic hydrocarbon group having 6 to 24 carbon atoms, or an aromatic heterocyclic group having 3 to 16 carbon atoms, but are not a carbazole ring group, $B^4$'s are independently hydrogen, an aromatic hydrocarbon group having 6 to 24 carbon atoms, or an aromatic heterocyclic group having 3 to 16 carbon atoms, the aromatic hydrocarbon group or the aromatic heterocyclic group may have a substituent, j represents an integer of 1 to 6, X's independently represent N, C—R', or C—, each R' independently represents hydrogen, an alkyl group having 1 to 20 carbon atoms, an alkoxy group having 1 to 20 carbon atoms, and a diarylamino group having 12 to 44 carbon atoms, and f, g, h, and i independently represent an integer of 1 to 3, and (3)

[R]̶ₘ—B⁵—(L⁴)ₚ—(C)

(3a)

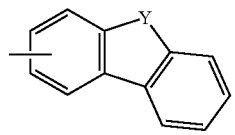

wherein, a ring C is a heterocyclic group represented by Formula (3a), $L^4$ is independently a direct bond, an aromatic hydrocarbon group having 6 to 10 carbon atoms, or an aromatic heterocyclic group having 3 to 16 carbon atoms, $B^5$ is a direct bond or an aromatic hydrocarbon group having 6 to 22 carbon atoms, R's are an aromatic hydrocarbon group having 6 to 10 carbon atoms, an aromatic heterocyclic group having 3 to 16 carbon atoms, an alkyl group having 1 to 10 carbon atoms, or a cycloalkyl group having 3 to 11 carbon atoms, Y independently represents O or S, m is a number of substitutions and represent an integer of 1, and p is a number of repetitions and is an integer of 1 to 4.

2. The organic electroluminescent device according to claim 1, wherein, in General Formula (1), $B^3$ is a biphenyldiyl group represented by Formula (1b).

3. The organic electroluminescent device according to claim 1, wherein, in General Formula (1), a, b, and c are 0.

4. The organic electroluminescent device according to claim 1, wherein, in General Formula (2), j is an integer of 1 to 3.

5. The organic electroluminescent device according to claim 1, wherein, in General Formula (2), X's are N or C—H.

6. The organic electroluminescent device according to claim 1, wherein, in General Formula (3), $L^4$ and $B^5$ are a direct bond.

7. The organic electroluminescent device according to claim 1, wherein the compounds represented by General Formula (1) are compounds represented by any one of Formulae (8) to (11) below, (8)

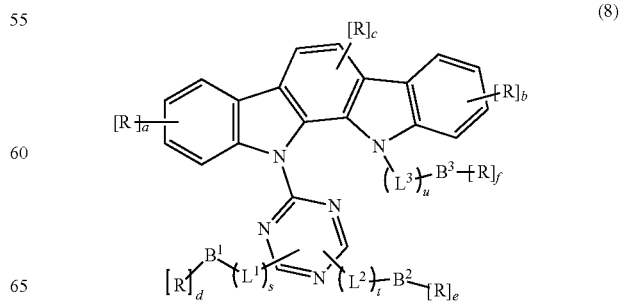

-continued

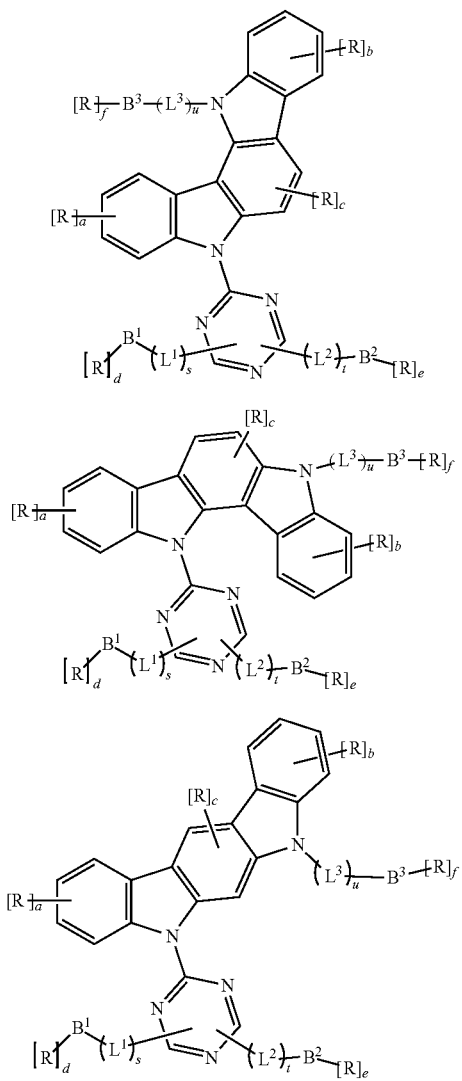

(9)

(10)

(11)

wherein $B^1$ to $B^3$, $L^1$ to $L^3$, R, a to f, and s to u have the same meaning as those in General Formula (1).

8. The organic electroluminescent device according to claim 1,
wherein a proportion of the first host is greater than 20 wt % and less than 55 wt % based on the total amount of the first host and the second host.

9. The organic electroluminescent device according to claim 1,
wherein the light emitting layer contains a luminescent dopant material, and
wherein the luminescent dopant material is an organic metal complex containing at least one metal selected from the group consisting of ruthenium, rhodium, palladium, silver, rhenium, osmium, iridium, platinum, and gold.

10. The organic electroluminescent device according to claim 1,
wherein the light emitting layer contains a luminescent dopant material, and
wherein the luminescent dopant material is a thermally activated delayed fluorescent dopant material.

11. The organic electroluminescent device according to claim 1,
wherein a hole-blocking layer is provided adjacent to the light emitting layer, and the compound represented by General Formula (1) is contained in the hole-blocking layer.

12. A method for producing an organic electroluminescent device, the method comprising:
a step of mixing a first host with a second host to prepare a premixture and then vapor-depositing the host material containing the hosts to form a light emitting layer when producing the organic electroluminescent device according to claim 1.

13. The method for producing an organic electroluminescent device according to claim 12,
wherein a difference in 50% weight reduction temperature between the first host and the second host is within 20° C.

* * * * *